US012644115B2

(12) United States Patent
Chen et al.

(10) Patent No.: US 12,644,115 B2
(45) Date of Patent: Jun. 2, 2026

(54) METHYLATION-MEDIATED ADAPTER REMOVAL ON NUCLEIC ACID SEQUENCES

(71) Applicant: Twist Bioscience Corporation, South San Francisco, CA (US)

(72) Inventors: Siyuan Chen, San Mateo, CA (US); Xuan Yu Elian Lee, San Mateo, CA (US); David Lin, Dublin, CA (US); Daniel J. Ramirez, South San Francisco, CA (US); Tavneet Gill, South San Francisco, CA (US); Patrick Cherry, San Francisco, CA (US); Esteban Toro, Fremont, CA (US)

(73) Assignee: Twist Bioscience Corporation, South San Francisco, CA (US)

( * ) Notice: Subject to any disclaimer, the term of this patent is extended or adjusted under 35 U.S.C. 154(b) by 586 days.

(21) Appl. No.: 18/179,311

(22) Filed: Mar. 6, 2023

(65) Prior Publication Data

US 2023/0407290 A1     Dec. 21, 2023

Related U.S. Application Data

(60) Provisional application No. 63/317,466, filed on Mar. 7, 2022.

(51) Int. Cl.
*C12N 15/10* (2006.01)
(52) U.S. Cl.
CPC ................................ *C12N 15/1031* (2013.01)
(58) Field of Classification Search
CPC .. C12N 15/1031; C12N 9/22; C12N 15/1093; C12N 15/66
See application file for complete search history.

(56) References Cited

U.S. PATENT DOCUMENTS

| | | | |
|---|---|---|---|
| 5,368,823 A | 11/1994 | McGraw et al. | |
| 5,474,796 A | 12/1995 | Brennan | |
| 5,534,507 A | 7/1996 | Cama et al. | |
| 5,677,195 A | 10/1997 | Winkler et al. | |
| 5,843,767 A | 12/1998 | Beattie | |
| 6,013,440 A | 1/2000 | Lipshutz et al. | |
| 6,028,189 A | 2/2000 | Blanchard | |
| 6,419,883 B1 | 7/2002 | Blanchard | |
| 6,472,147 B1 | 10/2002 | Janda et al. | |
| 6,492,107 B1 | 12/2002 | Kauffman et al. | |
| 6,893,816 B1 | 5/2005 | Beattie | |
| 7,163,660 B2 | 1/2007 | Lehmann | |
| 7,202,264 B2 | 4/2007 | Ravikumar et al. | |
| 8,198,071 B2 | 6/2012 | Goshoo et al. | |
| 9,403,141 B2 | 8/2016 | Banyai et al. | |
| 9,409,139 B2 | 8/2016 | Banyai et al. | |
| 9,555,388 B2 | 1/2017 | Banyai et al. | |
| 9,677,067 B2 | 6/2017 | Toro et al. | |
| 9,745,619 B2 | 8/2017 | Rabbani et al. | |
| 9,765,387 B2 | 9/2017 | Rabbani et al. | |
| 9,833,761 B2 | 12/2017 | Banyai et al. | |

| | | | |
|---|---|---|---|
| 9,839,894 B2 | 12/2017 | Banyai et al. | |
| 9,889,423 B2 | 2/2018 | Banyai et al. | |
| 9,895,673 B2 | 2/2018 | Peck et al. | |
| 9,981,239 B2 | 5/2018 | Banyai et al. | |
| 10,053,688 B2 | 8/2018 | Cox | |
| 10,272,410 B2 | 4/2019 | Banyai et al. | |
| 10,384,188 B2 | 8/2019 | Banyai et al. | |
| 10,384,189 B2 | 8/2019 | Peck | |
| 10,417,457 B2 | 9/2019 | Peck | |
| 10,583,415 B2 | 3/2020 | Banyai et al. | |
| 10,618,024 B2 | 4/2020 | Banyai et al. | |
| 10,632,445 B2 | 4/2020 | Banyai et al. | |
| 10,639,609 B2 | 5/2020 | Banyai et al. | |
| 10,669,304 B2 | 6/2020 | Indermuhle et al. | |
| 10,744,477 B2 | 8/2020 | Banyai et al. | |
| 10,754,994 B2 | 8/2020 | Peck | |
| 10,773,232 B2 | 9/2020 | Banyai et al. | |
| 10,844,373 B2 | 11/2020 | Cox et al. | |
| 10,894,242 B2 | 1/2021 | Marsh et al. | |
| 10,894,959 B2 | 1/2021 | Cox et al. | |
| 10,907,274 B2 | 2/2021 | Cox | |
| 10,936,953 B2 | 3/2021 | Bramlett et al. | |
| 10,969,965 B2 | 4/2021 | Malina et al. | |
| 10,975,372 B2 | 4/2021 | Cox et al. | |
| 10,987,648 B2 | 4/2021 | Peck et al. | |
| 11,185,837 B2 | 11/2021 | Banyai et al. | |
| 11,214,798 B2 | 1/2022 | Brown | |
| 11,263,354 B2 | 3/2022 | Peck | |
| 11,332,738 B2 | 5/2022 | Nugent et al. | |

(Continued)

FOREIGN PATENT DOCUMENTS

| | | |
|---|---|---|
| CN | 101277758 A | 10/2008 |
| EP | 3030682 A2 | 6/2016 |

(Continued)

OTHER PUBLICATIONS

Agbavwe et al.: Efficiency, Error and Yield in Light-Directed Maskless Synthesis of DNA Microarrays. Journal of Nanobiotechnology. 9(57):1-17 (2011).
Altschul et al.: Basic local alignment search tool. Journal of Molecular Biology. 215(3):403-410 (1990).
Altschul et al. Gapped BLAST and PSI-BLAST: a new generation of protein database search programs. Nucleic Acids Res. 25:3389-3402 (1997).
Arkles et al.: The Role of Polarity in the Structure of Silanes Employed in Surface Modification. Silanes and Other Coupling Agents. 5:51-64 (2009).
ATDBio. Nucleic Acid Structure, Nucleic Acids Book, 9 pages, published on Jan. 22, 2005. from: http://www.atdbio.com/content/5/Nucleic-acid-structure.

(Continued)

*Primary Examiner* — Paul J Holland
(74) *Attorney, Agent, or Firm* — Bookoff McAndrews, PLLC

(57) ABSTRACT

Provided herein are methods, systems, and compositions for efficient nucleic acid assembly with improved representation and distribution. Provided herein are methods, systems, and compositions for efficient nucleic acid assembly of nucleic acids encoding genes for use in various downstream processes.

20 Claims, 32 Drawing Sheets

Specification includes a Sequence Listing.

(56) References Cited

U.S. PATENT DOCUMENTS

| | | | |
|---|---|---|---|
| 11,332,740 | B2 | 5/2022 | Nugent et al. |
| 11,377,676 | B2 | 7/2022 | Wu et al. |
| 11,407,837 | B2 | 8/2022 | Glanville |
| 11,452,980 | B2 | 9/2022 | Banyai et al. |
| 11,492,665 | B2 | 11/2022 | Zeitoun et al. |
| 11,492,727 | B2 | 11/2022 | Tabibiazar et al. |
| 11,492,728 | B2 | 11/2022 | Sato |
| 11,512,347 | B2 | 11/2022 | Peck |
| 11,550,939 | B2 | 1/2023 | Peck et al. |
| 11,559,778 | B2 | 1/2023 | Banyai et al. |
| 11,562,103 | B2 | 1/2023 | Peck |
| 11,691,118 | B2 | 7/2023 | Banyai et al. |
| 11,697,668 | B2 | 7/2023 | Indermuhle et al. |
| 2001/0018512 | A1 | 8/2001 | Blanchard |
| 2002/0025561 | A1 | 2/2002 | Hodgson |
| 2002/0094533 | A1 | 7/2002 | Hess et al. |
| 2002/0095073 | A1 | 7/2002 | Jacobs et al. |
| 2002/0160536 | A1 | 10/2002 | Regnier et al. |
| 2002/0164824 | A1 | 11/2002 | Xiao et al. |
| 2003/0120035 | A1 | 6/2003 | Gao et al. |
| 2003/0171325 | A1 | 9/2003 | Gascoyne et al. |
| 2004/0087008 | A1 | 5/2004 | Schembri |
| 2004/0259146 | A1 | 12/2004 | Friend et al. |
| 2005/0137805 | A1 | 6/2005 | Lewin et al. |
| 2005/0227235 | A1 | 10/2005 | Carr et al. |
| 2006/0127920 | A1 | 6/2006 | Church et al. |
| 2007/0196834 | A1 | 8/2007 | Cerrina et al. |
| 2008/0085511 | A1 | 4/2008 | Peck et al. |
| 2008/0085514 | A1 | 4/2008 | Peck et al. |
| 2008/0227160 | A1 | 9/2008 | Kool |
| 2008/0287320 | A1 | 11/2008 | Baynes et al. |
| 2008/0300842 | A1 | 12/2008 | Govindarajan et al. |
| 2009/0062129 | A1 | 3/2009 | McKernan et al. |
| 2009/0239759 | A1 | 9/2009 | Balch |
| 2009/0285825 | A1 | 11/2009 | Kini et al. |
| 2010/0004143 | A1 | 1/2010 | Shibahara |
| 2010/0099103 | A1 | 4/2010 | Hsieh et al. |
| 2010/0111768 | A1 | 5/2010 | Banerjee et al. |
| 2010/0216648 | A1 | 8/2010 | Staehler et al. |
| 2010/0311960 | A1 | 12/2010 | Dellinger |
| 2011/0172127 | A1 | 7/2011 | Jacobson et al. |
| 2011/0217738 | A1 | 9/2011 | Jacobson |
| 2012/0129704 | A1 | 5/2012 | Gunderson et al. |
| 2012/0164691 | A1 | 6/2012 | Eshoo et al. |
| 2012/0231968 | A1 | 9/2012 | Bruhn et al. |
| 2012/0264653 | A1 | 10/2012 | Carr et al. |
| 2013/0017642 | A1 | 1/2013 | Milgrew et al. |
| 2013/0017977 | A1 | 1/2013 | Oleinikov |
| 2013/0065017 | A1 | 3/2013 | Sieber |
| 2013/0109595 | A1 | 5/2013 | Routenberg |
| 2013/0109596 | A1 | 5/2013 | Peterson et al. |
| 2013/0130321 | A1 | 5/2013 | Staehler et al. |
| 2013/0165328 | A1 | 6/2013 | Previte et al. |
| 2014/0106394 | A1 | 4/2014 | Ko et al. |
| 2014/0178992 | A1 | 6/2014 | Nakashima et al. |
| 2015/0038373 | A1 | 2/2015 | Banyai et al. |
| 2015/0120265 | A1 | 4/2015 | Amirav-Drory et al. |
| 2015/0196917 | A1 | 7/2015 | Kay et al. |
| 2016/0089651 | A1 | 3/2016 | Banyai |
| 2016/0090592 | A1 | 3/2016 | Banyai et al. |
| 2016/0096160 | A1 | 4/2016 | Banyai et al. |
| 2016/0251651 | A1 | 9/2016 | Banyai et al. |
| 2016/0303535 | A1 | 10/2016 | Banyai et al. |
| 2016/0333340 | A1 | 11/2016 | Wu |
| 2016/0339409 | A1 | 11/2016 | Banyai et al. |
| 2016/0340672 | A1 | 11/2016 | Banyai et al. |
| 2016/0354752 | A1 | 12/2016 | Banyai et al. |
| 2017/0095785 | A1 | 4/2017 | Banyai et al. |
| 2017/0159044 | A1 | 6/2017 | Toro et al. |
| 2017/0327819 | A1 | 11/2017 | Banyai et al. |
| 2017/0357752 | A1 | 12/2017 | Diggans |
| 2017/0362589 | A1 | 12/2017 | Banyai et al. |
| 2018/0029001 | A1 | 2/2018 | Banyai et al. |
| 2018/0104664 | A1 | 4/2018 | Fernandez |
| 2018/0142289 | A1 | 5/2018 | Zeitoun et al. |
| 2018/0264428 | A1 | 9/2018 | Banyai et al. |
| 2018/0282721 | A1 | 10/2018 | Cox et al. |
| 2018/0305737 | A1 | 10/2018 | Osborne et al. |
| 2019/0314783 | A1 | 10/2019 | Banyai et al. |
| 2019/0352635 | A1 | 11/2019 | Toro et al. |
| 2019/0366293 | A1 | 12/2019 | Banyai et al. |
| 2019/0366294 | A1 | 12/2019 | Banyai et al. |
| 2020/0102611 | A1 | 4/2020 | Zeitoun et al. |
| 2020/0156037 | A1 | 5/2020 | Banyai et al. |
| 2020/0181667 | A1 | 6/2020 | Wu et al. |
| 2020/0222875 | A1 | 7/2020 | Peck et al. |
| 2020/0283760 | A1 | 9/2020 | Nugent et al. |
| 2020/0299684 | A1 | 9/2020 | Toro et al. |
| 2021/0002710 | A1 | 1/2021 | Gantt et al. |
| 2021/0040476 | A1 | 2/2021 | Cox et al. |
| 2021/0071168 | A1 | 3/2021 | Nugent et al. |
| 2021/0102192 | A1 | 4/2021 | Tabibiazar et al. |
| 2021/0102195 | A1 | 4/2021 | Sato et al. |
| 2021/0102198 | A1 | 4/2021 | Cox et al. |
| 2021/0115594 | A1 | 4/2021 | Cox et al. |
| 2021/0129108 | A1 | 5/2021 | Marsh et al. |
| 2021/0142182 | A1 | 5/2021 | Bramlett et al. |
| 2021/0170356 | A1 | 6/2021 | Peck et al. |
| 2021/0179724 | A1 | 6/2021 | Sato et al. |
| 2021/0180046 | A1 | 6/2021 | Cox et al. |
| 2021/0207197 | A1 | 7/2021 | Gantt et al. |
| 2021/0332078 | A1 | 10/2021 | Wu |
| 2021/0348220 | A1 | 11/2021 | Zeitoun et al. |
| 2021/0355194 | A1 | 11/2021 | Sato et al. |
| 2021/0395344 | A1 | 12/2021 | Sato et al. |
| 2022/0032256 | A1 | 2/2022 | Lackey et al. |
| 2022/0064206 | A1 | 3/2022 | Fernandez et al. |
| 2022/0064313 | A1 | 3/2022 | Sato et al. |
| 2022/0064628 | A1 | 3/2022 | Toro et al. |
| 2022/0106586 | A1 | 4/2022 | Nugent et al. |
| 2022/0106590 | A1 | 4/2022 | Arbiza et al. |
| 2022/0135690 | A1 | 5/2022 | Sato et al. |
| 2022/0135965 | A1 | 5/2022 | Gantt et al. |
| 2022/0145289 | A1 | 5/2022 | Lackey et al. |
| 2022/0206001 | A1 | 6/2022 | Sato |
| 2022/0243195 | A1 | 8/2022 | Nugent et al. |
| 2022/0246236 | A1 | 8/2022 | Amirav-Drory |
| 2022/0259319 | A1 | 8/2022 | Sato et al. |
| 2022/0259638 | A1 | 8/2022 | Brown |
| 2022/0277808 | A1 | 9/2022 | Arbiza et al. |
| 2022/0281989 | A1 | 9/2022 | Glanville |
| 2022/0307010 | A1 | 9/2022 | Sato et al. |
| 2022/0315971 | A1 | 10/2022 | Wu et al. |
| 2022/0323924 | A1 | 10/2022 | Lackey et al. |
| 2022/0325276 | A2 | 10/2022 | Banyai et al. |
| 2022/0325278 | A1 | 10/2022 | Nugent et al. |
| 2022/0348659 | A1 | 11/2022 | Sato et al. |
| 2022/0356463 | A1 | 11/2022 | Shen et al. |
| 2022/0356468 | A1 | 11/2022 | Sato et al. |
| 2022/0411784 | A1 | 12/2022 | Sato et al. |
| 2023/0002478 | A1 | 1/2023 | Sato et al. |
| 2023/0054232 | A1 | 2/2023 | Peck |
| 2023/0086062 | A1 | 3/2023 | Banyai et al. |
| 2023/0096464 | A1 | 3/2023 | Sato |
| 2023/0115861 | A1 | 4/2023 | Nugent et al. |
| 2023/0153452 | A1 | 5/2023 | Peck et al. |
| 2023/0158469 | A1 | 5/2023 | Lackey et al. |
| 2023/0175062 | A1 | 6/2023 | Lackey et al. |
| 2023/0185971 | A1 | 6/2023 | Peck |
| 2023/0192818 | A1 | 6/2023 | Sato et al. |
| 2023/0192819 | A1 | 6/2023 | Sato et al. |
| 2023/0193383 | A1 | 6/2023 | Peck |
| 2023/0193513 | A1 | 6/2023 | Tabibiazar et al. |
| 2023/0211308 | A1 | 7/2023 | Banyai et al. |

FOREIGN PATENT DOCUMENTS

| | | | |
|---|---|---|---|
| JP | H07505530 | A | 6/1995 |
| JP | 2001518086 | A | 10/2001 |
| JP | 2002538790 | A | 11/2002 |
| JP | 2004268394 | A | 9/2004 |
| JP | 2006503586 | A | 2/2006 |
| JP | 2007314746 | A | 12/2007 |
| JP | 2008214343 | A | 9/2008 |

(56) References Cited

FOREIGN PATENT DOCUMENTS

| | | | |
|---|---|---|---|
| JP | 2009294195 A | 12/2009 |
| JP | 2012507513 A | 3/2012 |
| JP | 2016527313 A | 9/2016 |
| WO | WO-9320242 A1 | 10/1993 |
| WO | 9831838 A1 | 7/1998 |
| WO | WO-02072791 A2 | 9/2002 |
| WO | WO-2004039953 A2 | 5/2004 |
| WO | WO-2005059096 A2 | 6/2005 |
| WO | WO-2008054543 A2 | 5/2008 |
| WO | WO-2008063135 A1 | 5/2008 |
| WO | WO-2010053443 A1 | 5/2010 |
| WO | WO-2011109031 A1 | 9/2011 |
| WO | WO-2012078312 A2 | 6/2012 |
| WO | WO-2012154201 A1 | 11/2012 |
| WO | WO-2014021938 A1 | 2/2014 |
| WO | WO-2015021080 A2 | 2/2015 |
| WO | WO-2022010934 A1 | 1/2022 |
| WO | WO-2022076326 A1 | 4/2022 |
| WO | WO-2022086866 A1 | 4/2022 |
| WO | WO-2022087293 A1 | 4/2022 |
| WO | WO-2022098662 A2 | 5/2022 |
| WO | WO-2022159620 A1 | 7/2022 |
| WO | WO-2022178137 A1 | 8/2022 |
| WO | WO-2022204309 A1 | 9/2022 |
| WO | WO-2022204316 A2 | 9/2022 |
| WO | WO-2022217004 A1 | 10/2022 |
| WO | WO-2022235579 A1 | 11/2022 |
| WO | WO-2022235584 A1 | 11/2022 |
| WO | WO-2022271884 A2 | 12/2022 |
| WO | WO-2023023183 A2 | 2/2023 |
| WO | WO-2023023190 A2 | 2/2023 |
| WO | WO-2023023285 A2 | 2/2023 |
| WO | WO-2023069367 A1 | 4/2023 |
| WO | WO-2023076419 A2 | 5/2023 |
| WO | WO-2023076420 A2 | 5/2023 |
| WO | WO-2023076687 A1 | 5/2023 |
| WO | WO-2023091609 A2 | 5/2023 |
| WO | WO-2023091614 A2 | 5/2023 |
| WO | WO-2023102034 A2 | 6/2023 |
| WO | WO2023114432 A2 | 6/2023 |

OTHER PUBLICATIONS

ATDBio. Solid-Phase Oligonucleotide Synthesis, Nucleic Acids Book, 20 pages, Published on Jul. 31, 2011. from: http://www. atdbio.com/content/17/Solid-phase-oligonucleotide-synthesis.
Berg: Biochemistry. 5th ED. New York (2002) 148-149.
Blanchard et al.: High-Density Oligonucleotide Arrays. Biosensors & Bioelectronics, 11(6/7):687-690 (1996).
Buermans et al.: Next Generation sequencing technology: Advances and applications, Biochimica et Biophysica Acta (BBA)—Molecular Basis of Disease, 1842:1931-1941 (2014).
Cheng et al.: High throughput parallel synthesis of oligonucleotides with 1536 channel synthesizer. Nucleic Acids Res. 30(18):e93 (2002).
Cleary et al.: Production of complex nucleic acid libraries using highly parallel in situ oligonucleotide synthesis. Nat Methods. 1(3):241-248 (2004).
Cohen et al.: Human population: The next half century. Science. 302:1172-1175 (2003).
Cruse et al.: Atlas of Immunology. Third Edition. Boca Raton:CRC Press (pp. 282-283) (2010).
Elsik et al.: The Genome sequence of taurine cattle: A window of ruminant biology and evolution. Science. 324:522-528 (2009).
Fodor et al.: Light-directed, spatially addressable parallel chemical synthesis. Science. 251(4995):767-773 (1991).
Gao et al.: A method for the generation of combinatorial antibody libraries using pIX phage display. PNAS 99(20):12612-12616 (2002).
GE Healthcare. AKTA oligopilot plus. Data File 18-114-66 ADC. 8 pages (2006).
GE Healthcare. Robust and cost-efficient oligonucleotide synthesis. Application Note 28-4058-08 AA. 4 pages (2005).

Gibson et al.: Creation of a Bacterial Cell Controlled by A Chemically Synthesized Genome. Science. 329(5989):52-56 (2010).
Hasin-Brumshtein et al.: The Effects of Mismatches on DNA Capture by Hybridization. Twist WhitePaper. 6 pages (May 7, 2019).
Hudson: Matrix Assisted Synthetic Transformations: A Mosaic of Diverse Contributions. Journal of Combinatorial Chemistry. 1(6):403-457 (1999).
Karlin et al.: Methods for assessing the statistical significance of molecular sequence features by using general scoring schemes. Proc. Natl. Acad. Sci. 87: 2264-2268 (1990).
Karlin et al.: Applications and statistics for multiple high-scoring segments in molecular sequences. PNAS USA 90(12):5873-5787 (1993).
Kong et al.: Parallel gene synthesis in a microfluidic device. Nucleic Acids Res. 35(8):e61 (2007).
Kosuri and Church. Large-scale de novo DNA synthesis: technologies and applications. Nature Methods. 11:499-507 (2014) Available at: http://www.nature.com/nmeth/journal/v11/n5/full/nmeth. 2918.html.
Kosuri et al.: A scalable gene synthesis by selective amplification of DNA pools from high-fidelity microchips. Nature Biotechnology. 28:1295-1299 (2010).
Kosuri et al.: A scalable gene synthesis platform using high-fidelity DNA microchips Nat.Biotechnol. 28(12):1295-1299 (2010).
Krayden, Inc.: A Guide to Silane Solutions. Silane coupling agents. 7 pages. Published on May 31, 2005 at: http://krayden.com/pdf/ xia_silane_chemistry.pdf.
Lausted et al.: POSaM: a fast, flexible, open-source, inkjet oligonucleotide synthesizer and microarrayer. Genome Biology. 5:R58, 17 pages (2004) available at https://www.ncbi.nlm.nih.gov/pmc/ articles/PMC507883/.
Lebl et al.: Economical Parallel Oligonucleotide and Peptide Synthesizer—Pet Oligator. Int. J. Peptide Res. Ther. 13(1-2):367-376 (2007).
Leproust et al.: Synthesis of high-quality libraries of long (150mer) oligonucleotides by a novel depurination controlled process. Nucleic Acids Research. 38(8):2522-2540 (2010).
Lewontin and Harti, Population genetics in forensic DNA typing. Science, 254:1745-1750, 1991.
Ma et al.: DNA synthesis, assembly and application in synthetic biology. Current Opinion in Chemical Biology. 16:260-267 (2012).
Ma et al.: Versatile surface functionalization of cyclic olefin copolymer (COC) with sputtered SiO2 thin film for potential BioMEMS applications. Journal of Materials Chemistry. 11 pages (2009).
Mazor et al.: Isolation of Full-Length IgG Antibodies from Combinatorial Libraries Expressed in Escherichia coli; Antony S. Dimitrov (ed.), Therapeutic Antibodies: Methods and Protocols, vol. 525, Chapter 11, pp. 217-239 (2009).
McBride & Caruthers. An investigation of several deoxynucleoside phosphoramidites useful for synthesizing deoxyoligonucleotides. Tetrahedron Lett. 24:245-248 (1983).
Mitra et al.: In situ localized amplification and contact replication of many individual DNA molecules. Nucleic Acids Res. 27(24):e34 (1999).
Morin et al.: Profiling the HeLa S3 transcriptome using randomly primed cDNA and massively parallel short-read sequencing. Biotechniques. 45:81-94 (2008).
Opposition to European Patent No. 3030682 filed Mar. 3, 2021.
PCT/US2014/049834 International Preliminary Report on Patentability dated Feb. 18, 2016.
PCT/US2014/049834 International Search Report and Written Opinion mailed Mar. 19, 2015.
PCT/US2014/049834 Invitation to Pay Additional Fees mailed Jan. 5, 2015.
Pirrung. How to make a DNA chip. Angew. Chem. Int. Ed. 41:1276-1289 (2002).
Pray. Discovery of DNA Structure and Function: Watson and Crick. Nature Education.6 pages (2008) available at: http://www.nature. com/scitable/topicpage/discovery-of-dna-structure-and-function-watson-397.

(56)                  References Cited

OTHER PUBLICATIONS

Quan et al.: Parallel on-chip gene synthesis and application to optimization of protein expression. Nature Biotechnology. 29:449-452 (2011).

Rafalski and Morgante. Corn and humans: recombination and linkage disequilibrium in two genomes of similar size. Trends in Genetics. 20(2):103-111 (2004).

Rogozin et al.: Origin and evolution of spliceosomal introns. Biology Direct, 7:11 (2012).

Saaem et al.: In situ synthesis of DNA microarray on functionalized cyclic olefin copolymer substrate ACS Applied Materials & Interfaces. 2(2):491-497 (2010).

Sargolzaei et al.: Extent of linkage disequilibrium in Holstein cattle in North America. J.Dairy Science. 91:2106-2117 (2007).

Srivannavit et al.: Design and fabrication of microwell array chips for a solution-based, photogenerated acid-catalyzed parallel oligonucleotide DNA synthesis. Sensors and Actuators A. 116:150-160 (2004).

Steel. The Flow-Thru Chip A Three-dimensional biochip platform. In: Schena, Microarray Biochip Technology, Chapter 5, Natick, MA: Eaton Publishing, 2000, 33 pages.

Taylor et al.: Impact of surface chemistry and blocking strategies on DNA microarrays. Nucleic Acids Research, 31(16):e87 19 pages (2003).

Tian et al.: Accurate multiplex gene synthesis from programmable DNA microchips. Nature. 432(7020):1050-1054 (2004).

U.S. Appl. No. 14/452,429 Notice of Allowance dated Jun. 7, 2016.

U.S. Appl. No. 14/452,429 Office Action mailed Apr. 9, 2015.

U.S. Appl. No. 14/452,429 Office Action mailed Oct. 21, 2015.

U.S. Appl. No. 14/452,429 Restriction Requirement mailed Dec. 12, 2014.

U.S. Appl. No. 14/885,962 Notice of Allowance dated Nov. 8, 2017 and Sep. 29, 2017.

U.S. Appl. No. 14/885,962 Office Action dated Dec. 16, 2016.

U.S. Appl. No. 14/885,962 Office Action dated Sep. 8, 2016.

U.S. Appl. No. 14/885,962 Restriction Requirement dated Mar. 1, 2016.

U.S. Appl. No. 14/885,963 Notice of Allowance dated May 24, 2016.

U.S. Appl. No. 14/885,963 Office Action dated Feb. 5, 2016.

U.S. Appl. No. 14/885,965 Office Action dated Aug. 28, 2018.

U.S. Appl. No. 14/885,965 Office Action dated Aug. 30, 2017.

U.S. Appl. No. 14/885,965 Office Action dated Feb. 10, 2017.

U.S. Appl. No. 14/885,965 Office Action dated Feb. 18, 2016.

U.S. Appl. No. 14/885,965 Office Action dated Jan. 4, 2018.

U.S. Appl. No. 14/885,965 Office Action dated Jul. 7, 2016.

U.S. Appl. No. 15/187,714 Final Office Action dated Sep. 17, 2019.

U.S. Appl. No. 15/187,714 Office Action dated Apr. 4, 2019.

U.S. Appl. No. 15/187,714 Restriction Requirement dated Sep. 17, 2018.

U.S. Appl. No. 15/187,721 Notice of Allowance dated Dec. 7, 2016.

U.S. Appl. No. 15/187,721 Office Action dated Oct. 14, 2016.

U.S. Appl. No. 15/233,835 Notice of Allowance dated Oct. 4, 2017.

U.S. Appl. No. 15/233,835 Office Action dated Feb. 8, 2017.

U.S. Appl. No. 15/233,835 Office Action dated Jul. 26, 2017.

U.S. Appl. No. 15/233,835 Restriction Requirement dated Nov. 4, 2016.

U.S. Appl. No. 15/245,054 Notice of Allowance dated Dec. 14, 2017.

U.S. Appl. No. 15/245,054 Office Action dated Mar. 21, 2017.

U.S. Appl. No. 15/245,054 Office Action dated Oct. 19, 2016.

U.S. Appl. No. 15/377,547 Final Office Action dated Feb. 8, 2019.

U.S. Appl. No. 15/377,547 Office Action dated Jul. 27, 2018.

U.S. Appl. No. 15/377,547 Office Action dated Mar. 24, 2017.

U.S. Appl. No. 15/377,547 Office Action dated Nov. 30, 2017.

U.S. Appl. No. 15/602,991 Final Office Action dated Dec. 13, 2018.

U.S. Appl. No. 15/602,991 Notice of Allowance dated Oct. 25, 2017.

U.S. Appl. No. 15/602,991 Office Action dated May 31, 2018.

U.S. Appl. No. 15/602,991 Office Action dated May 31, 2019.

U.S. Appl. No. 15/602,991 Office Action dated Sep. 21, 2017.

U.S. Appl. No. 15/603,013 Final Office Action dated Nov. 6, 2019.

U.S. Appl. No. 15/603,013 Office Action dated Jan. 30, 2018.

U.S. Appl. No. 15/603,013 Office Action dated Jul. 10, 2018.

U.S. Appl. No. 15/603,013 Office Action dated Jun. 26, 2019.

U.S. Appl. No. 15/603,013 Office Action dated Oct. 20, 2017.

U.S. Appl. No. 15/729,564 Final Office Action dated Dec. 13, 2018.

U.S. Appl. No. 15/729,564 Office Action dated Jan. 8, 2018.

U.S. Appl. No. 15/729,564 Office Action dated Jun. 6, 2018.

U.S. Appl. No. 15/729,564 Office Action dated May 30, 2019.

U.S. Appl. No. 15/991,992 Office Action dated May 21, 2020.

U.S. Appl. No. 15/991,992 Restriction Requirement dated Mar. 10, 2020.

U.S. Appl. No. 16/039,256 Final Office Action dated Mar. 30, 2021.

U.S. Appl. No. 16/039,256 Office Action dated Aug. 20, 2020.

U.S. Appl. No. 16/039,256 Office Action dated May 10, 2022.

U.S. Appl. No. 16/039,256 Restriction Requirement dated May 18, 2020.

U.S. Appl. No. 16/409,608 Office Action dated Sep. 9, 2019.

U.S. Appl. No. 16/535,777 Final Office Action dated Oct. 20, 2020.

U.S. Appl. No. 16/535,777 Office Action dated Feb. 8, 2021.

U.S. Appl. No. 16/535,777 Office Action dated Jan. 23, 2020.

U.S. Appl. No. 16/535,779 First Action Interview dated Feb. 10, 2020.

U.S. Appl. No. 16/737,401 Final Office Action dated Jun. 13, 2022.

U.S. Appl. No. 16/737,401 Office Action dated Jan. 5, 2022.

U.S. Appl. No. 16/737,401 Restriction Requirement dated Nov. 15, 2021.

Van Tassell et al.: SNP discovery and allele frequency estimation by deep sequencing of reduced representation libraries. Nature Methods. 5:247-252 (2008).

Wootton et al. Statistics of local complexity in amino acid sequences and sequence databases. Computers & Chemistry 17(2):149-163 (Jun. 1993).

Xu et al.: Design of 240,000 orthogonal 25mer DNA barcode probes. PNAS. 106(7):2289-2294 (2009).

Cheng, A., "Sharpening new scissors: Designing a CRISPR-Cas9 construct for inducible and interchangeable HSATII expression in Tig-1 fibroblasts" Swarthmore College. Retrieved From The Internet On Aug. 1, 2023: URL: https://works.swarthmore.edu/theses/166/ 2021; abstract; p. 14, 3rd paragraph.

International Search Report and Written Opinion for International Application No. PCT/US2023/014651, mailed on Sep. 7, 2023.

Pryor J.M., et al., "Enabling one-pot Golden Gate assemblies of unprecedented complexity using data optimized assembly design" PLoS One. Sep. 2020; Abstract; p. 3, 2nd paragraph; DOI: 10.13711journal.pone.0238592.

FIG. 4

Histogram of Normalized ReadCounts Z1

Histogram of Normalized ReadCounts Z1

Histogram of Normalized ReadCounts Z1

Histogram of Normalized ReadCounts Z1

Histogram of Normalized ReadCounts Z1

METHYLATION-MEDIATED ADAPTER REMOVAL ON NUCLEIC ACID SEQUENCES

CROSS REFERENCE

This application claims the benefit of U.S. Provisional Patent Application No. 63/317,466, filed on Mar. 7, 2022, which is incorporated herein by reference in its entirety.

SEQUENCE LISTING

The instant application contains a Sequence Listing which has been submitted electronically in XML format and is hereby incorporated by reference in its entirety. Said XML copy, created on Mar. 29, 2023, is named 44854-807_201_SL.xml and is 3,745 bytes in size.

BACKGROUND

Restriction enzymes or restriction endonucleases are enzymes that cleave DNA into fragments at recognition sites known as restriction sites. Restriction enzymes, generally found in bacteria and archaea, provide an innate immune response that cleaves foreign DNA via restriction digestion. Since restriction enzymes cut specific DNA sequences, bacteria must protect their own DNA against cutting. This protection is achieved by methylating sites in the host DNA using enzymes known as methyl-transferases. Methylated DNA sequences are protected from digestion by their cognate restriction enzyme.

This property of restriction enzymes can be utilized to control their activity. While restriction endonucleases are commonly used in molecular biology to generate sticky-ends for cloning of DNA fragments, the usage of sticky ends has been limited to the presence of internal and unwanted recognition sites in the DNA sequence of interest. Scientists routinely inspect sequences of interest to avoid using restriction enzymes that will cut at unwanted locations. Existing methods to deal with these problems include using alternative restriction enzymes that have recognition sites not present in the DNA of interest, or modifying DNA (e.g. via codon optimization) to remove internal recognition sites.

Disclosed herein is a sequence agnostic method of DNA assembly or DNA adaptor removal that is insensitive to the presence of unwanted internal recognition sites elsewhere in the DNA of interest.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF SUMMARY

Provided herein are methods for nucleic acid assembly.

Provided herein are methods for nucleic acid assembly, comprising: (a) providing a plurality of polynucleotides, wherein each of the polynucleotides comprises a 5' adapter sequence comprising at least one Type IIS endonuclease site or a 3' adapter sequence comprising at least one Type IIS endonuclease site; (b) amplifying the plurality of polynucleotides using a reaction mixture comprising about 5% to about 100% modified bases; and (c) mixing the plurality of polynucleotides with a Type IIS restriction enzyme to generate a plurality of nucleic acids. In some embodiments, the modified bases comprise methyl-dCTP. In some embodiments, the reaction mixture comprises about 10% to about 50% methyl-dCTP. In some embodiments, the reaction mixture comprises about 20% to about 40% methyl-dCTP. In some embodiments, the Type IIS restriction enzyme is selected from the group consisting of AcuI, AlwI, BaeI, BbsI, BbvI, BccI, BceAI, BcgI, BciVI, BcoDI, BfuAI, BmrI, BpmI, BpuEI, BsaI, BsaXI, BseRI, BsgI, BsmAI, BsmBI, BsmFI, BsmI, BspCNI, BspMI, BspQI, BsrDI, BsrI, BtgZI, BtsCI, BtsI, BtsIMutI, CspCI, EarI, EciI, Esp3I, FauI, FokI, HgaI, HphI, HpyAV, MboII, MlyI, MmeI, MnlI, NmeAIII, PleI, SapI, and SfaNI. In some embodiments, the Type IIS restriction enzyme is BsmBI. In some embodiments, the plurality of polynucleotides comprises up to 100 different sequences. In some embodiments, the plurality of polynucleotides comprises up to 1000 different sequences. In some embodiments, the plurality of polynucleotides comprises up to 10,000 different sequences. In some embodiments, the plurality of polynucleotides comprises up to 100,000 different sequences. In some embodiments, the plurality of nucleic acids comprises at least 10,000 nucleic acids. In some embodiments, the plurality of nucleic acids comprises at least 100,000 nucleic acids. In some embodiments, at least 80% of the plurality of nucleic acids are represented within 2× of a mean frequency. In some embodiments, at least 90% of the plurality of nucleic acids are represented within 2× of a mean frequency. In some embodiments, at least 80% of the plurality of nucleic acids are represented within 1.5× of a mean frequency. In some embodiments, at least 90% of the plurality of nucleic acids are represented within 1.5× of a mean frequency. In some embodiments, the method further comprises assembling one or more nucleic acids. In some embodiments, the method further comprises assembling one or more nucleic acids using a plurality of overlaps. In some embodiments, the method further comprises ligating the nucleic acids. In some embodiments, the method further comprises ligating the nucleic acids to a vector. In some embodiments, the method further comprises transformation of the vector.

Provided herein are methods for nucleic acid assembly, comprising: (a) providing a plurality of polynucleotides, wherein each of the polynucleotides comprises a 5' adapter sequence comprising at least one Type IIS endonuclease site and a 3' adapter sequence comprising at least one Type IIS endonuclease site; (b) amplifying the plurality of polynucleotides using a reaction mixture comprising about 5% to about 100% modified bases; and (c) mixing the plurality of polynucleotides with a Type IIS restriction enzyme to generate a plurality of nucleic acids. In some embodiments, the modified bases comprise methyl-dCTP. In some embodiments, the reaction mixture comprises about 10% to about 50% methyl-dCTP. In some embodiments, the reaction mixture comprises about 20% to about 40% methyl-dCTP. In some embodiments, the Type IIS restriction enzyme is selected from the group consisting of AcuI, AlwI, BaeI, BbsI, BbvI, BccI, BceAI, BcgI, BciVI, BcoDI, BfuAI, BmrI, BpmI, BpuEI, BsaI, BsaXI, BseRI, BsgI, BsmAI, BsmBI, BsmFI, BsmI, BspCNI, BspMI, BspQI, BsrDI, BsrI, BtgZI, BtsCI, BtsI, BtsIMutI, CspCI, EarI, EciI, Esp3I, FauI, FokI, HgaI, HphI, HpyAV, MboII, MlyI, MmeI, MnlI, NmeAIII, PleI, SapI, and SfaNI. In some embodiments, the Type IIS restriction enzyme is BsmBI. In some embodiments, the plurality of polynucleotides comprises up to 100 different sequences. In some embodiments, the plurality of polynucleotides comprises up to 1000 different sequences. In some embodiments, the plurality of polynucleotides comprises up to 10,000 different sequences. In some embodiments, the plurality of polynucleotides comprises up to 100,000 different sequences. In some embodiments, the plurality of nucleic acids comprises at least 10,000 nucleic acids. In some embodiments, the plurality of nucleic acids comprises at least 100,000 nucleic acids. In some embodiments, at least 80% of the plurality of nucleic acids are represented within 2× of a mean frequency. In some embodiments, at least 90% of the plurality of nucleic acids are represented within 2× of a mean frequency. In some embodiments, at least 80% of the plurality of nucleic acids are represented within 1.5× of a mean frequency. In some embodiments, at least 90% of the plurality of nucleic acids are represented within 1.5× of a mean frequency. In some embodiments, the method further comprises assembling one or more nucleic acids. In some embodiments, the method further comprises assembling one or more nucleic acids using a plurality of overlaps. In some embodiments, the method further comprises ligating the nucleic acids. In some embodiments, the method further comprises ligating the nucleic acids to a vector. In some embodiments, the method further comprises transformation of the vector.

Provided herein are methods for adapter removal, comprising: (a) providing a plurality of polynucleotides encoding a gene comprising one or more modifications associated with a disease or disorder, wherein each of the polynucleotides comprises a 5' adapter sequence comprising a Type IIS endonuclease site or a 3' adapter sequence comprising a Type IIS endonuclease site; (b) amplifying the plurality of polynucleotides using a reaction mixture comprising about 5% to about 100% modified bases; and (c) mixing the plurality of polynucleotides with a Type IIS restriction enzyme to generate a plurality of nucleic acids. In some embodiments, the disease or disorder is cancer. In some embodiments, the modified bases comprise methyl-dCTP. In some embodiments, the reaction mixture comprising about 10% to about 50% methyl-dCTP. In some embodiments, the reaction mixture comprising about 20% to about 40% methyl-dCTP. In some embodiments, the Type IIS restriction enzyme is selected from the group consisting of AcuI, AlwI, BaeI, BbsI, BbvI, BccI, BceAI, Bcgl, BciVI, BcoDI, BfuAI, BmrI, BpmI, BpuEI, BsaI, BsaXI, BseRI, BsgI, BsmAI, BsmBI, BsmFI, BsmI, BspCNI, BspMI, BspQI, BsrDI, BsrI, BtgZI, BtsCI, BtsI, BtsIMutI, CspCI, EarI, EciI, Esp3I, FauI, FokI, HgaI, HphI, HpyAV, MboII, MlyI, MmeI, MnlI, NmeAIII, PleI, SapI, and SfaNI. In some embodiments, the Type IIS restriction enzyme is BsmBI. In some embodiments, the plurality of polynucleotides comprises up to 100 different sequences. In some embodiments, the plurality of polynucleotides comprises up to 1000 different sequences. In some embodiments, the plurality of polynucleotides comprises up to 10,000 different sequences. In some embodiments, the plurality of polynucleotides comprises up to 100,000 different sequences. In some embodiments, the plurality of nucleic acids comprises at least 10,000 nucleic acids. In some embodiments, the plurality of nucleic acids comprises at least 100,000 nucleic acids. In some embodiments, at least 80% of the plurality of nucleic acids are represented within 2× of a mean frequency. In some embodiments, at least 90% of the plurality of nucleic acids are represented within 2× of a mean frequency. In some embodiments, at least 80% of the plurality of nucleic acids are represented within 1.5× of a mean frequency. In some embodiments, at least 90% of the plurality of nucleic acids are represented within 1.5× of a mean frequency. In some embodiments, the method further comprises assembling one or more nucleic acids. In some embodiments, the method further comprises assembling one or more nucleic acids using a plurality of overlaps. In some embodiments, the method further comprises ligating the nucleic acids. In some embodiments, the method further comprises ligating the nucleic acids to a vector. In some embodiments, the method further comprises transformation of the vector.

Provided herein are methods for adapter removal, comprising: (a) providing a plurality of polynucleotides encoding a gene comprising one or more modifications associated with a disease or disorder, wherein each of the polynucleotides comprises a 5' adapter sequence comprising a Type IIS endonuclease site and a 3' adapter sequence comprising a Type IIS endonuclease site; (b) amplifying the plurality of polynucleotides using a reaction mixture comprising about 5% to about 100% modified bases; and (c) mixing the plurality of polynucleotides with a Type IIS restriction enzyme to generate a plurality of nucleic acids. In some embodiments, the disease or disorder is cancer. In some embodiments, the modified bases comprise methyl-dCTP. In some embodiments, the reaction mixture comprising about 10% to about 50% methyl-dCTP. In some embodiments, the reaction mixture comprising about 20% to about 40% methyl-dCTP. In some embodiments, the Type IIS restriction enzyme is selected from the group consisting of AcuI, AlwI, BaeI, BbsI, BbvI, BccI, BceAI, Bcgl, BciVI, BcoDI, BfuAI, BmrI, BpmI, BpuEI, BsaI, BsaXI, BseRI, BsgI, BsmAI, BsmBI, BsmFI, BsmI, BspCNI, BspMI, BspQI, BsrDI, BsrI, BtgZI, BtsCI, BtsI, BtsIMutI, CspCI, EarI, EciI, Esp3I, FauI, FokI, HgaI, HphI, HpyAV, MboII, MlyI, MmeI, MnlI, NmeAIII, PleI, SapI, and SfaNI. In some embodiments, the Type IIS restriction enzyme is BsmBI. In some embodiments, the plurality of polynucleotides comprises up to 100 different sequences. In some embodiments, the plurality of polynucleotides comprises up to 1000 different sequences. In some embodiments, the plurality of polynucleotides comprises up to 10,000 different sequences. In some embodiments, the plurality of polynucleotides comprises up to 100,000 different sequences. In some embodiments, the plurality of nucleic acids comprises at least 10,000 nucleic acids. In some embodiments, the plurality of nucleic acids comprises at least 100,000 nucleic acids. In some embodiments, at least 80% of the plurality of nucleic acids are represented within 2× of a mean frequency. In some embodiments, at least 90% of the plurality of nucleic acids are represented within 2× of a mean frequency. In some embodiments, at least 80% of the plurality of nucleic acids are represented within 1.5× of a mean frequency. In some embodiments, at least 90% of the plurality of nucleic acids are represented within 1.5× of a mean frequency. In some embodiments, the method further comprises assembling one or more nucleic acids. In some embodiments, the method further comprises assembling one or more nucleic acids using a plurality of overlaps. In some embodiments, the method further comprises ligating the nucleic acids. In some embodiments, the method further comprises ligating the nucleic acids to a vector. In some embodiments, the method further comprises transformation of the vector.

CGTCTCN/GCAGAGN;

CGTCTCN/GCAGAGN;

CGTCTCN/GCAGAGN;

CGTCTCN/GCAGAGN;

CGTCTCN/GCAGAGN;

CGTCTCN/GCAGAGN;

CGTCTCN/GCAGAGN;

CGTCTCNC/GCAGAGNG;

CGTCTCNNNC/GCAGAGNNNG;

CGTCTCN/GCAGAGN.

Figure 4:
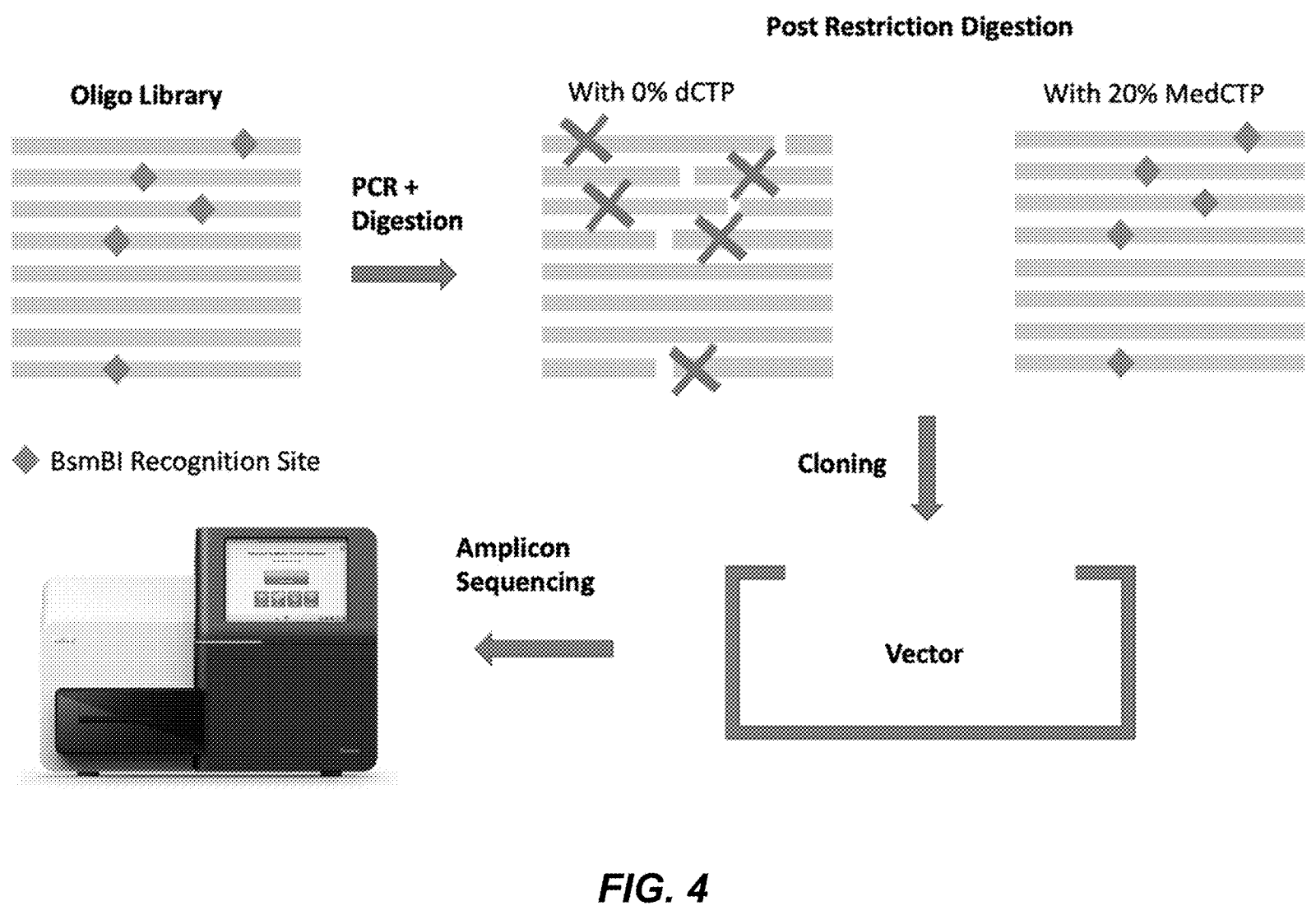

FIG. 4 depicts an exemplary workflow for cloning an oligo library containing oligos with BsmBI recognition sites. An oligo library comprising BsmBI recognition sites is subjected to PCR+digestion. Regions with 0% dCTP, all sites are cleaved, but regions with 20% Methyl dCTP, sites are preserved. The mixture is then subjected to cloning into a vector, and amplicon sequencing.

Figure 5:
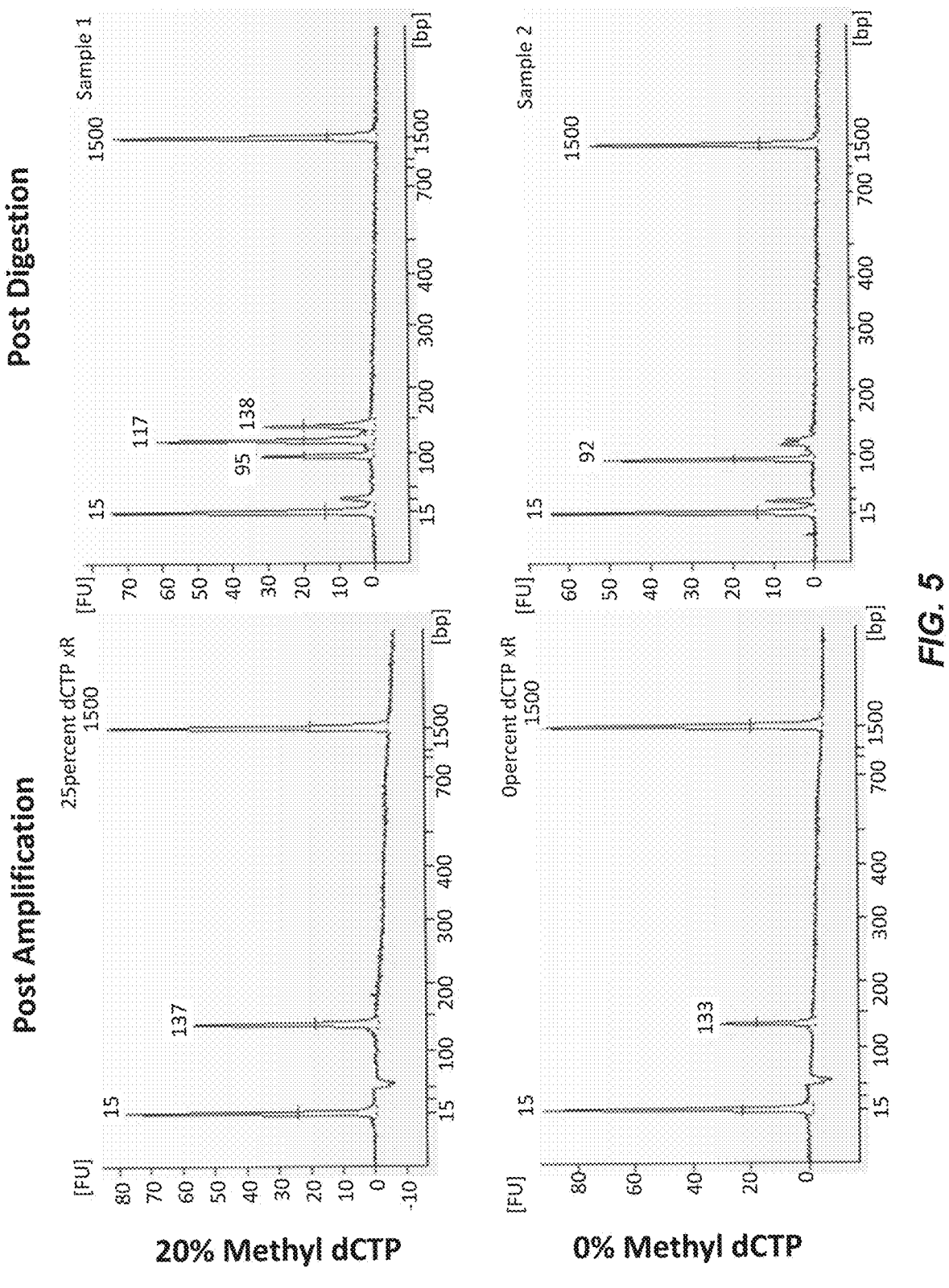

FIG. 5 depicts electropherograms showing PCR products generated with either 20% or 0% methyl dCTP against both post amplification and post digestion with BsmBI.

Figure 6:
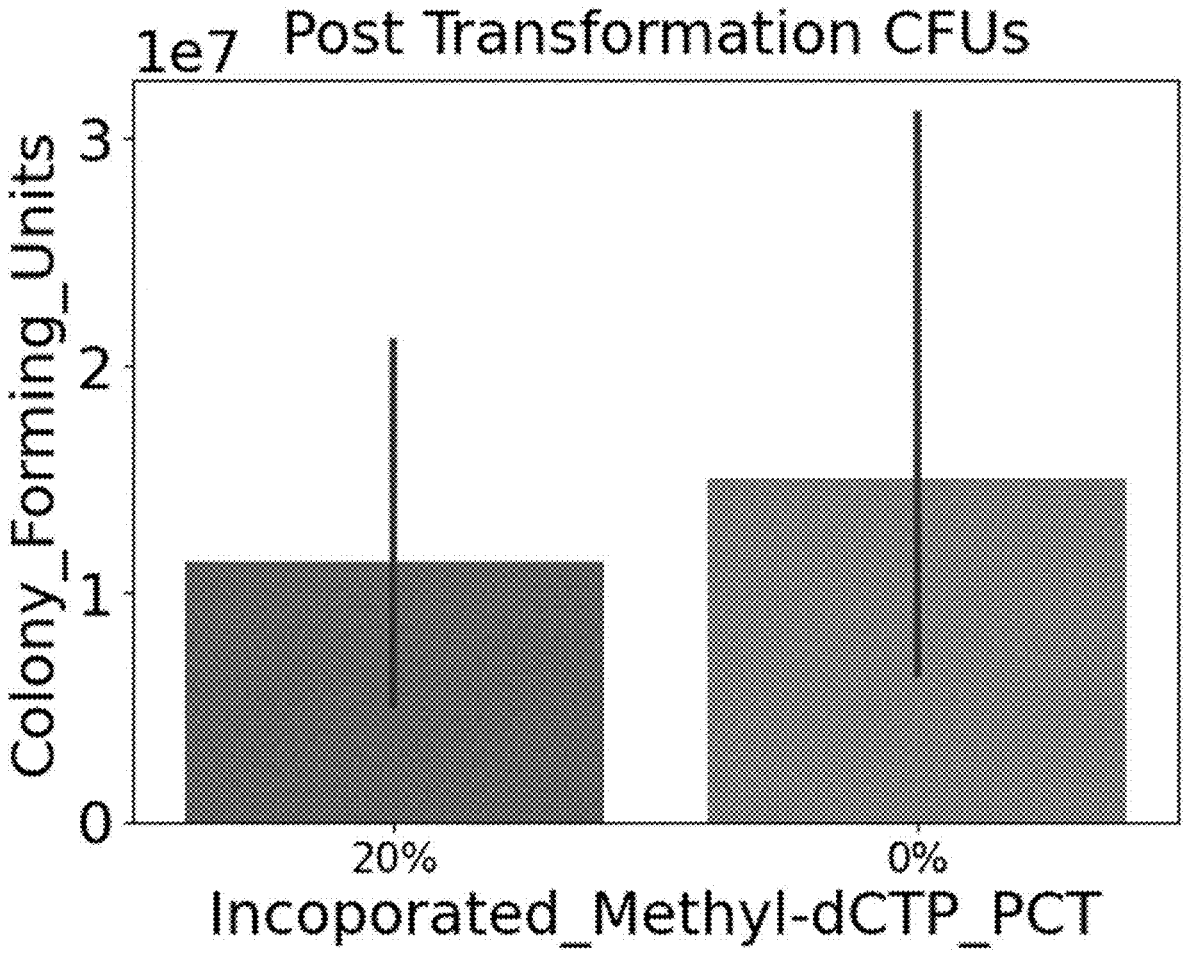

FIG. 6 depicts a plot of cloning efficacy for the amplified pool with either 20% (left bar) or 0% (right bar) Methyl dCTP. The y-axis is labeled colony forming units from 0 to $3 \times 10^7$ at $1 \times 10^7$ unit intervals.

Figure 7:
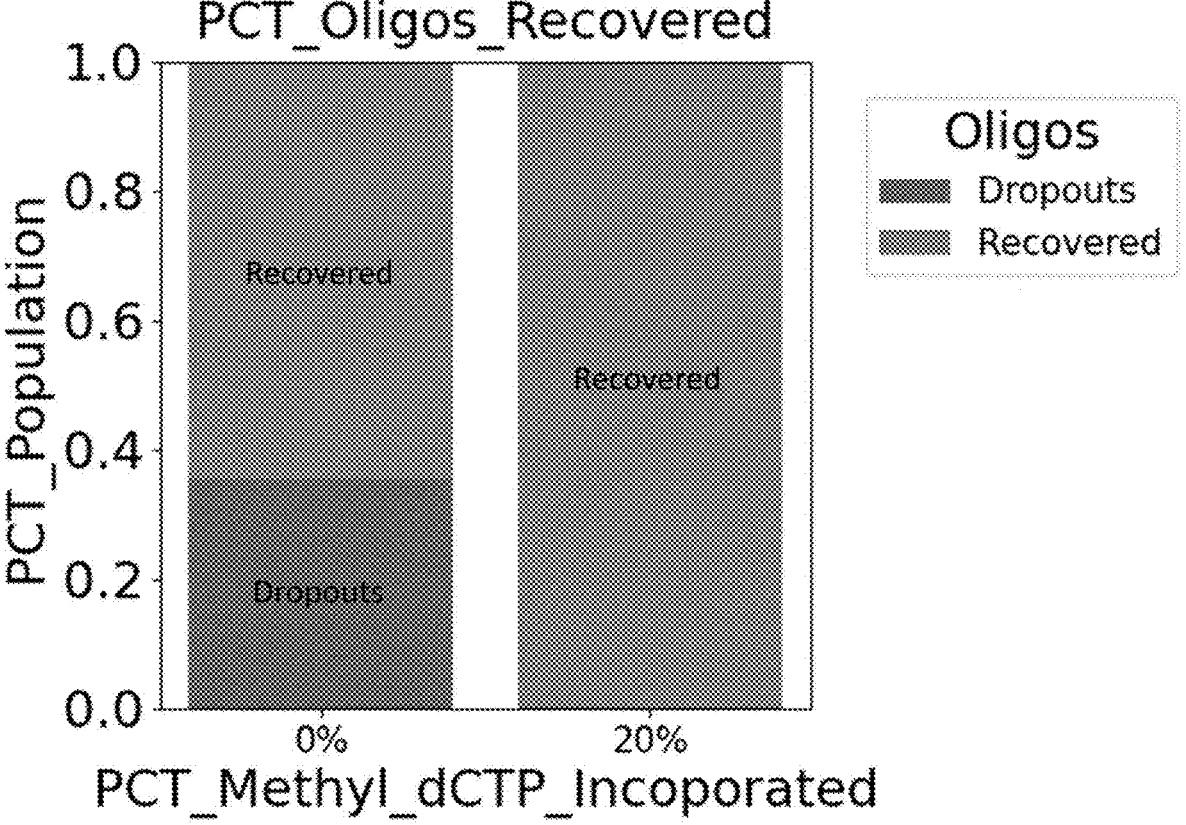

FIG. 7 depicts a plot of the proportion of oligos in the final cloned pool that contain internal BsmBI recognition sites and their representation using 0 (left bar) or 20% (right bar) methyl dCTP. The y-axis is labeled PCT_population from 0.0 to 1.0 at 0.2 unit intervals.

Figure 8A:
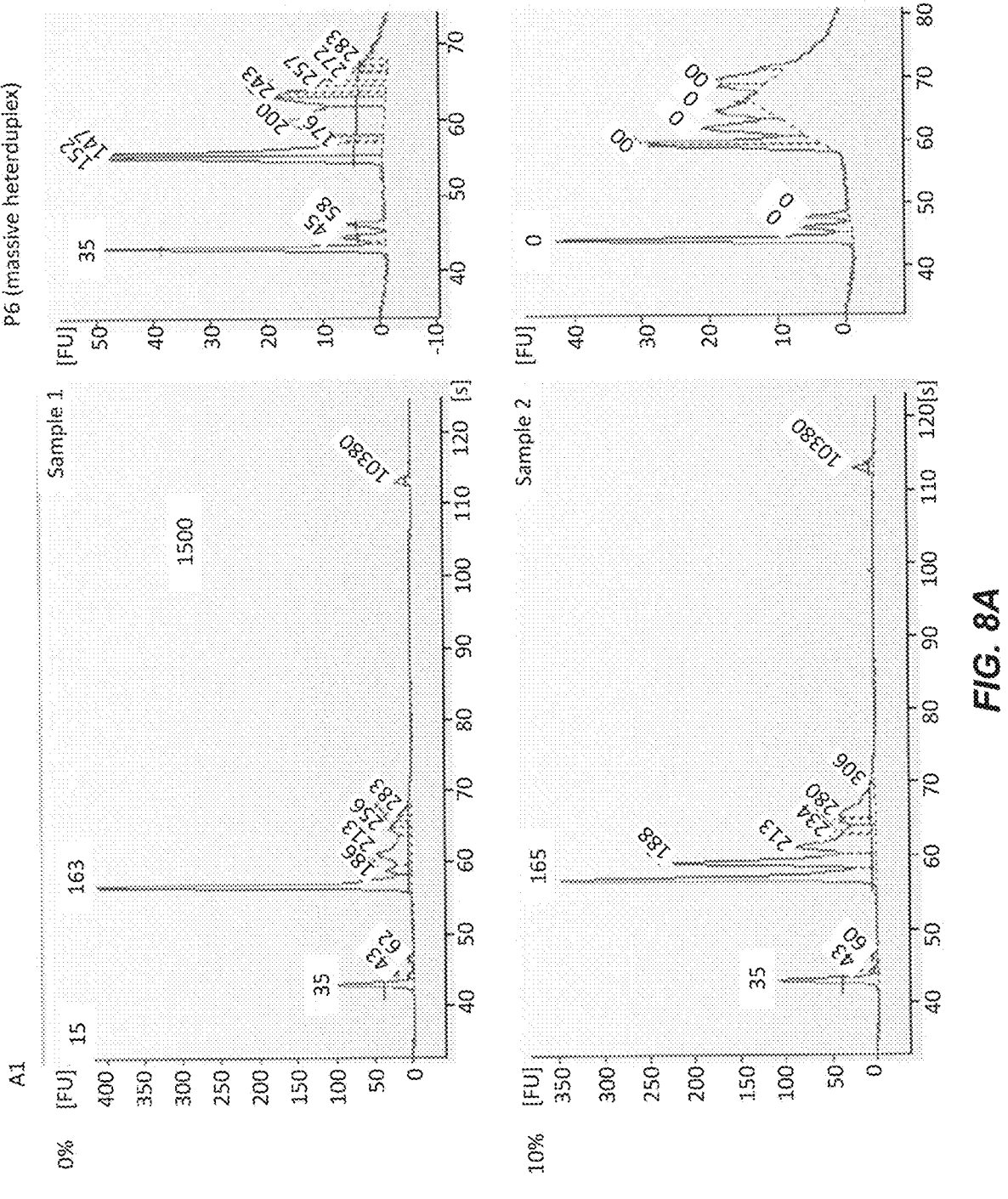
Figure 8B:
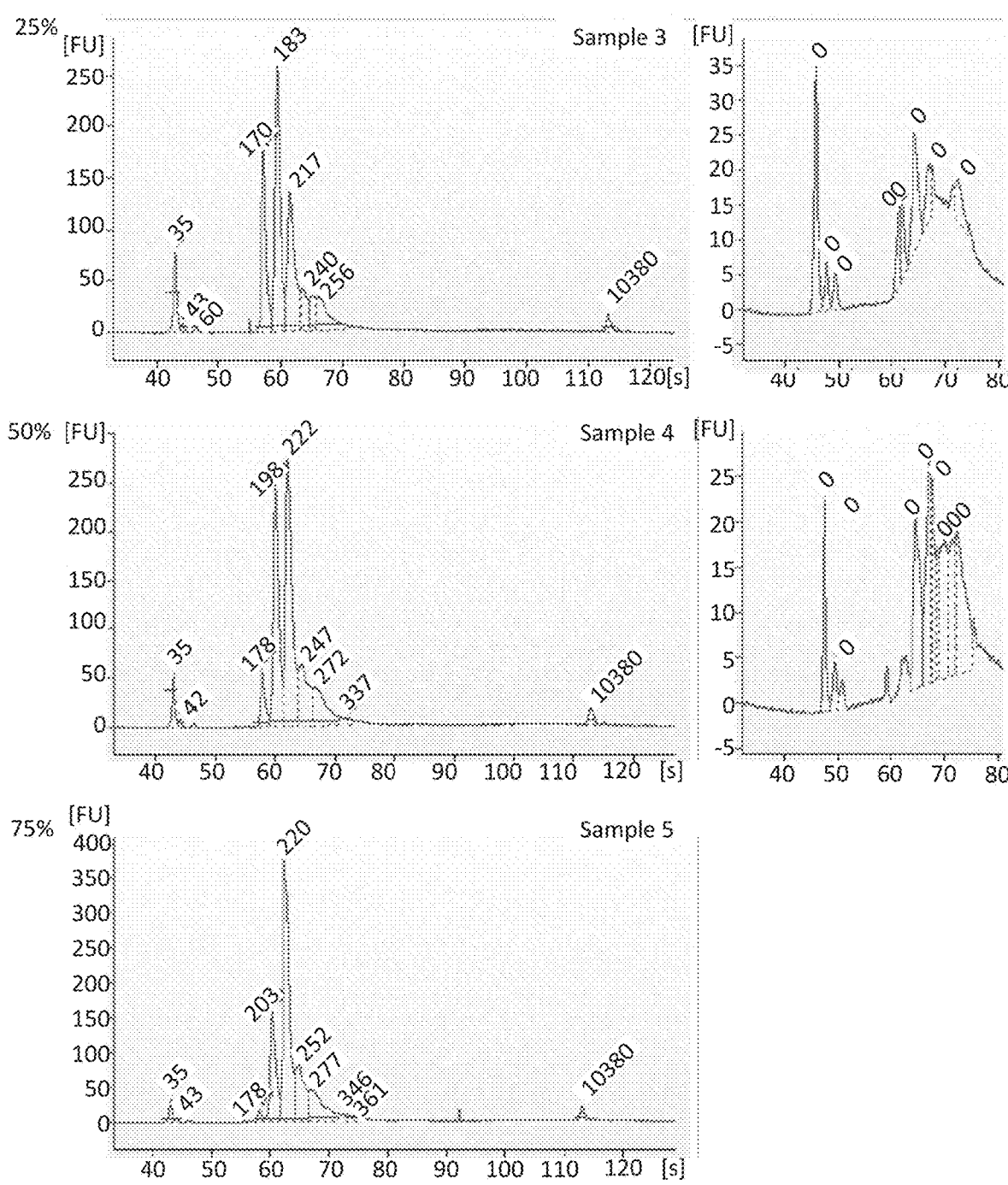
Figure 8C:
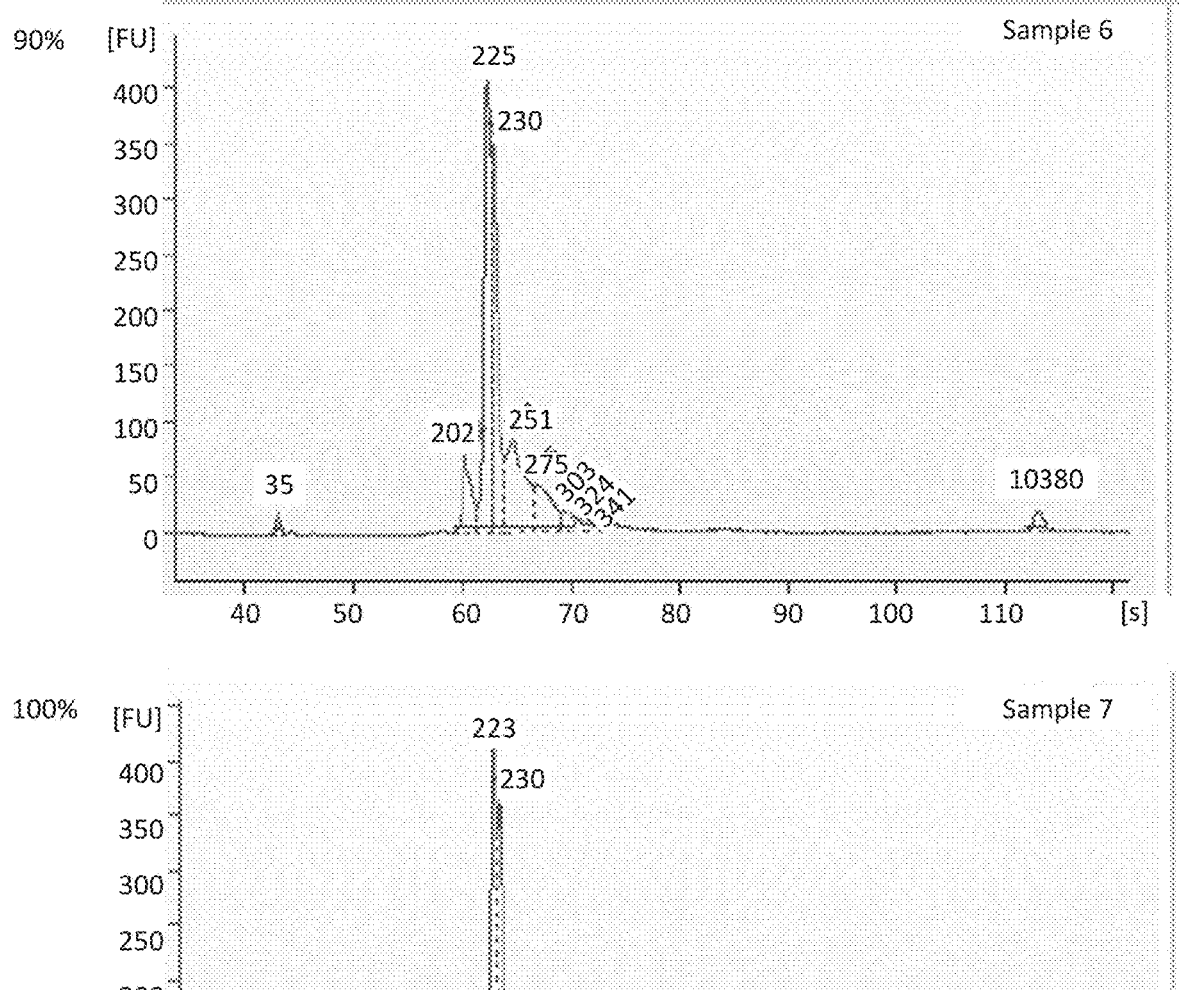

FIGS. 8A-8C depict graphs of samples prepared using various percentage of methyl-dCTP. FIG. 8A depicts 0% (top), 10% (bottom); FIG. 8B depicts 25% (top), 50% (middle); 75% (bottom); FIG. 8C depicts 90% (top); 100% (bottom).

Figure 9:
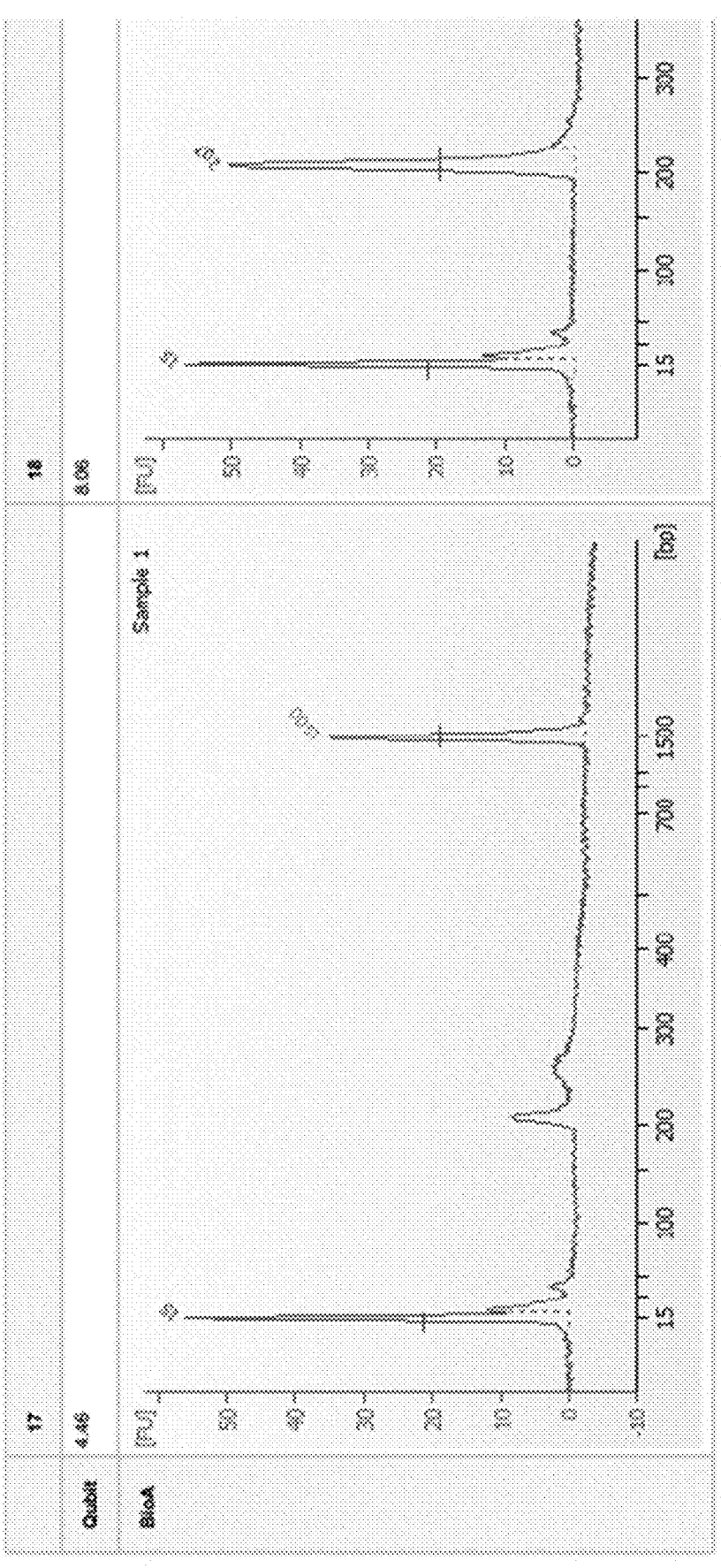

FIG. 9 depicts an electropherogram showing PCR products generated using methods described herein.

Figure 10:
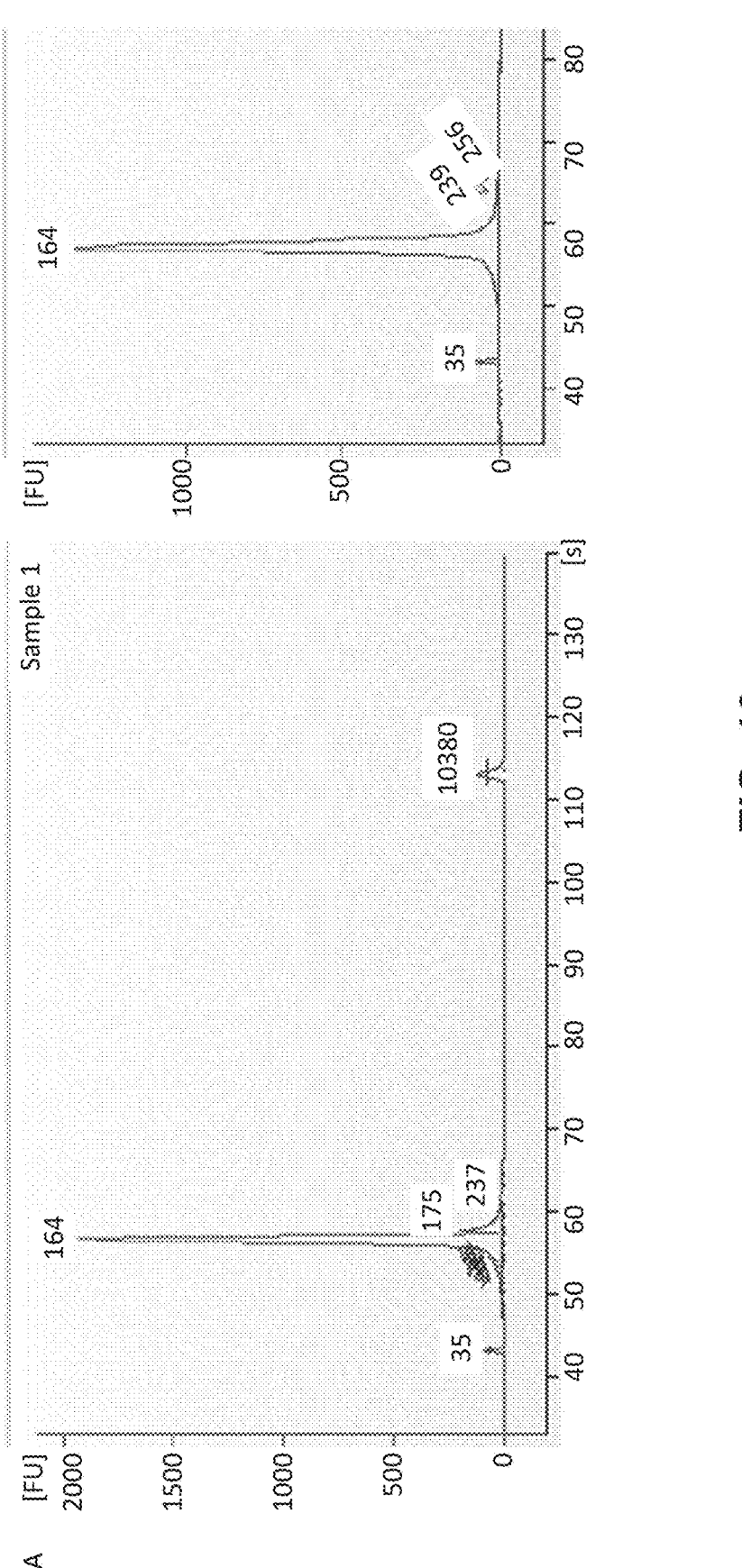

FIG. 10 depicts an electropherogram showing PCR products generated using methods described herein.

Figure 11A:
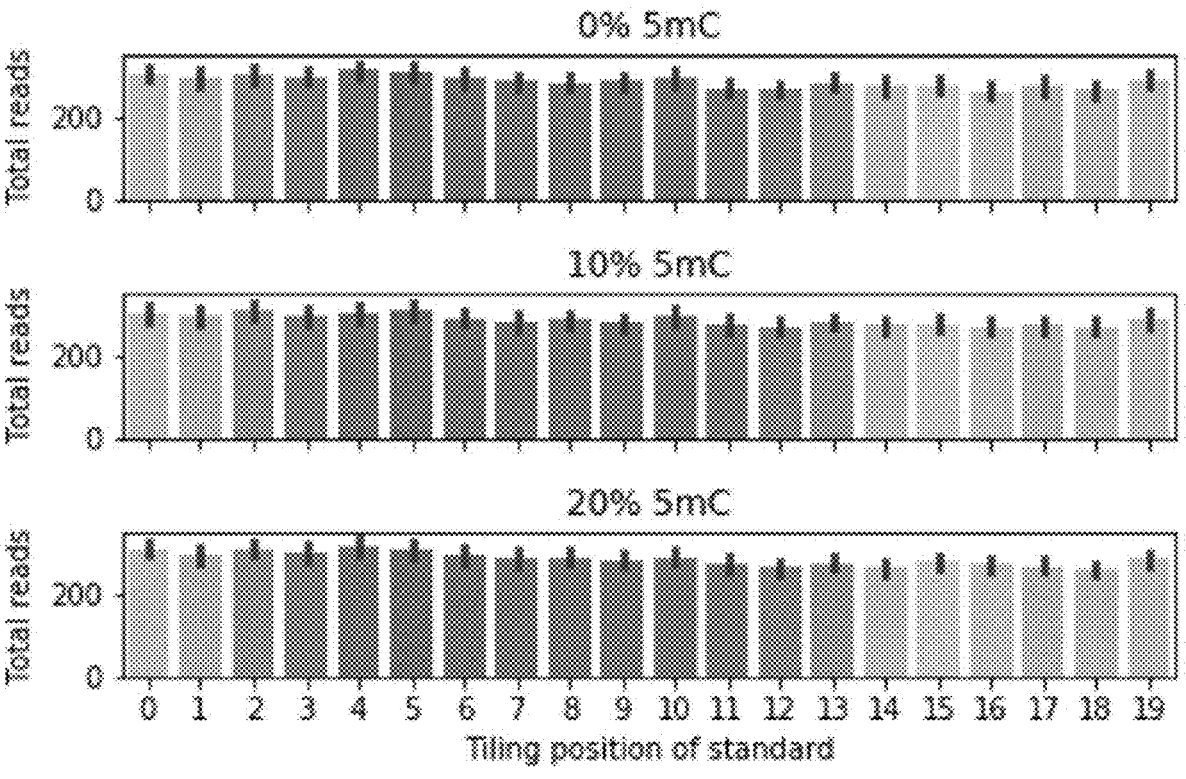

FIG. 11A depicts a graph of distribution of coverage of the polynucleotides generated using methods described herein for various percentages of 5mC: 0% (top), 10% (middle), 20% (bottom). The x-axis are labeled Tiling position of standard from 0 to 19 at 1 unit intervals; the y-axis is labeled total reads from 0 to 200 at 200 unit intervals.

Figure 11B:
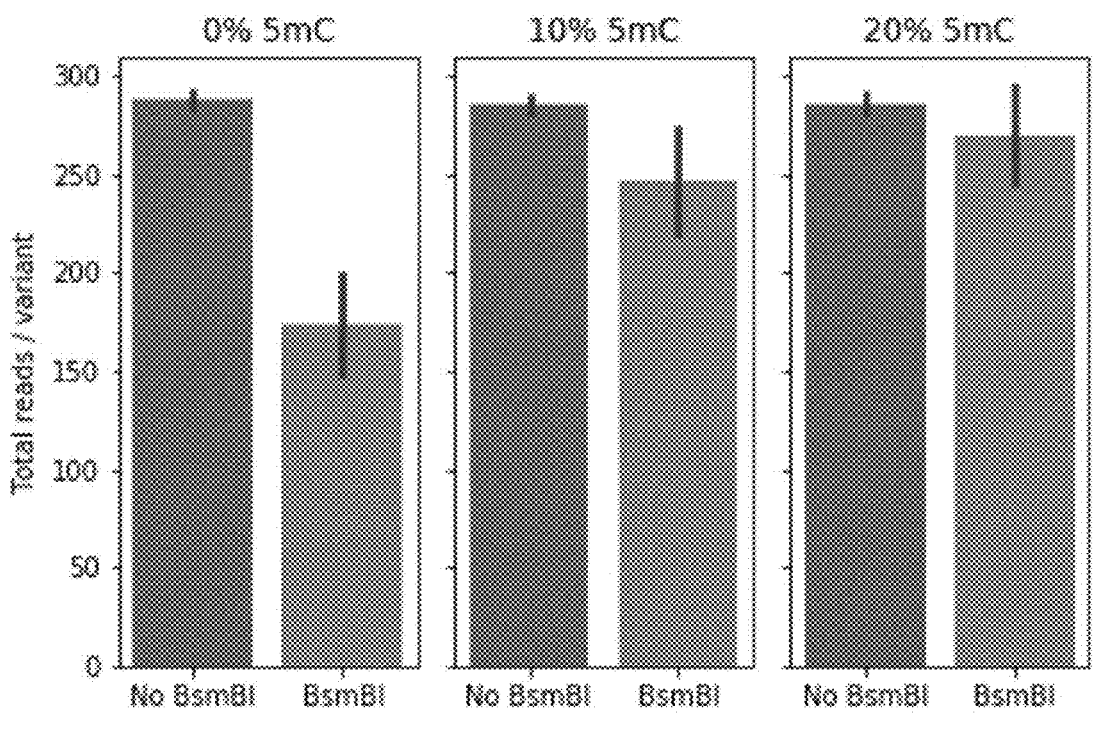

FIG. 11B depicts a graph of distribution of variants with endogenous BsmBI for the polynucleotides generated using methods described herein at various percentages of 5mC 0% (left), 10% (middle), 20% (right). No BSMBI conditions are represented as the left bar in each graph, and BsmBI conditions are represented as the right bar in each graph. The y-axis is labeled total reads/variant from 0 to 300 at 50 unit intervals.

Figure 11C:
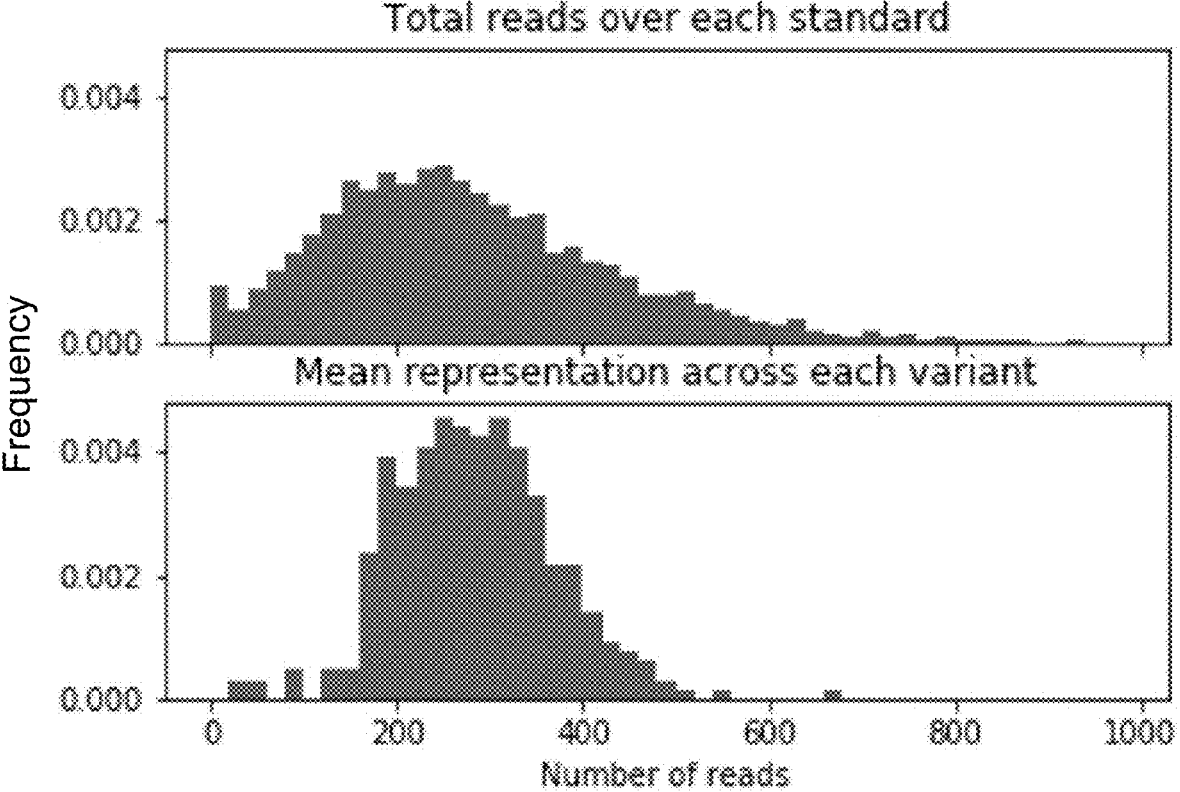

FIG. 11C depicts a graph of distribution over each standard and across each variant. The top graph is labeled total reads over each standard; the bottom graph is labeled mean representation across each variant. The x-axis is labeled number of reads from 0 to 1000 at 200 unit intervals; the y-axis is labeled frequency from 0.000 to 0.004 at 0.0002 intervals.

Figure 11D:
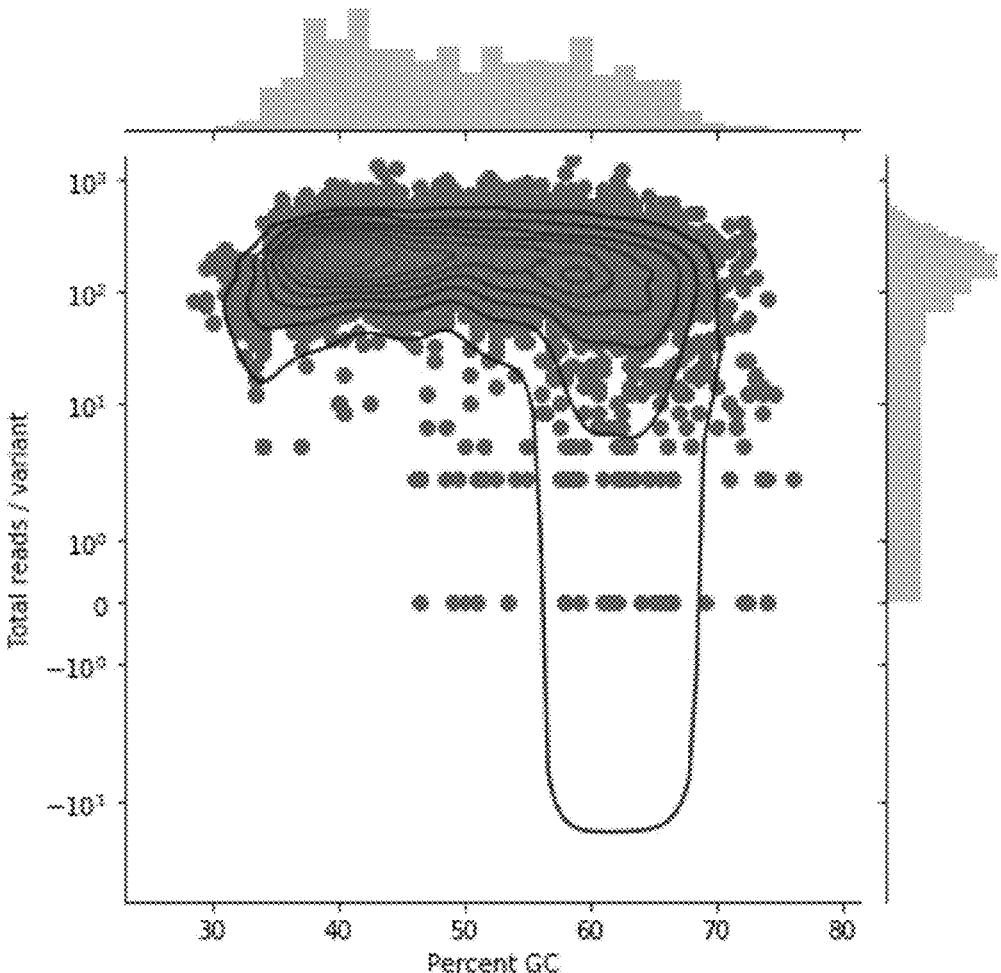

FIG. 11D depicts a two-dimensional plot of the distribution across GC bins. The x-axis is labeled percent GC from 30 to 80 at 10 unit intervals; the y-axis is labeled total reads/variant from −10 to 103 on a base 10 logarithmic scale.

Figure 12A:
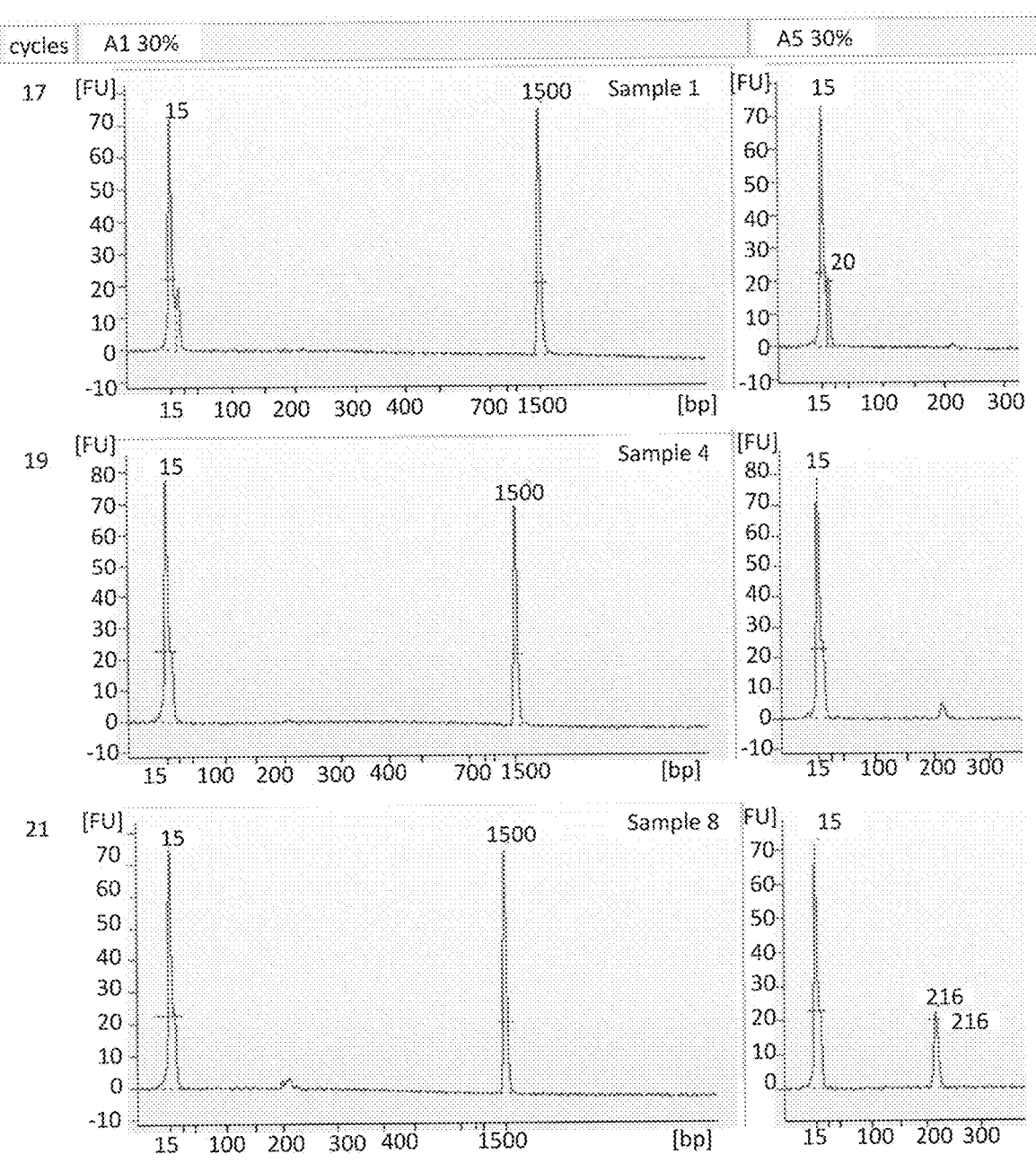
Figures 12B, 12C:
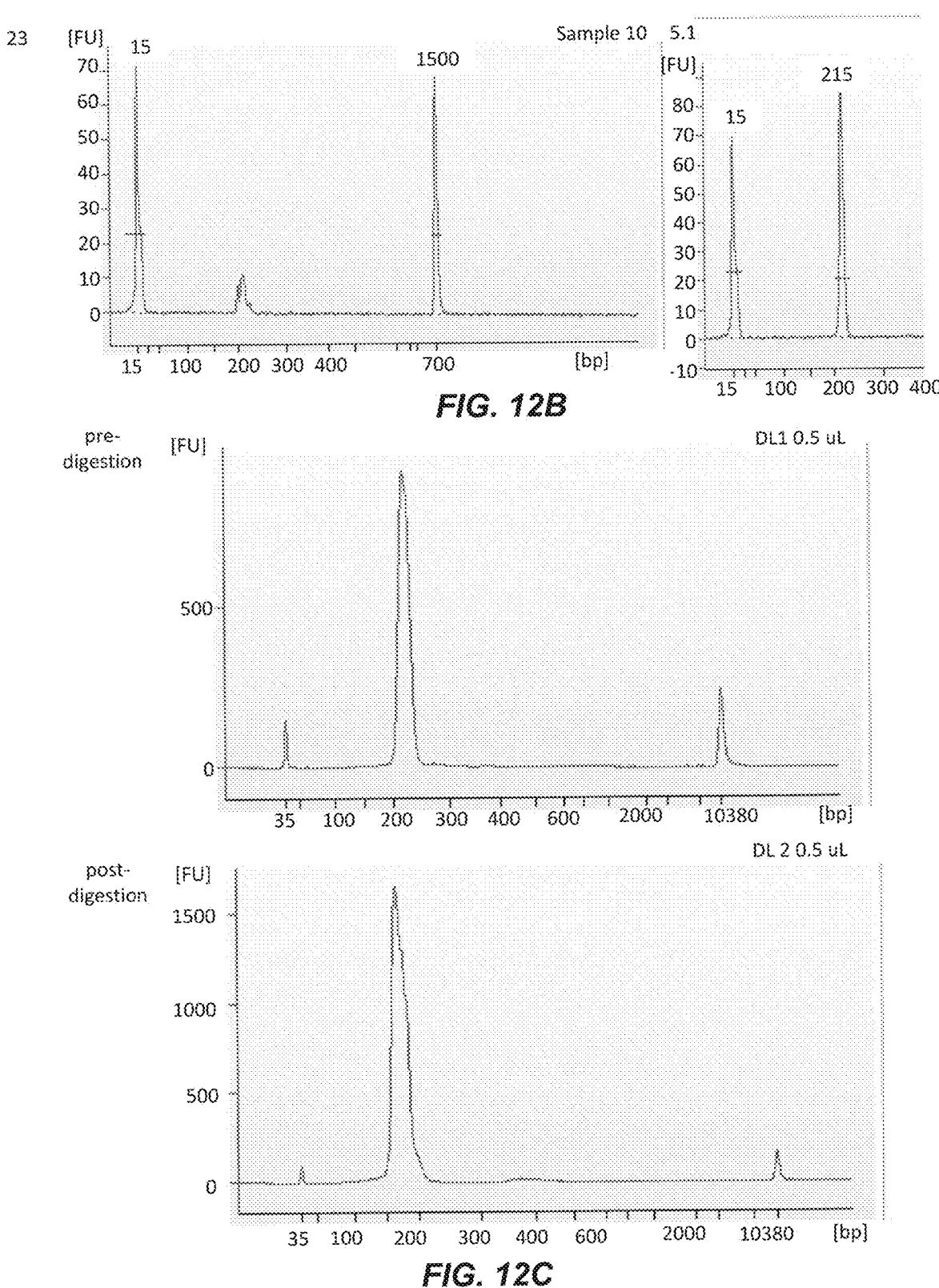

FIGS. 12A-12C depict electropherograms showing PCR products generated using methods described herein at various cycle numbers and pre-digestion and post-digestion. FIG. 12A: rows (top to bottom) correspond to conditions of 17, 19, and 21 cycles; columns (left to right) correspond to conditions 0% and 30% Me dCTP. FIG. 12B: 23 cycles, columns (left to right) correspond to conditions 0% and 30% Me dCTP. FIG. 12C corresponds to conditions of pre-digestion (top) and post-digestion (bottom).

Figure 12D:
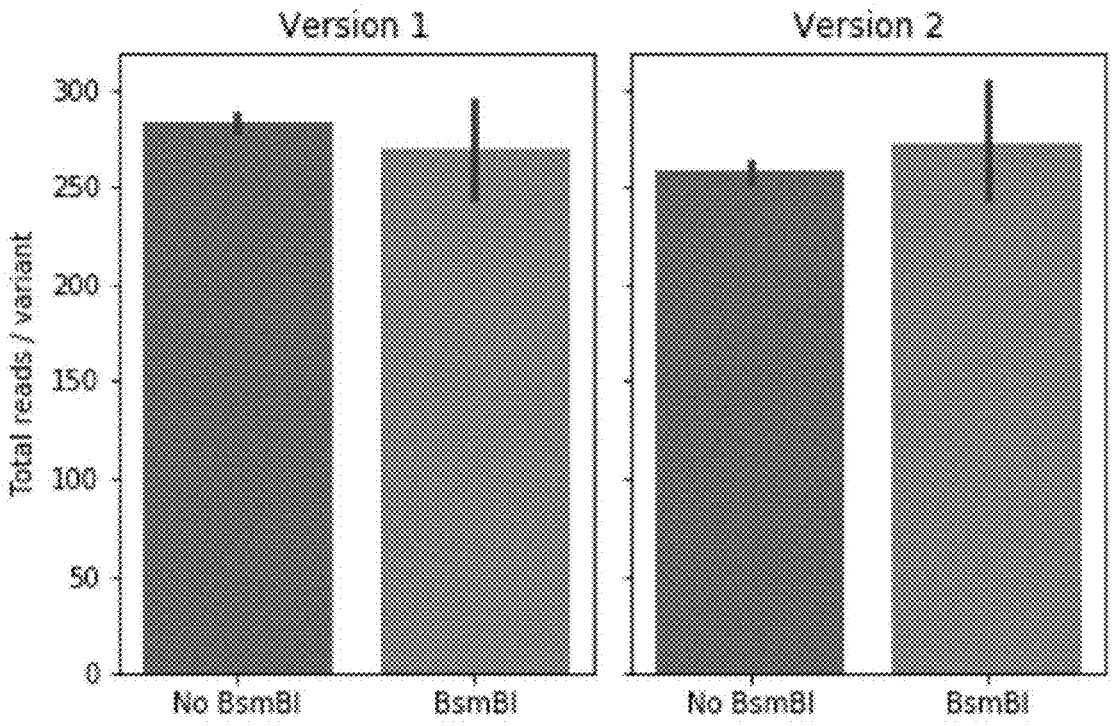

FIG. 12D depicts a graph of distribution of variants with endogenous BsmBI for the polynucleotides generated using methods described herein at two conditions version 1 (left) and version 2 (right). No BSMBI conditions are represented as the left bar in each graph, and BsmBI conditions are represented as the right bar in each graph. The y-axis is labeled total reads/variant from 0 to 300 at 50 unit intervals.

Figure 12E:
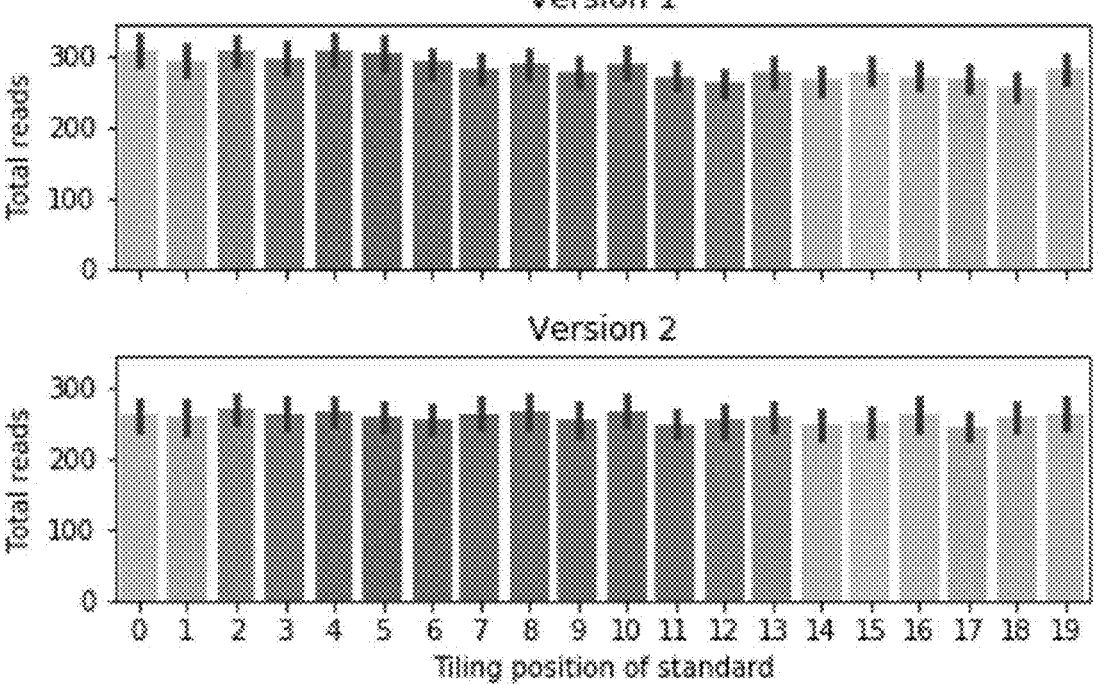

FIG. 12E depicts a graph of distribution of coverage of the polynucleotides generated using methods described herein for two conditions: version 1 (top) and version 2 (bottom). The x-axis are labeled Tiling position of standard from 0 to 19 at 1 unit intervals; the y-axis is labeled total reads from 0 to 300 at 100 unit intervals.

Figure 12F:
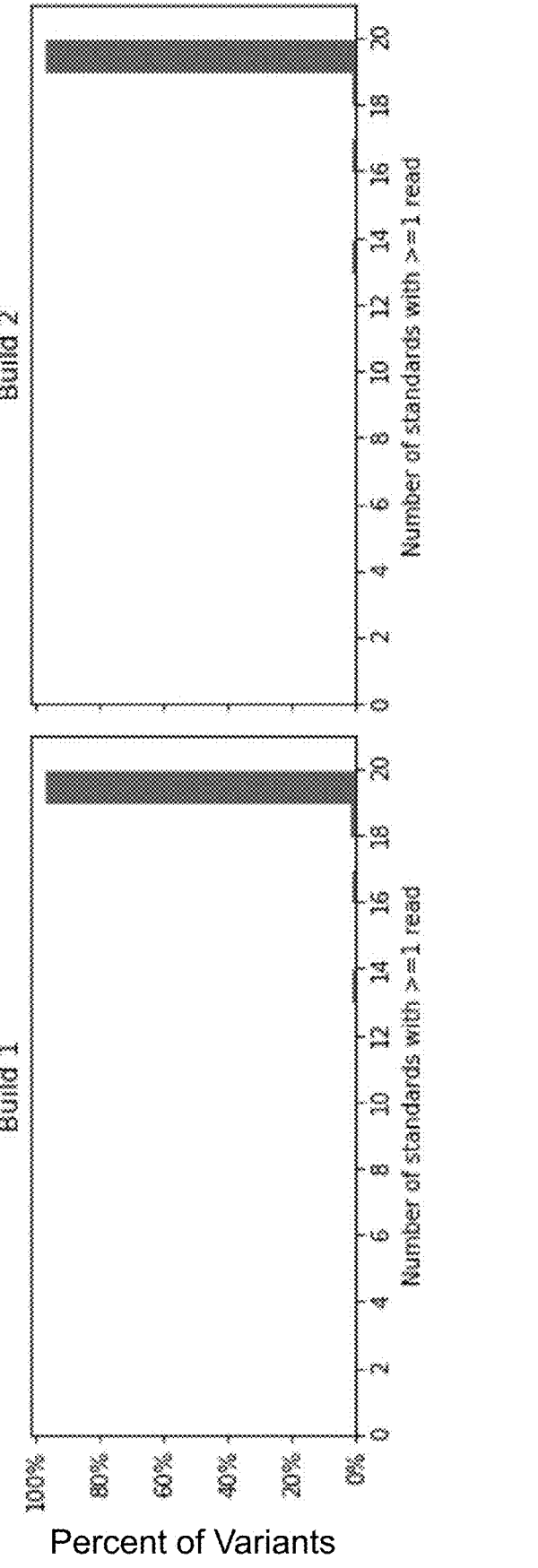

FIG. 12F depicts plots for two build conditions. The x-axis is labeled number of standards with >=1 read from 0 to 20 at 2 unit intervals; the y-axis is labeled percent of variants from 0-100% at 20% intervals.

Figure 12G:
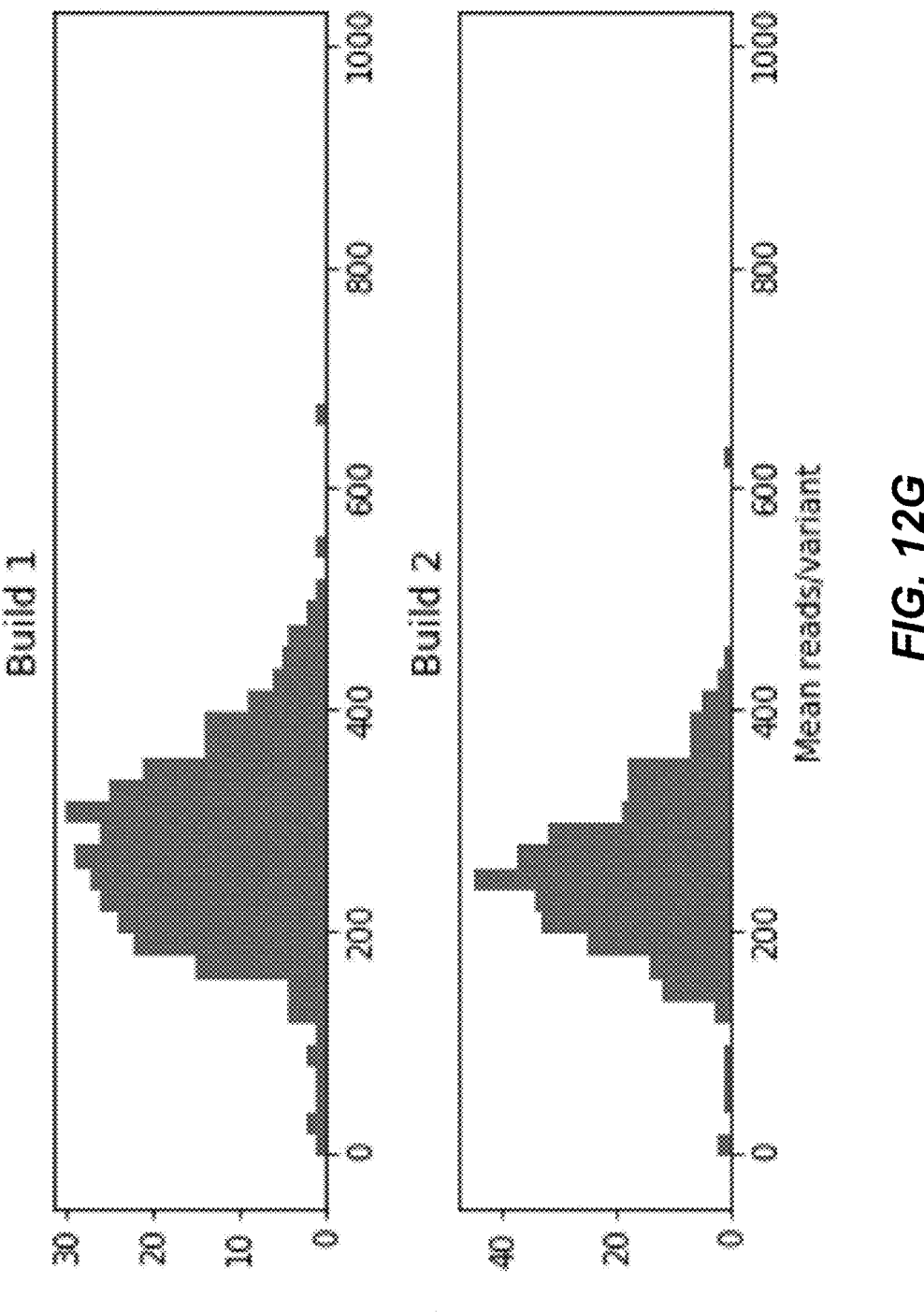

FIG. 12G depicts plots for two build conditions. The x-axis is labeled mean reads per variant from 0 to 1000 at 200 unit intervals; the y-axis is labeled number of variants from 0 to 40 at 20 unit intervals.

Figure 12H:
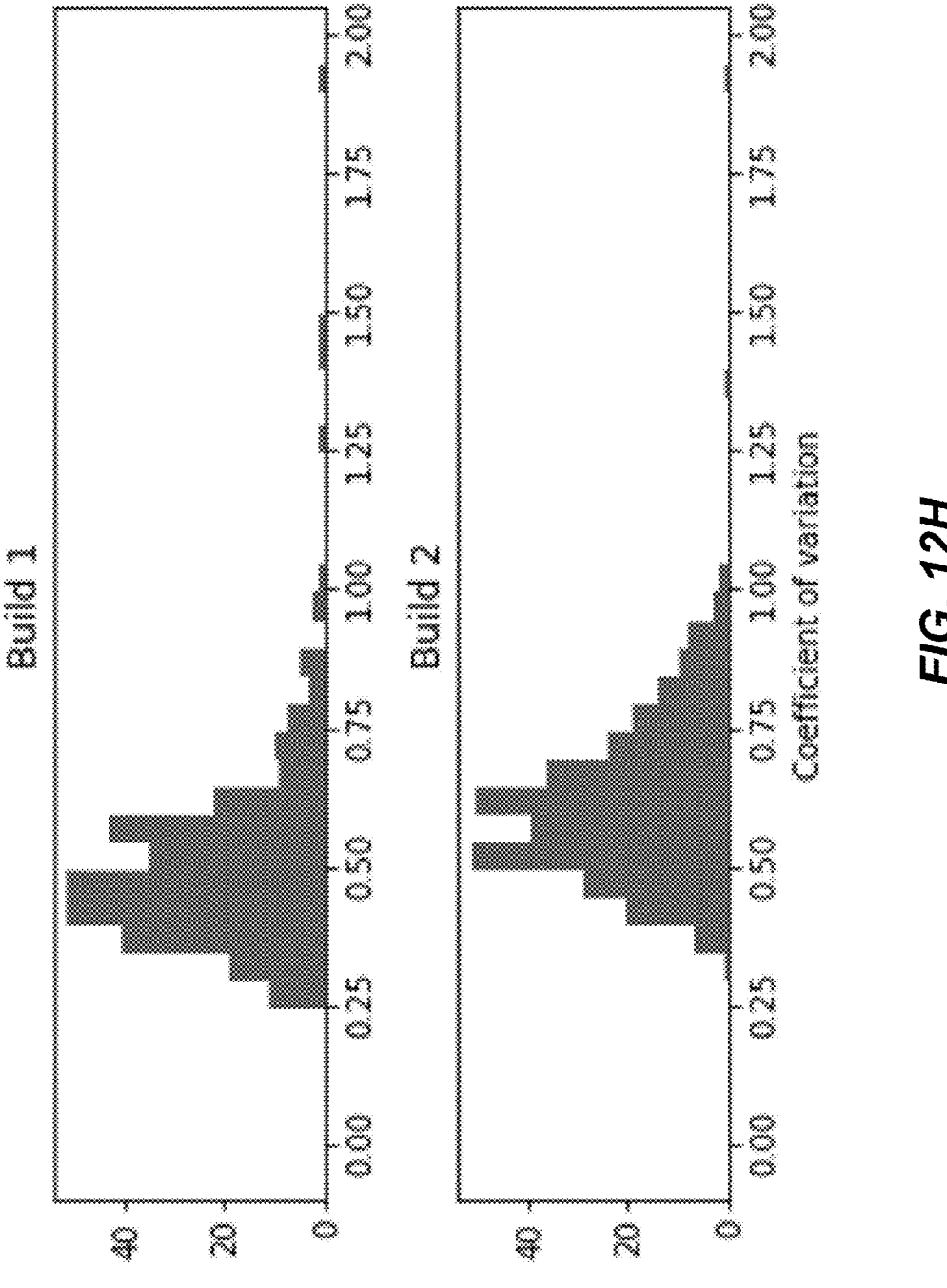

FIG. 12H depicts plots for two build conditions. The x-axis is labeled coefficient of variation from 0.00 to 2.00 at 0.25 unit intervals; the y-axis is labeled number of variants from 0 to 40 at 20 unit intervals.

Figure 12I:
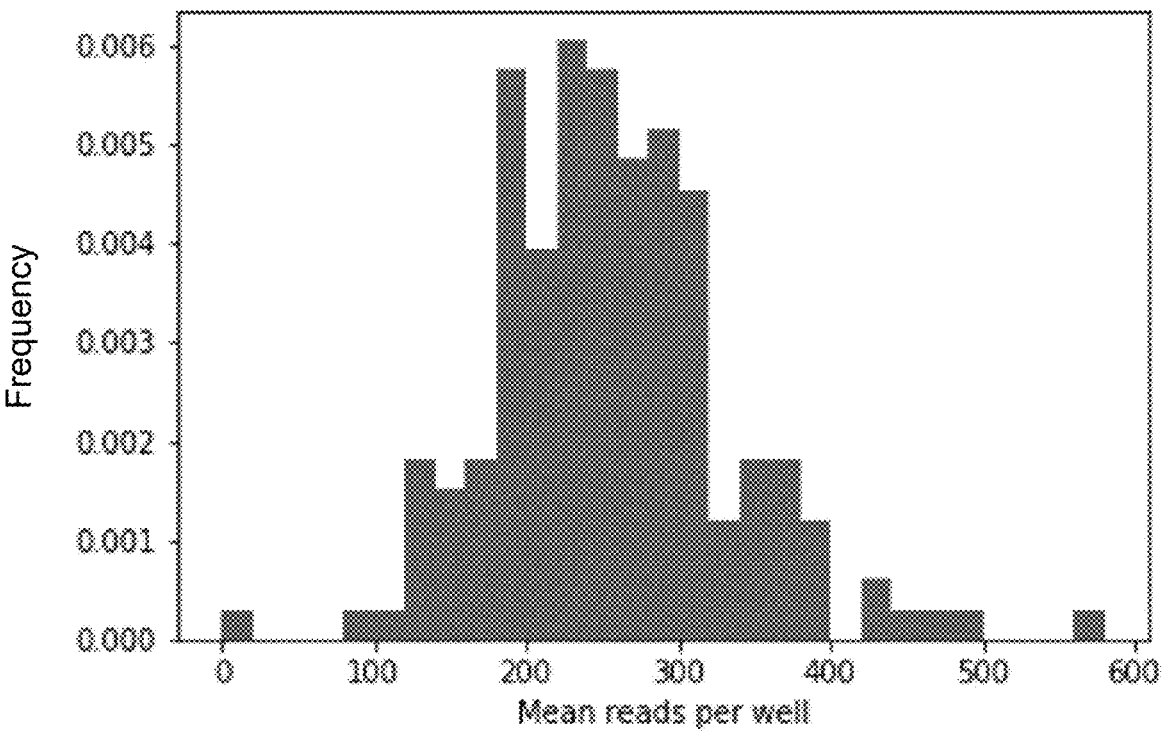

FIG. 12I depicts mean reads per well. The x-axis is labeled mean reads per well from 0 to 600 at 100 unit intervals; the y-axis is labeled frequency from 0.000 to 0.006 at 0.001 unit intervals.

Figure 12J:
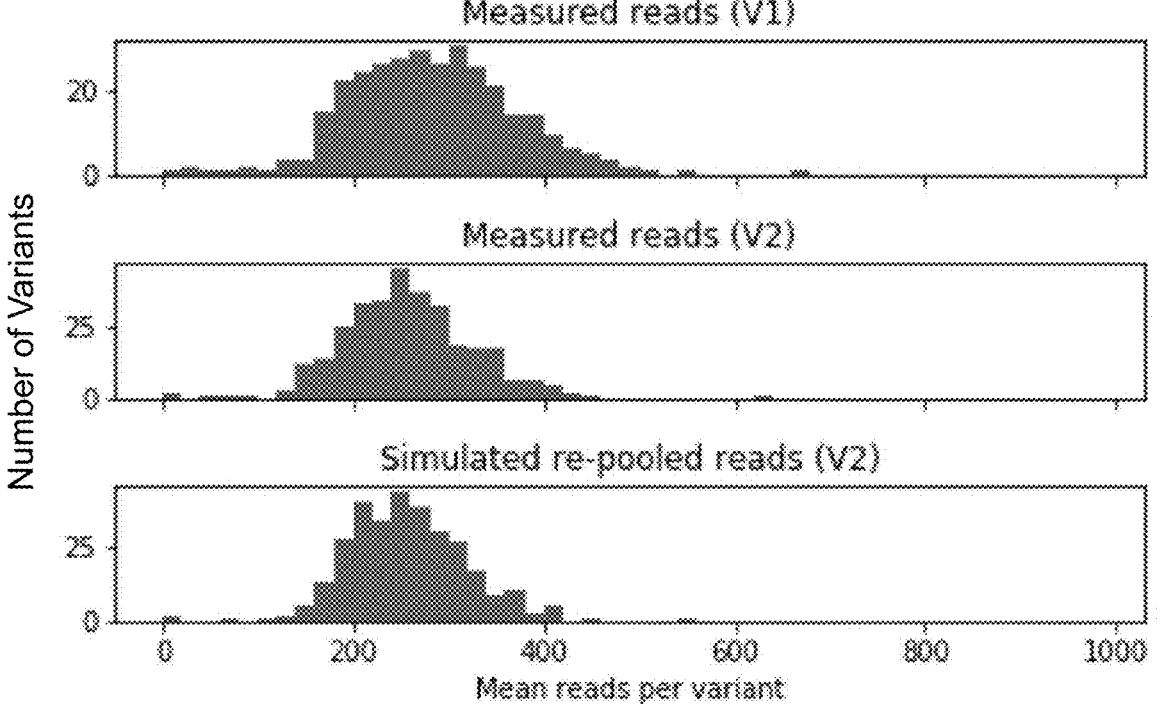

FIG. 12J depicts measured reads (v1, top), measured reads (v2, middle), and simulated re-pooled reads (v2, bottom). The x-axis is labeled mean reads per variant from 0 to 1000 at 200 unit intervals; the y-axis is labeled number of variants from 0 to 25 at 25 unit intervals.

Figure 12K:
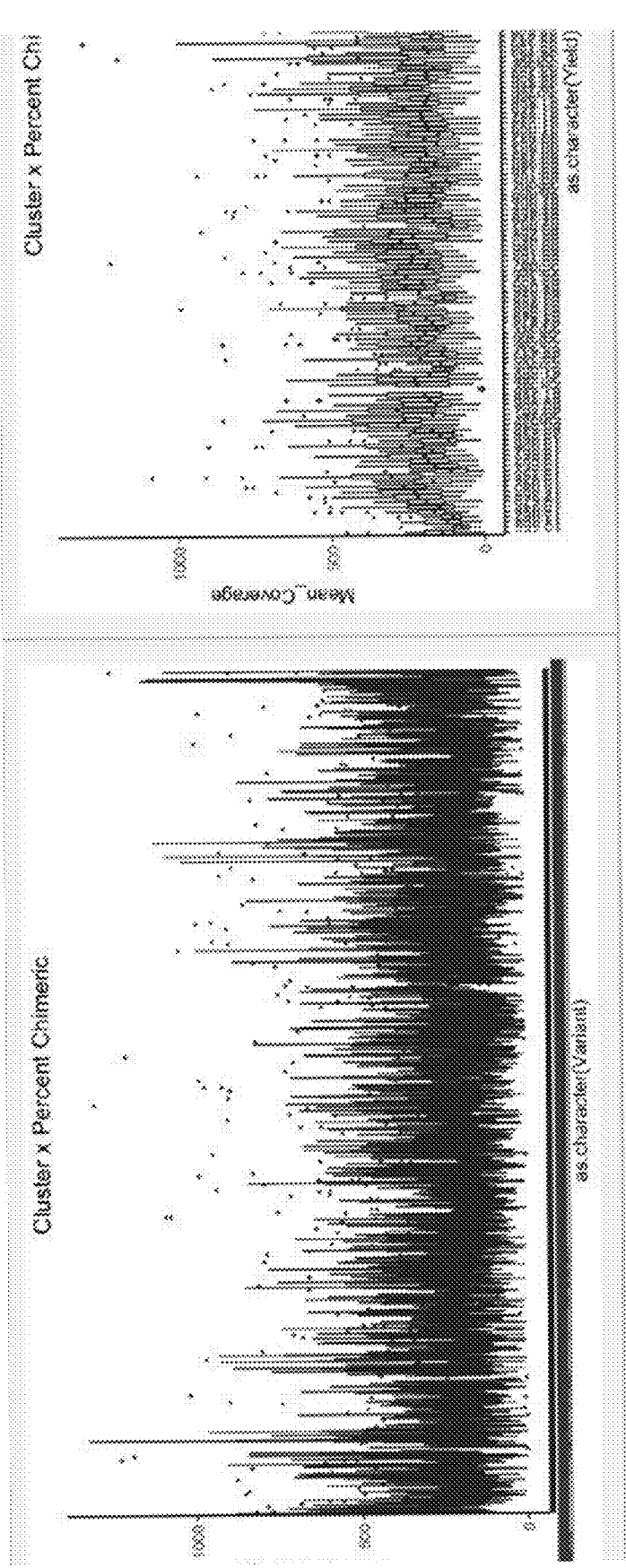

FIG. 12K plots of cluster x precent chimeric reads. The x-axis is labeled as.character(variant); the y-axis is labeled mean coverage from 0 to 1000 at 500 unit intervals.

Figure 13:
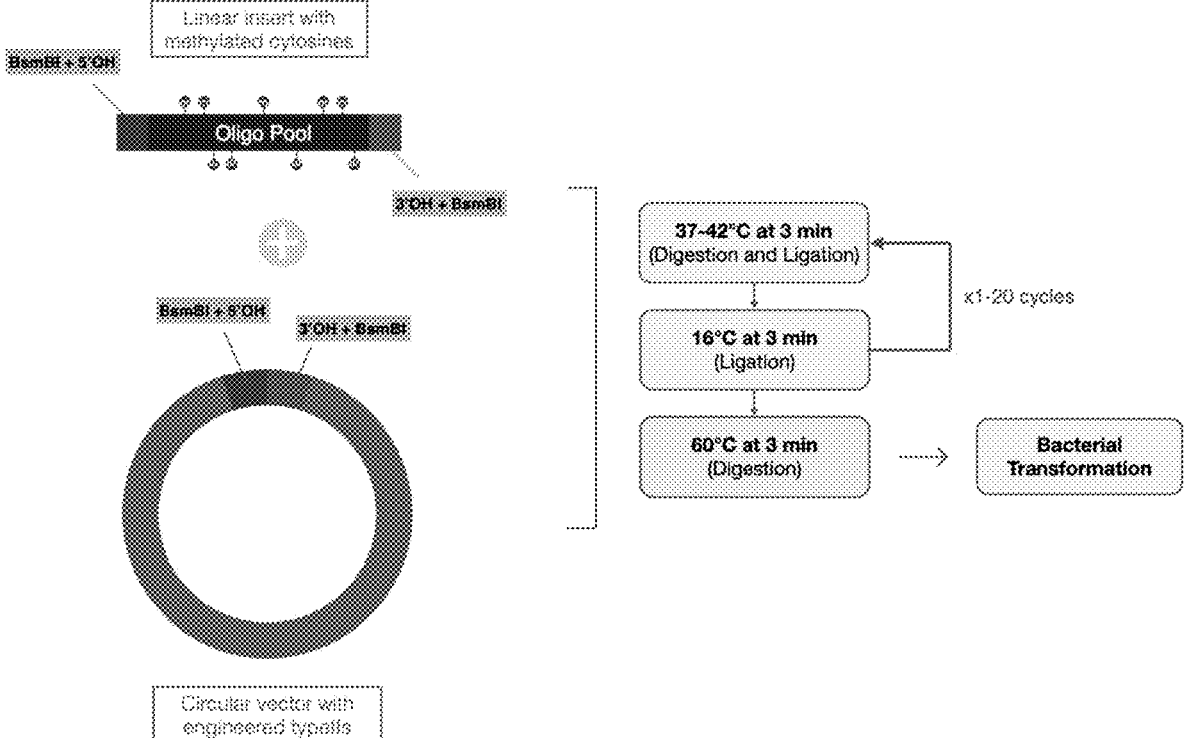

FIG. 13 depicts an exemplary workflow for golden gate cloning using the methods described herein. A linear insert comprises methylated cytosines, and the 5' and 3' adapter regions comprise BsmBI sides is combined with a circular vector comprising engineered type IIs sites and a target insert region having 5' and 3' cloning regions. The two components are digested at 37-42 deg C. for 3 min, 16 deg C. for 3 min for ligation, and the process is repeated from 1-20 cycles. After digestion at 60 deg C. for 3 min, the mixture is transformed.

Figure 14A:
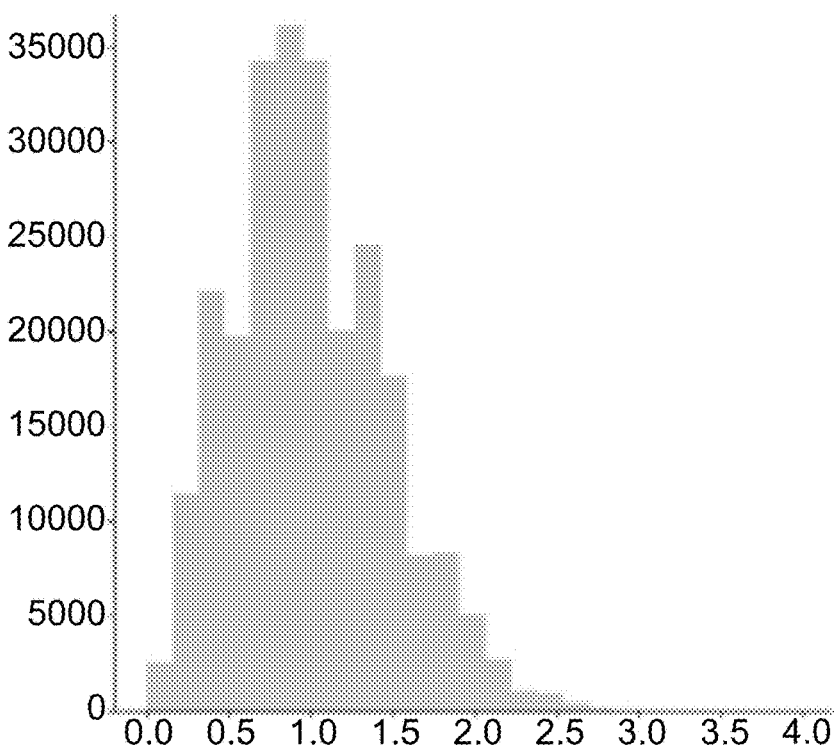
Figure 14A:
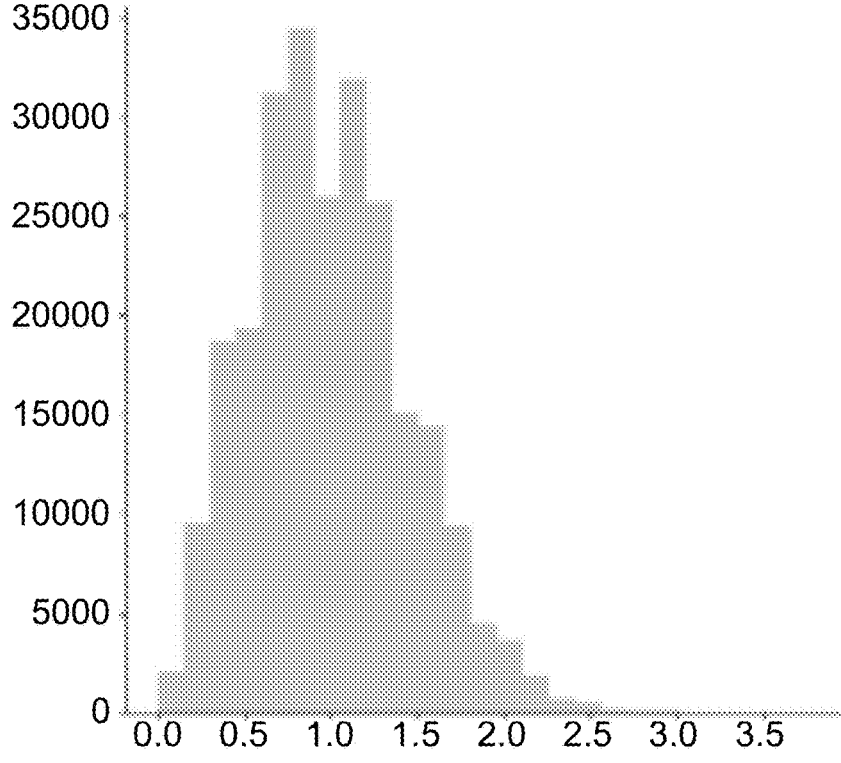

FIG. 14A depicts histograms of normalized read counts for two replicates (top and bottom) for a single cycle Golden Gate assembly reaction using undigested vector and insert. The x-axis is labeled 0.0 to 3.5 at 0.5 unit intervals; the y-axis represents counts and is labeled 0 to 35000 at 5000 unit intervals.

Figure 14B:
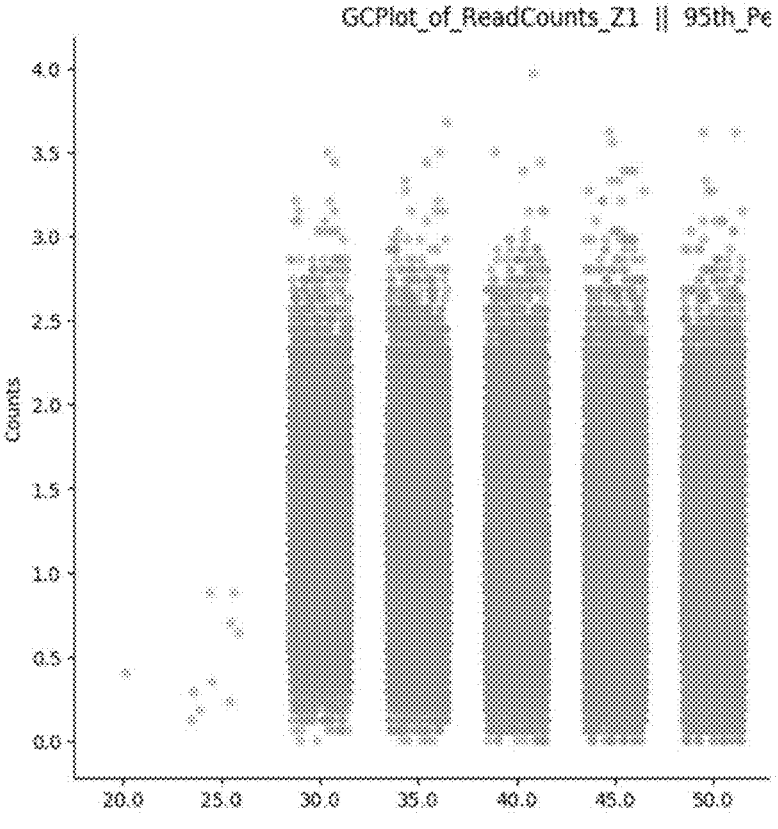
Figure 14B:
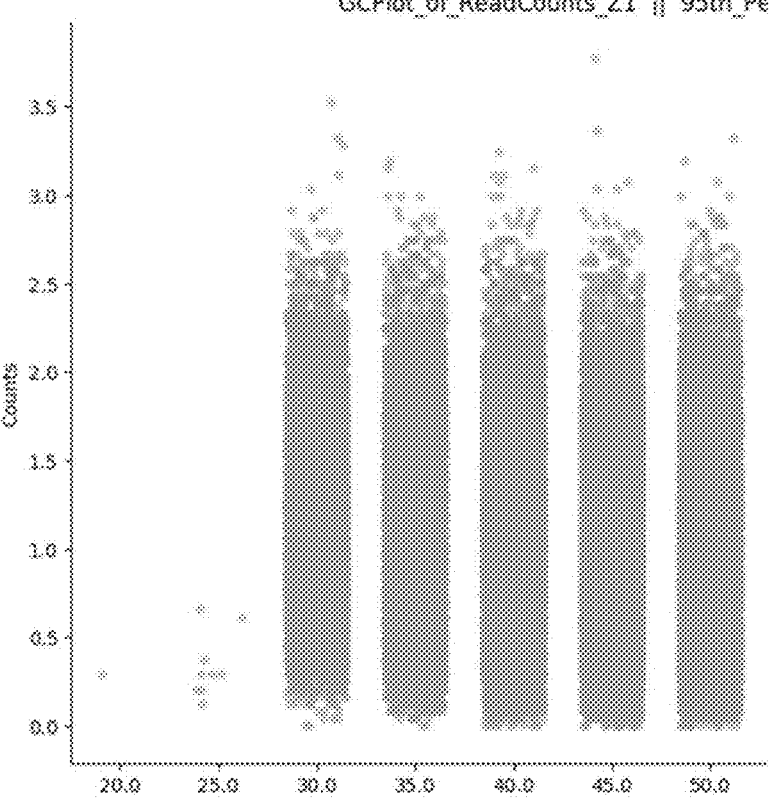

FIG. 14B depicts plots of GC read counts (top and bottom) for a single cycle Golden Gate assembly reaction using undigested vector and insert. The x-axis represents percent GC content and is labeled from 20.0 to 50.0 at 5.0 unit intervals; the y-axis represents counts and is labeled 0.0 to 3.5 at 0.5 unit intervals.

Figure 15A:
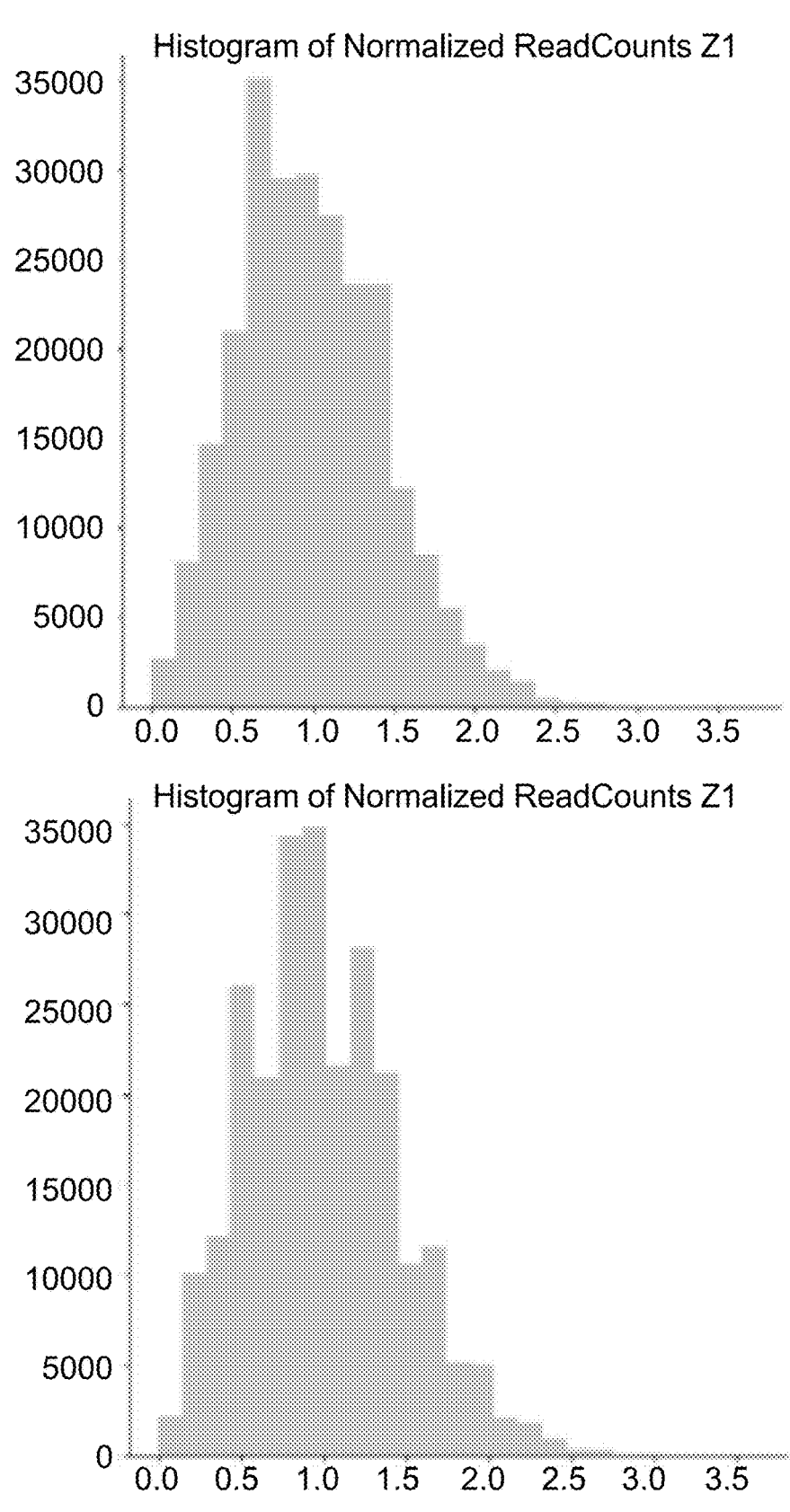

FIG. 15A depicts histograms of normalized read counts for two replicates (top and bottom) for a 20 cycle Golden Gate assembly reaction using undigested vector and insert. The x-axis is labeled 0.0 to 3.5 at 0.5 unit intervals; the y-axis represents counts and is labeled 0 to 35000 at 5000 unit intervals.

Figure 15B:
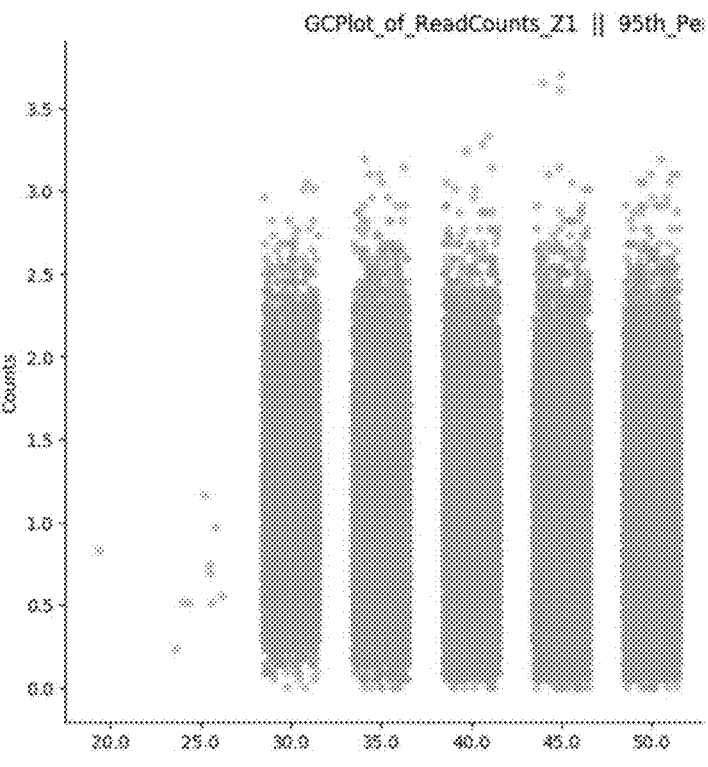
Figure 15B:
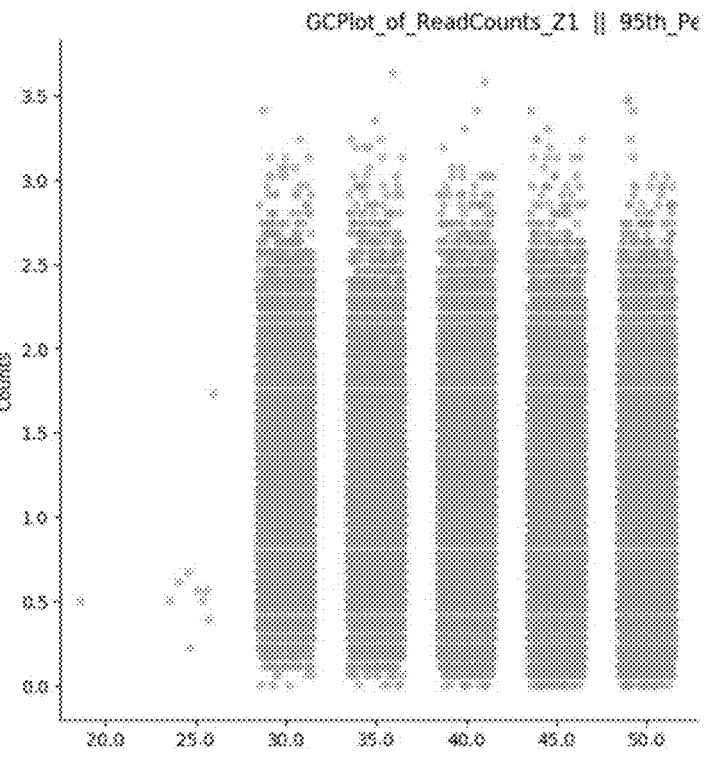

FIG. 15B depicts plots of GC read counts (top and bottom) for a 20 cycle Golden Gate assembly reaction using undigested vector and insert. The x-axis represents percent GC content and is labeled from 20.0 to 50.0 at 5.0 unit intervals; the y-axis represents counts and is labeled 0.0 to 3.5 at 0.5 unit intervals.

Figure 16A:
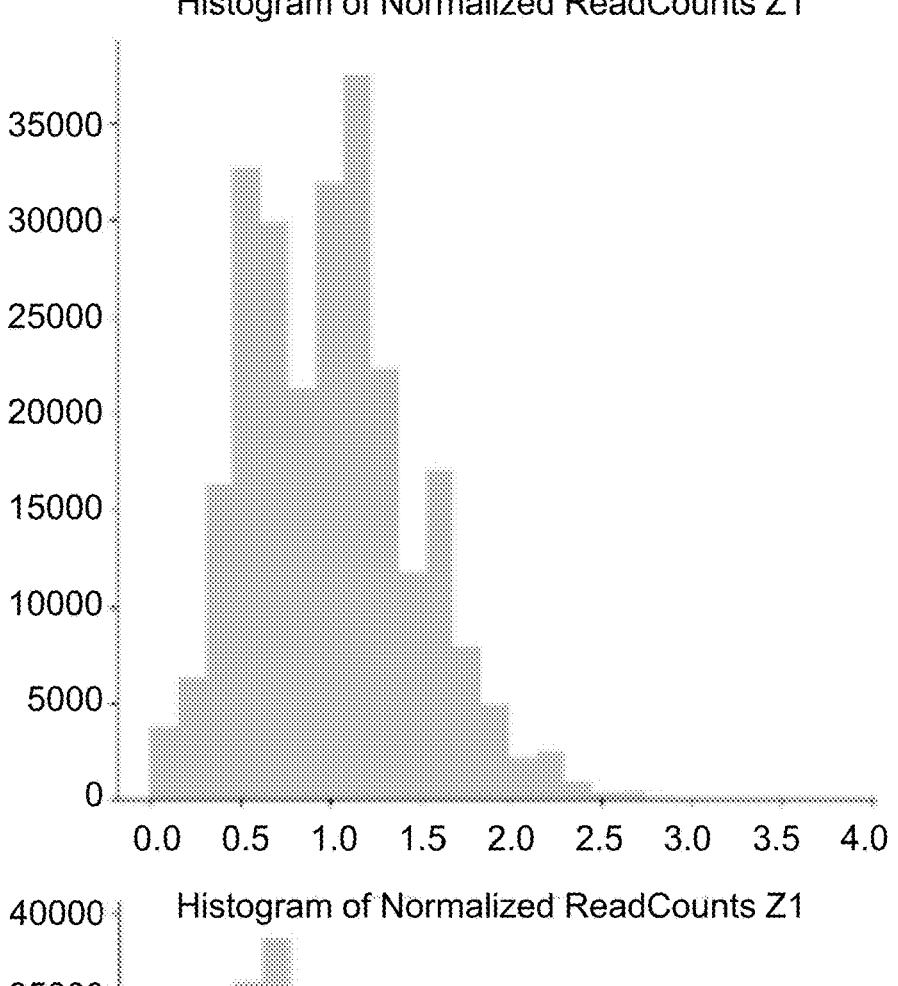
Figure 16A:
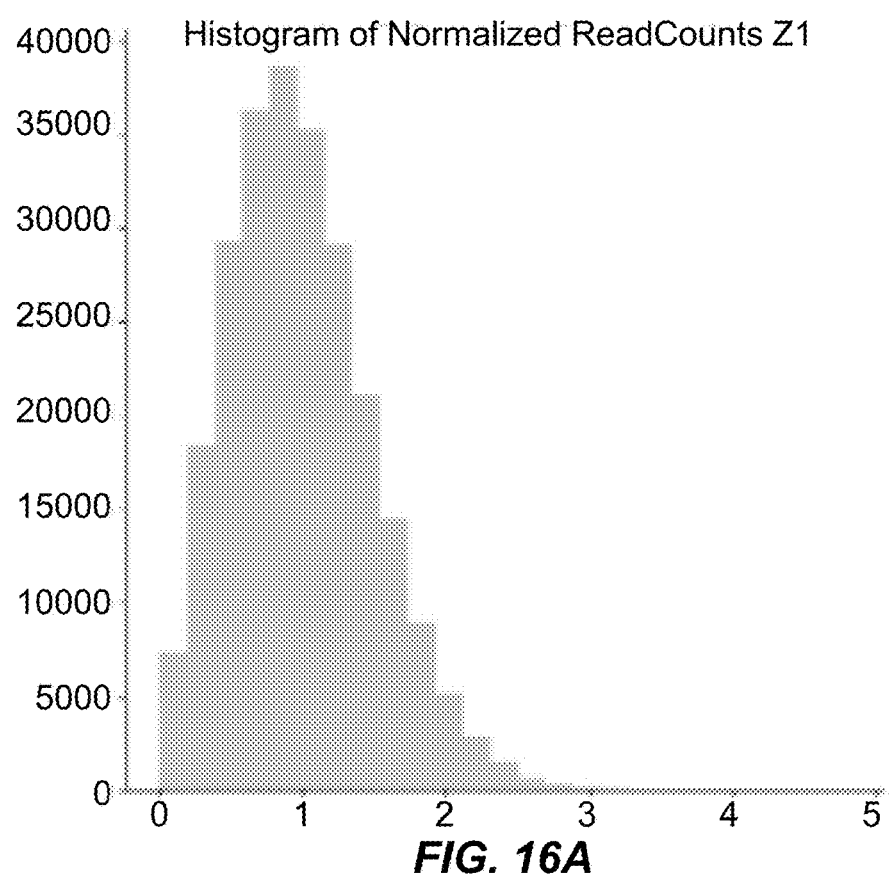

FIG. 16A depicts histograms of normalized read counts for two replicates (top and bottom) for a 40 cycle Golden Gate assembly reaction using undigested vector and insert. The x-axis is labeled 0.0 to 3.5 at 0.5 unit intervals; the y-axis represents counts and is labeled 0 to 35000 at 5000 unit intervals.

Figure 16B:
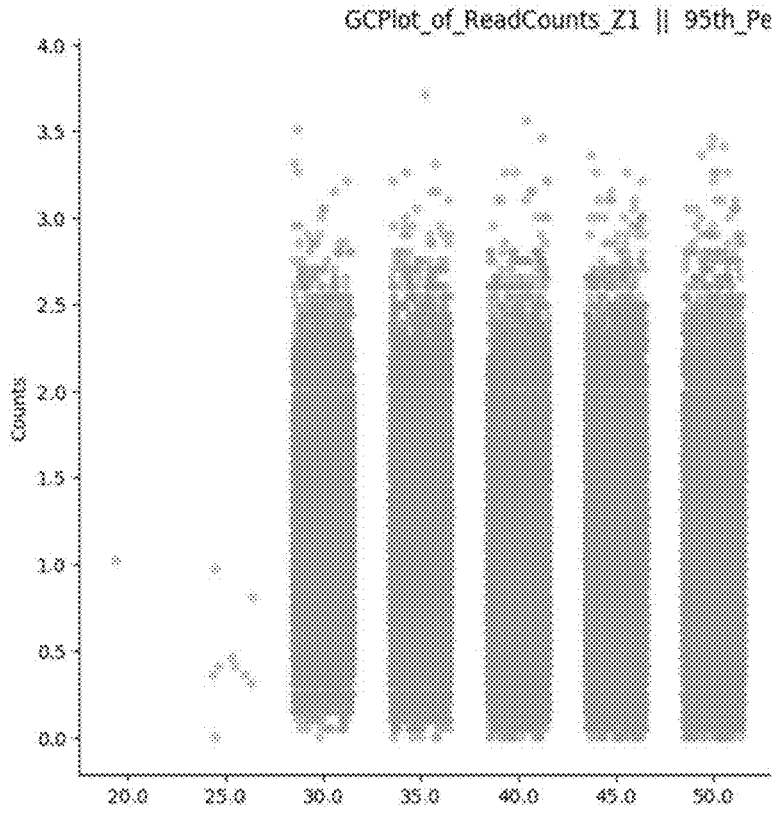
Figure 16B:
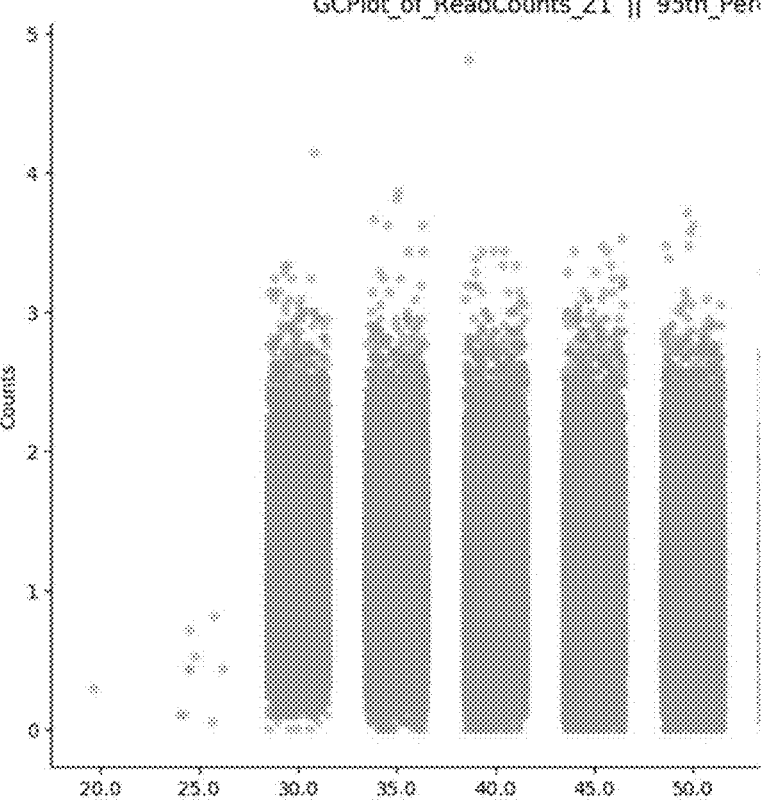

FIG. 16B depicts plots of GC read counts (top and bottom) for a 40 cycle Golden Gate assembly reaction using undigested vector and insert. The x-axis represents percent GC content and is labeled from 20.0 to 50.0 at 5.0 unit intervals; the y-axis represents counts and is labeled 0.0 to 4.0 at 0.5 unit intervals (top) or 0 to 5 at 1 unit intervals (bottom).

Figure 17A:
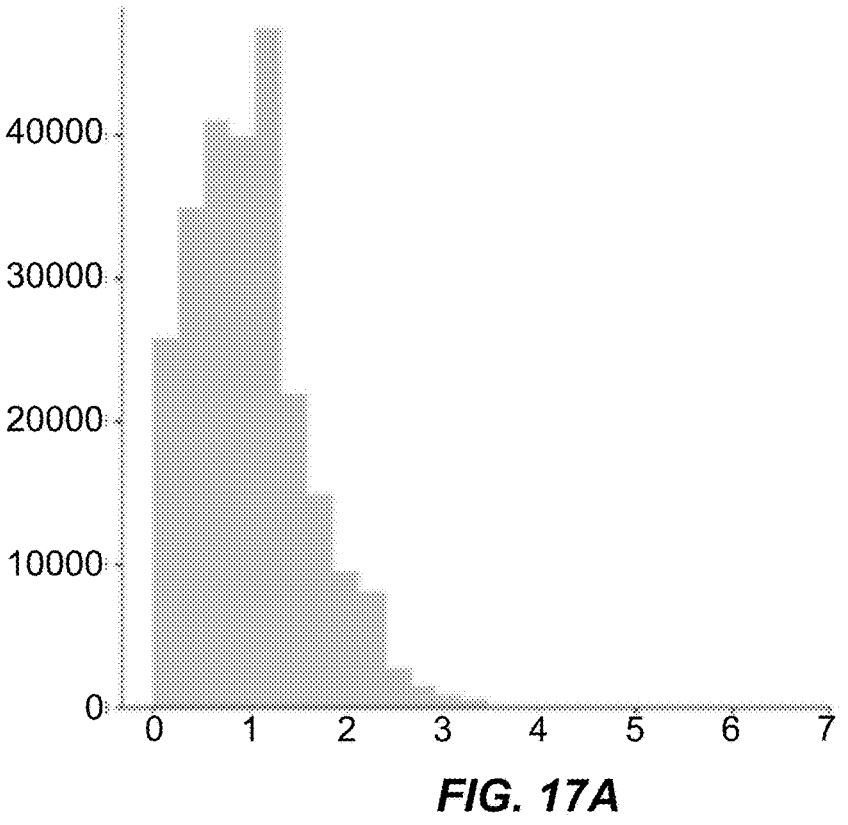

FIG. 17A depicts a histogram of normalized read counts for a traditional overnight ligation of linearized vector and insert. The x-axis is labeled 0.0 to 3.5 at 0.5 unit intervals; the y-axis represents counts and is labeled 0 to 5000 at 35000.

Figure 17B:
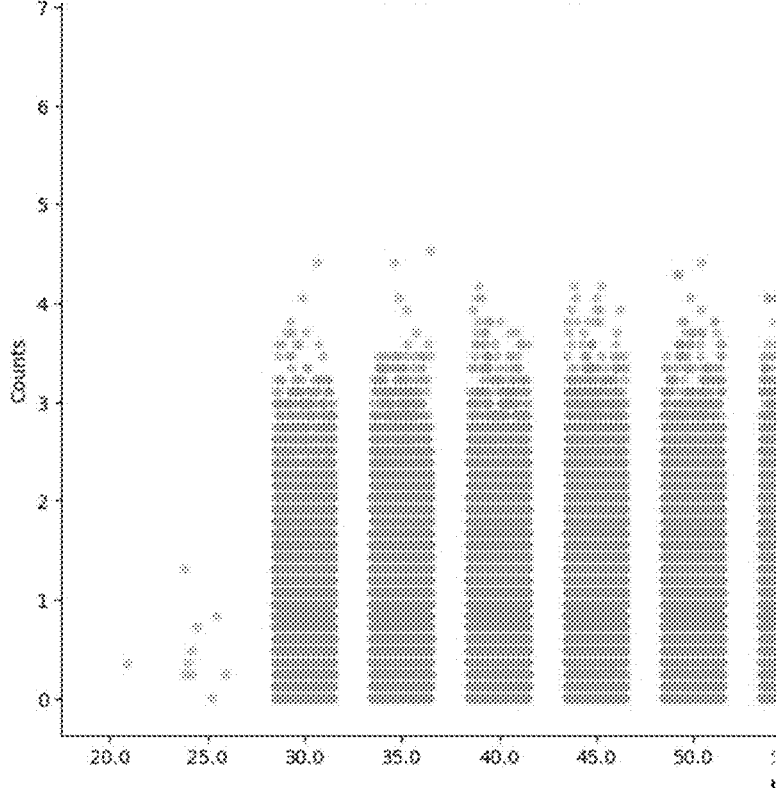

FIG. 17B depicts a plot of GC read counts for a traditional overnight ligation of linearized vector and insert. The x-axis represents percent GC content and is labeled from 20.0 to 50.0 at 5.0 unit intervals; the y-axis represents counts and is labeled 0 to 7 at 1 unit intervals.

DETAILED DESCRIPTION

Definitions

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "nucleic acid" encompasses double- or triple-stranded nucleic acids, as well as single-stranded molecules. In double- or triple-stranded nucleic acids, the nucleic acid strands need not be coextensive (i.e., a double-stranded nucleic acid need not be double-stranded along the entire length of both strands). Nucleic acid sequences, when provided, are listed in the 5' to 3' direction, unless stated otherwise. Methods described herein provide for the generation of isolated nucleic acids. Methods described herein additionally provide for the generation of isolated and purified nucleic acids. A "nucleic acid" as referred to herein can comprise at least 5, 10, 20, 30, 40, 50, 60, 70, 80, 90, 100, 125, 150, 175, 200, 225, 250, 275, 300, 325, 350, 375, 400, 425, 450, 475, 500, 600, 700, 800, 900, 1000, 1100, 1200, 1300, 1400, 1500, 1600, 1700, 1800, 1900, 2000, or more bases in length. Moreover, provided herein are methods for the synthesis of any number of polypeptide-segments encoding nucleotide sequences, including sequences encoding non-ribosomal peptides (NRPs), sequences encoding non-ribosomal peptide-synthetase (NRPS) modules and synthetic variants, polypeptide segments of other modular proteins, such as antibodies, polypeptide segments from other protein families, including non-coding DNA or RNA, such as regulatory sequences e.g. promoters, transcription factors, enhancers, siRNA, shRNA, RNAi, miRNA, small nucleolar RNA derived from microRNA, or any functional or structural DNA or RNA unit of interest. The following are non-limiting examples of polynucleotides: coding or non-coding regions of a gene or gene fragment, intergenic DNA, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), small nucleolar RNA, ribozymes, complementary DNA (cDNA), which is a DNA representation of mRNA, usually obtained by reverse transcription of messenger RNA (mRNA) or by amplification; DNA molecules produced synthetically or by amplification, genomic DNA, recombinant polynucleotides, branched polynucleotides, plasmids, vectors, isolated DNA of any sequence, isolated RNA of any sequence, nucleic acid probes, and primers. cDNA encoding for a gene or gene fragment referred to herein may comprise at least one region encoding for exon sequences without an intervening intron sequence in the genomic equivalent sequence.

Unless specifically stated or obvious from context, as used herein, the term "about" in reference to a number or range of numbers is understood to mean the stated number and numbers+/−10% thereof, or 10% below the lower listed limit and 10% above the higher listed limit for the values listed for a range.

"Modified bases" as used herein in some instances refer to bases present in DNA or RNA polymers (e.g., polynucleotides) or monomers (e.g., nucleotides) excluding bases present in A, T, C, or G.

Nucleic Acid Assembly

Described herein are methods and compositions for the assembly of nucleic acid sequences. Assembly of such sequences may in some cases be challenging due to specific properties of the assembly fragments, such as GC content, repeating regions, and secondary structure. Additionally, assembly of libraries of such sequences may be assembled in parallel, with members of the library possessing regions of high variability across members. Such parallel assembly of fragments is challenging due to the presence of highly variable regions across members of the library for such fragments. Moreover, assembly may result in errors, such as incorrectly assembled nucleic acids. Nucleic acids comprising variable regions may include nucleic acids encoding for genes (such as proteins or antibodies), or non-coding nucleic acids. In some instances, the genes are associated with a disease or disorder (e.g., cancer). In some instances, methods described herein are performed in-vitro.

Described herein are methods and compositions for the assembly of nucleic acid sequences resulting in improved representation and distribution. In some instances, methods and compositions for the assembly of nucleic acid sequences result in sequences that would fall out of the normal distribution to be represented. In some instances, methods and compositions for the assembly of nucleic acid sequences comprise using adapters comprising a restriction enzyme and amplification with modified nucleotides (e.g., methyl-dCTP).

Compositions provided herein may comprise polynucleotides. In some instances, polynucleotide are synthetic polynucleotides (e.g., synthesized de-novo using methods known in the art). In some instances, a polynucleotide comprises one or more regions (e.g., a first region, second region, third region, or more regions). In some instances, a polynucleotide comprises a first region and a second region. In some instances, a first region comprises at least one endonuclease cleavage site. In some instances, a polynucleotide comprises a first region and second region. In some instances the second region comprises at least one modified base. Modified bases in some instance are configured to reduce the efficiency of cleavage at the at least one endonuclease cleavage site. In some instances, polynucleotides comprise a first region that is substantially free of modified bases and comprising endonuclease sites, and a second region comprising one or more modified bases. In some instances, regions comprise adapters configured for removal by digestion by endonucleases. In some instances a polynucleotide comprises: a first region comprising at least one endonuclease cleavage site; and a second region comprising at least one modified base, wherein the modified base reduces the efficiency of cleavage at the at least one endonuclease cleavage site.

Polynucleotides may comprise any number of endonuclease cleavage sites. In some instances, endonuclease cleavage sites are present in only certain regions of a polynucleotide. In some instances, a polynucleotide comprises at least 1, 2, 3, 4, 5, 8, 10, 12, 15, 20, 25, 30, 35, 45, 50, or at least 55 endonuclease cleavage sites. In some instances, a polynucleotide comprises no more than 1, 2, 3, 4, 5, 8, 10, 12, 15, 20, 25, 30, 35, 45, 50, or no more than 55 endonuclease cleavage sites. In some instances, a polynucleotide comprises 1-20, 1-15, 1-10, 1-7, 1-5, 1-3, 1-2, 1-4, 1-50, 2-50, 2-20, 2-10, 5-10, 5-20, 5-30, 5-15, 10-15, 10-20, 10-50, 20-50, 20-70, or 30-50 endonuclease cleavage sites. In some instances, an endonuclease cleavage site comprises a Type IIS endonuclease site. In some instances, an endonuclease cleavage is selected from the group consisting of AcuI, AlwI, BaeI, BbsI, BbvI, BccI, BceAI, BcgI, BciVI, BcoDI, BfuAI, BmrI, BpmI, BpuEI, BsaI, BsaXI, BseRI, BsgI, BsmAI, BsmBI, BsmFI, BsmI, BspCNI, BspMI, BspQI, BsrDI, BsrI, BtgZI, BtsCI, BtsI, BtsIMutI, CspCI, EarI, EciI, Esp3I, FauI, FokI, HgaI, HphI, HpyAV, MboII, MlyI, MmeI, MnlI, NmeAIII, PleI, SapI, and SfaNI. In some instances, a Type IIS endonuclease site comprises BsmBI. In some instances, a polynucleotide comprises one or more types of endonuclease sites. Different regions of a polynucleotide may comprise different numbers of endonuclease cleavage sites depending on the length of the sequence or other factors. In some instances, a region comprising endonuclease cleavage sites is configured for subsequent removal.

Polynucleotides may comprise modified bases which reduce the efficiency of cleavage at an endonuclease cleavage site. Modified bases in some instances are attached to sugars. In some instances, modified bases are present on DNA or RNA. In some instances, a modified base comprises a derivative of a base found in T, C, G, A, or U. In some instances, a modified base comprises a naturally occurring post-transcriptional modification of a base found in T, C, G, A, or U. In some instances, a modified base comprises a synthetic derivative of a base found in T, C, G, A, or U. In some instances, a modified base comprises a methylated base. In some instances, a modified base comprises a modified DNA base. In some instances, a modified base comprises a modified RNA base. In some instances, a modified base comprises derivative of cytosine. In some instances, a modified base comprises derivative of deoxycytosine. In some instances, a modified base is selected from the group consisting of 5-methylcytosine, N6-methyladenosine, N3-methyladenosine, N7-methylguanosine, 5-hydroxymethylcytosine, pseudouridine, thiouridine, isoguanosine, isocytosine, dihydrouridine, queuosine, wyosine, inosine, triazole, diaminopurine, j-D-glucopyranosyloxymethyluracil, 8-oxoguanosine, or 2'-O-methyl adenosine,2'-O-methyl cytidine, 2'-O-methyl guanosine, and 2'-O-methyl uridine. In some instances, a modified base comprises methyl-dCTP (mdCTP). In some instances, a polynucleotide comprises at least 1, 2, 3, 4, 5, 6, 7, 8, 9, 10, 12, 15, 20, 25, 30, 40, 50, or at least 70 modified bases. In some instances, a polynucleotide comprises no more than 1, 2, 3, 4, 5, 6, 7, 8, 9, 10, 12, 15, 20, 25, 30, 40, 50, or no more than 70 modified bases. In some instances, a polynucleotide comprises 1-50, 1-50, 1-40, 1-30, 1-25, 1-20, 1-15, 1-10, or 1-5 modified bases. In some instances, a polynucleotide comprises at least 1%, 5%, 10%, 15%, 20%, 25%, 30%, 40%, 50%, 60%, 70%, 80%, or at least 90% modified bases. In some instances, a polynucleotide comprises no more than 1%, 5%, 10%, 15%, 20%, 25%, 30%, 40%, 50%, 60%, 70%, 80%, or no more than 90% modified bases. In some instances, a polynucleotide comprises 1-99%, 1-90%, 1-80%, 1-70%, 1-50%, 1-25%, 1-20%, 1-25%, 1-20%, 1-15%, 1-10%, 1-5%, 5-50%, 5-40%, 5-30%, 5-20%, 10-90%, 10-75%, 10-50%, 10-25%, 20-90%, 20-70%, 20-50%, 30-90%, 30-70%, 30-50%, 40-90%, 40-80%, 40-60%, 50-90%, 50-80%, 50-70%, 60-90%, 60-80%, or 70-90% modified bases. In some instances, specific regions of a polynucleotide comprise one or more modified bases.

Polynucleotides may comprise one or more regions. In some instances, a region comprises an adapter sequence. In some instances, a first region comprises an adapter sequence. In some instances, a first region comprises an adapter sequence located on the 5' terminus of a polynucleotide. In some instances, a third region comprises an adapter sequence located on the 3' terminus of a polynucleotide. In some instances, a polynucleotide comprises a first adapter sequence at a 5' terminus and a second adapter sequence at a 3' terminus. In some instances, the adapter sequence is not present in a second region. In some instances, a second region comprises an insert. In some instances an insert comprises synthetic DNA for cloning or assembly. In some instances an adapter sequence is 10-300, 10-200, 10-100, 10-80, 10-50, 20-200, 20-150, 20-100, 20-80, 20-60, 35-50, 50-75, 50-100, 50-125, or 50-150 bases in length. In some instances an insert sequence is 10-300, 10-200, 10-100, 10-80, 10-50, 20-200, 20-150, 20-100, 20-80, 20-60, 35-50, 50-75, 50-100, 50-125, or 50-150 bases in length. In some instances a second region does not comprise an endonuclease cleavage site. In some instances, the 5' adapter is different from the 3' adapter. In some instances, the adapter comprises a sequence set forth in SEQ ID NO: 1 (CCATGTGCTCACGTCTCA) or reverse complement thereof or SEQ ID NO: 2 (AGTCAGGATGTCGTCTCG) or a reverse complement thereof. In some instances, the 5' adapter comprises a sequence set forth in SEQ ID NO: 1. In some instances, the 3' adapter comprises a sequence set forth in SEQ ID NO: 2. In some embodiments, the adapter comprises a sequence comprising at least or about 70%, 80%, 85%, 90%, 91%, 92%, 93%, 94%, 95%, 96%, 97%, 98%, 99%, or 100% sequence identity to any one of SEQ ID NOs: 1-2, or a reverse complement thereof. In some instances, the adapter comprises a sequence comprising at least or about 95% homology to any one of SEQ ID NOs: 1-2, or the reverse complement thereof. In some instances, the adapter comprises a sequence comprising at least or about 97% homology to any one of SEQ ID NOs: 1-2, or the reverse complement thereof. In some instances, the adapter comprises a sequence comprising at least or about 99% homology to any one of SEQ ID NOs: 1-2, or the reverse complement thereof. In some instances, the adapter comprises a sequence comprising at least or about 100% homology to any one of SEQ ID NOs: 1-2, or the reverse complement thereof. In some instances, the adapter comprises a sequence comprising at least a portion having at least or about 3, 4, 5, 6, 7, 8, 9, 10, 12, 14, 16, 17, 18 or more than 18 nucleotides of any one of SEQ ID NOs: 1-2, or the reverse complement thereof.

Polynucleotides may have any number of different structures suitable for applications such as assembly and/or cloning. In some instances, a polynucleotide is double stranded. In some instances, a polynucleotide is single stranded. In some instances, a polynucleotide a polynucleotide is linear. In some instances, linear polynucleotides comprise one or more overlapping regions. In some instances, linear polynucleotides are configured for assembly. In some instances, a polynucleotide is circular. In some instances, a circular polynucleotide comprise a first region and a third region comprising at least one endonuclease cleavage site. In some instances, a plurality of polynucleotides are cloned into a single vector using a ligation reaction. In some instances, a ligation reaction comprises reagents (e.g., polymerase, ligase, etc.) used in the Golden Gate Assembly (NEB) method.

Provided herein are methods for amplifying nucleic acids. In some instances, a method of amplifying nucleic acids comprises one or more steps of contacting a plurality of polynucleotides with at least one primer and generating amplicons by amplifying the plurality of polynucleotides in the presence of a polymerase and at least one nucleotide comprising a modified bases. In some instances, amplicon polynucleotides described herein are generated by the amplification reaction. In some instances, a modified base reduce the efficiency of cleavage at the at least one endonuclease cleavage site. In some instances, each of the polynucleotides comprises a first endonuclease site. Amplicons in some instances, comprise a first region and a second region. In some instances, an amplicon comprises a first region comprising at least one endonuclease cleavage site; and a second region comprising at least one modified base, wherein the modified base reduces the efficiency of cleavage at the at least one endonuclease cleavage site. In some instances a method for nucleic acid amplification, comprises contacting a plurality of polynucleotides with at least one primer, wherein each of the polynucleotides comprises a first endonuclease site; and generating amplicons by amplifying the plurality of polynucleotides in the presence of a polymerase and at least 5% nucleotides comprising modified bases, wherein the modified bases reduce the efficiency of cleavage at the at least one endonuclease cleavage site.

Amplification methods may comprise any number of cycles. Cycles in some instances comprise traditional PCR cycles, but also encompass isothermal methods of nucleic acid amplification. In some instance, at least 1, 2, 5, 10, 15, 20, 25, 30, 40, or more than 45 cycles are performed. In some instance, no more than 1, 2, 5, 10, 15, 20, 25, 30, 40, or no more than 45 cycles are performed. In some instance, a single cycle is performed.

Amplification may take place in the presence of modified nucleotides, which are incorporated into amplicons. In some instances, a mixture of modified and canonical nucleotides (e.g., C, T, G, A, dC, dT, dG, dA) is used for amplification. A percentage of nucleotides in some instances describes a ratio of modified nucleotides to total nucleotides. A percentage of nucleotides in some instances describes a ratio of modified nucleotides of one type to a corresponding canonical base. In some instances, a ratio describes a ratio of a modified base to dC, dT, dG, or dA. In some instances, a ratio describes a ratio of a modified base to dC. In some instances, amplification uses 5-95, 5-90, 5-80, 5-70, 5-60, 5-50, 5-40, 5-30, 5-20, 5-10, 10-90, 10-80, 10-70, 10-60, 10-50, 10-40, 10-30, 20-90, 20-80, 20-70, 20-50, 30-90, 30-80, 30-70, 30-50, 40-90, 40-80, 40-70, 30-60, 30-50, 40-90, 40-80, 40-70, 40-60, 50-95, 50-90, 50-80, 50-90, 50-70, or 60% nucleotides comprising modified bases. In some instances, amplification uses 5-95, 5-90, 5-80, 5-70, 5-60, 5-50, 5-40, 5-30, 5-20, 5-10, 10-90, 10-80, 10-70, 10-60, 10-50, 10-40, 10-30, 20-90, 20-80, 20-70, 20-50, 30-90, 30-80, 30-70, 30-50, 40-90, 40-80, 40-70, 30-60, 30-50, 40-90, 40-80, 40-70, 40-60, 50-95, 50-90, 50-80, 50-90, 50-70, or 60% nucleotides comprising modified cytosine bases. In some instances, amplification uses 5-95, 5-90, 5-80, 5-70, 5-60, 5-50, 5-40, 5-30, 5-20, 5-10, 10-90, 10-80, 10-70, 10-60, 10-50, 10-40, 10-30, 20-90, 20-80, 20-70, 20-50, 30-90, 30-80, 30-70, 30-50, 40-90, 40-80, 40-70, 30-60, 30-50, 40-90, 40-80, 40-70, 40-60, 50-95, 50-90, 50-80, 50-90, 50-70, or 60% nucleotides comprising methyl deoxycytosine.

Methods provided herein may comprises additional steps. In some instances, a method (e.g., amplification) comprises cleavage of one or more regions of a polynucleotide. In some instances, a method comprises contacting the amplicons with an endonuclease configured to cleave the at least one endonuclease cleavage site. In some instances, an endonuclease comprises a Type IIS restriction enzyme. In some instances, a Type IIS restriction enzyme is selected from the group consisting of AcuI, AlwI, BaeI, BbsI, BbvI, BccI, BceAI, BcgI, BciVI, BcoDI, BfuAI, BmrI, BpmI, BpuEI, BsaI, BsaXI, BseRI, BsgI, BsmAI, BsmBI, BsmFI, BsmI, BspCNI, BspMI, BspQI, BsrDI, BsrI, BtgZI, BtsCI, BtsI, BtsIMutI, CspCI, EarI, EciI, Esp3I, FauI, FokI, HgaI, HphI, HpyAV, MboII, MlyI, MmeI, MnlI, NmeAIII, PleI, SapI, and SfaNI. In some instances, a Type IIS restriction enzyme comprises BsmBI.

Amplification may comprise use of one or more primers. In some instances, primers are configured to bind to one or more regions of the polynucleotides (e.g., a first or third region). In some instances, primers comprise at least one endonuclease site. In some instances, primers do not comprise a modified base. Primers in some instances comprise 5-50, 5-40, 5-30, 10-50, 10-40, 10-30, 15-40, 15-30, 20-50, 20-40, 20-30, or 30-50 bases in length.

Amplicons may be assembled into longer constructs. In some instances, one or more amplicons are assembled by overlap PCR. In some instances, one or more amplicons are assembled by ligation. Any assembly method known in the art may be used including blunt end ligation, CRISPR, gateway/transposase cloning golden gate assembly, PCA, Gibson assembly, or other assembly method. In some instances, amplicons are ligated. In some instances, ligating comprises ligation of amplicons to a vector. In some instances, a vector is transformed or transfected into a host organism. In some instances, one or more steps described herein are combined into a "one pot" or single reaction vessel reaction. In some instances, amplification, cleavage, and ligating steps of a method provided herein occur without intermediate purification. In some instances, a method described herein comprises amplifying a template nucleic acid in the presence of at least one modified base with two primers comprising an endonuclease restriction site, ligating the amplicons into a vector, and transforming or transfecting the vector into an organism.

Figure 1:
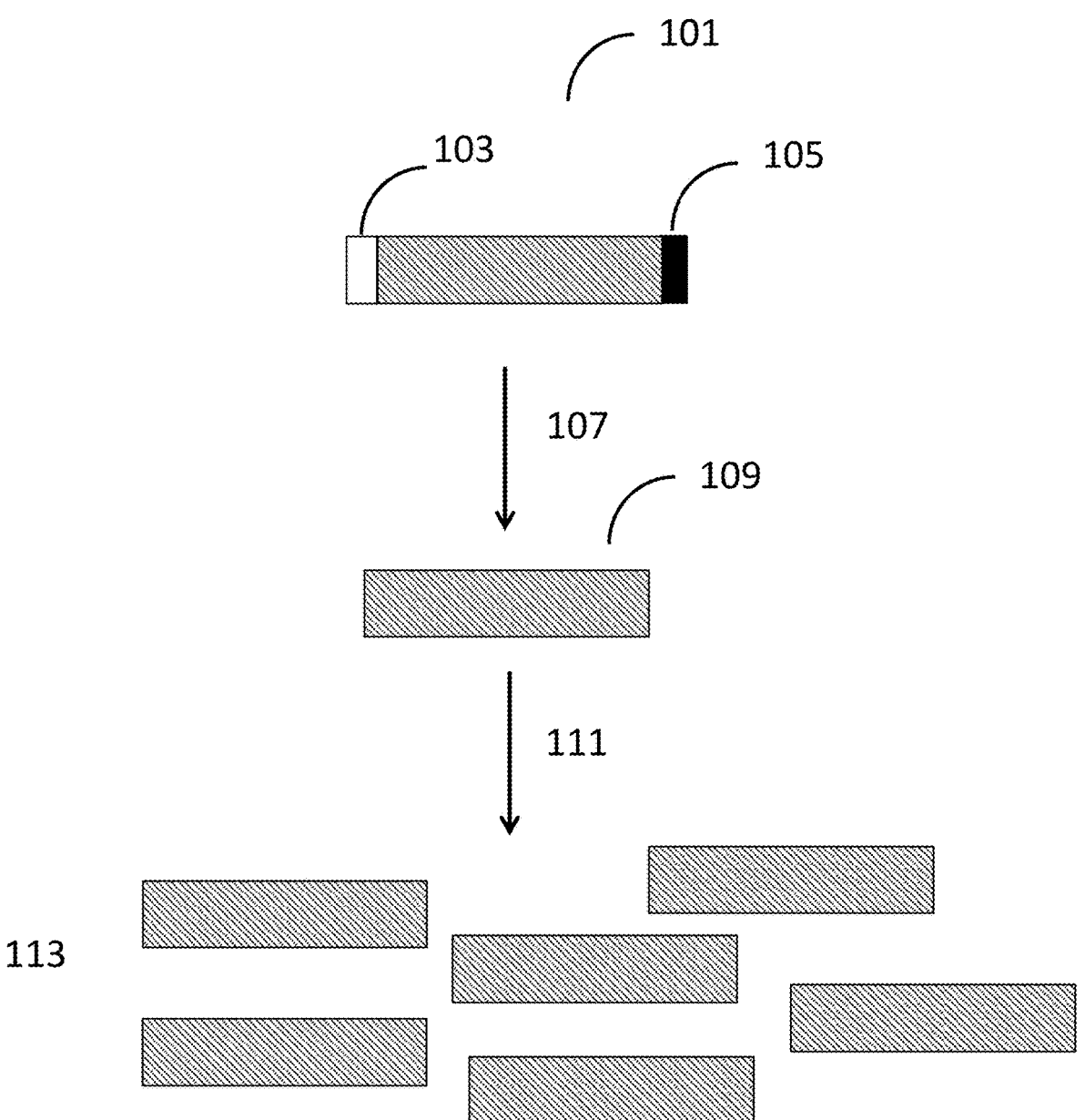
FIG. 1 depicts a general workflow for removal of adapter polynucleotides described herein.
Figure 2A:
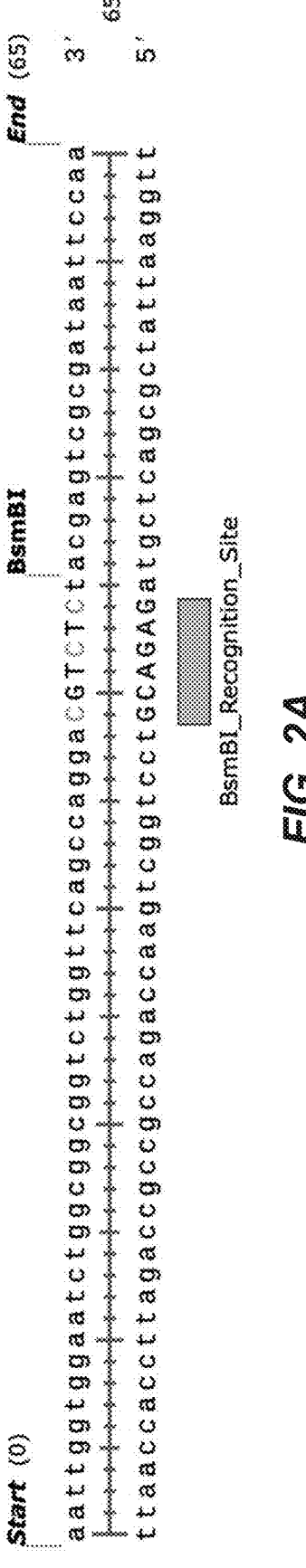
FIG. 2A depicts an exemplary sequence (SEQ ID NO:3) with a BsmBI recognition site.
Figure 2B:
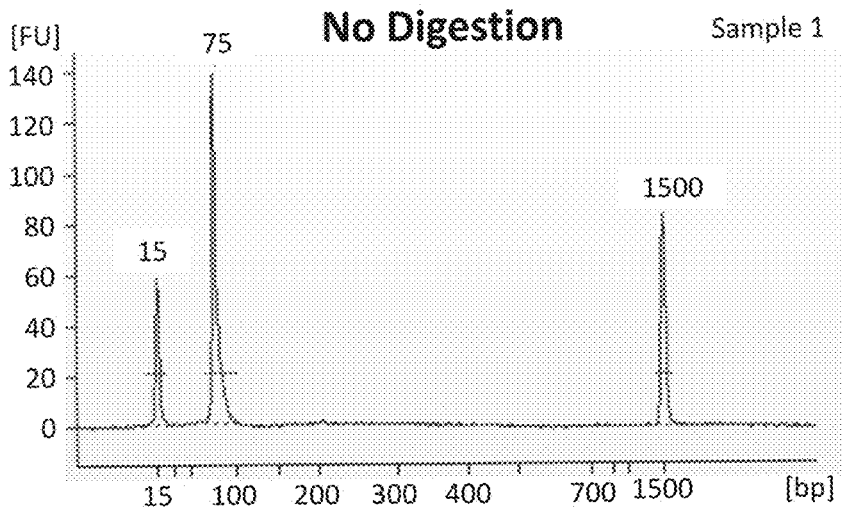
FIG. 2B shows a diagram depicting how percent restriction digestion by restriction enzyme was measured using a designed oligo duplex (FIG. 2A). Conditions shown include no digestion (left), partial digestion (middle), and complete digestion (right). The x-axis is labeled [bp] from 0 to 1500 at 15, 100, 200, 300, 400, 700, and 1500 intervals. The y-axis is labeled [FU] from 0 to 140 at 20 unit intervals (left and right graph), and −10 to 80 unit intervals (middle graph).
Figure 2B:
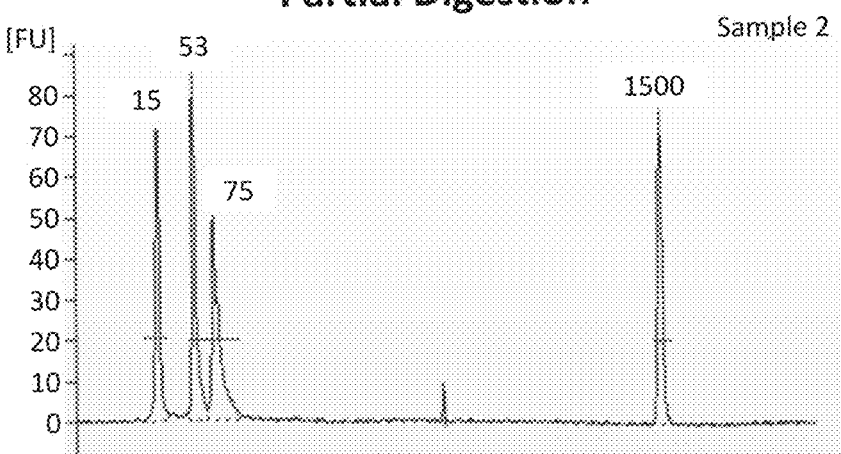
Figure 2B:
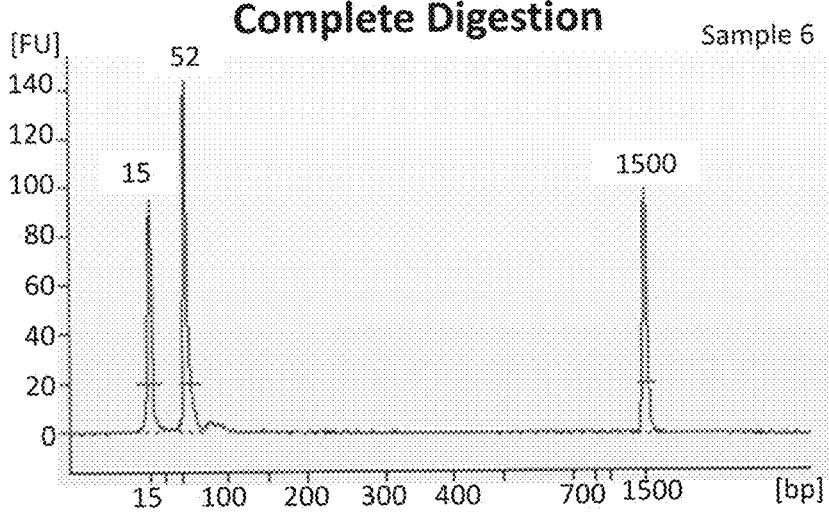

Polynucleotides provided herein may be generated using methods described herein. An exemplary process for nucleic acid assembly is seen in FIG. 1. A plurality of polynucleotides 101 are designed with 5' adapter 103 and 3' adapter 105. In some instances, the 5' adapter comprises a sequence having at least about 90% sequence identity to CCATGTGCTCACGTCTCA (SEQ ID NO: 1) or the reverse complement thereof. In some instances, the 3' adapter comprises a sequence having at least about 90% sequence identity to AGTCAGGATGTCGTCTCG (SEQ ID NO: 2) or the reverse complement thereof. The 5' adapter 103 and the 3' adapter 105 comprise forward and reverse universal flanks that comprise a restriction enzyme site. In some instances, the restriction enzyme site is a Type II endonuclease site. Exemplary Type II endonucleases include, but are not limited to, HhaI, HindIII, NotI, BbvCI, EcoRI, and BglII. In some instances, the endonuclease is a Type IIS endonuclease. Exemplary Type IIS endonucleases include, but are not limited to, AcuI, AlwI, BaeI, BbsI, BbvI, BccI, BceAI, BcgI, BciVI, BcoDI, BfuAI, BmrI, BpmI, BpuEI, BsaI, BsaXI, BseRI, BsgI, BsmAI, BsmBI, BsmFI, BsmI, BspCNI, BspMI, BspQI, BsrDI, BsrI, BtgZI, BtsCI, BtsI, BtsIMutI, CspCI, EarI, EciI, Esp3I, FauI, FokI, HgaI, HphI, HpyAV, MboII, MlyI, MmeI, MnlI, NmeAIII, PleI, SapI, and SfaNI. In some instances, the restriction enzyme is BsmBI. In some instances, the restriction enzyme site is a BsmBI restriction site. Following cleavage 107, the entire adapter is removed to generate polynucleotides without the adapters 109. The polynucleotides without the adapters 109 are then amplified. In some instances, the polynucleotides are amplified with a PCR master mix comprising about 10% to about 50% methyl-dCTP. In some instances, the PCR master mix comprise at least or about 5%, 10%, 15%, 20%, 25%, 30%, 35%, 40%, 45%, 50%, 55%, 60%, or more than 60% methyl-dCTP. In some instances, the forward and reverse primers are biotinylated and comprise the restriction site. In some instances, the forward and reverse primers are biotinylated at the 5'. In some instances, the restriction site is the BsmBI restriction enzyme site. The polynucleotides without the adapters 109 are then SPRI purified and subject to digestion, streptavidin purification to remove any uncleaved polynucleotides, collected and SPRI purified, followed by the 3' ends being filled with Klenow fragments 111 generate a plurality of polynucleotides 113 for downstream use. In some instances, digestion is a restriction enzyme digestion. In some instances, the restriction enzyme is BsmBI.

Described herein are methods of de novo synthesis for nucleic acid sequence assembly comprising removing adapters in a sequence independent-fashion. Such methods are in some instances used for the assembly of smaller nucleic acid fragments. In some instances, nucleic acid fragments comprise constant regions, variable regions, hypervariable regions, overlap regions, barcodes, regions encoding for peptide cleavage sites, regions encoding for genes or fragments of genes, restriction sites, or other regions. In some instances, nucleic acid fragments comprise gene fragments. In some instances, the fragments are at least 50, 75, 100, 125, 150, 175, 200, 250, 500, 800, 1000, 2000, 5000, 8000, 10,000, or at least 20,000 bases in length. In some instances, the fragments are no more than 50, 75, 100, 125, 150, 175, 200, 250, 500, 800, 1000, 2000, 5000, 8000, 10,000, or no more than 20,000 bases in length. In some instances, the fragments are about 50, 75, 100, 125, 150, 175, 200, 250, 500, 800, 1000, 2000, 5000, 8000, 10,000, or about 20,000 bases in length. In some instances, the fragments are 50-5000, 50-1000, 50-500, 50-250, 100-500, 200-1000, 500-10,000, 500-5,000, 1000-8000, or 1500-10,000 bases in length.

Described herein are methods for removing adapters from nucleic acids or polynucleotides. In some instances, the adapters comprise at least or about 5, 6, 7, 8, 9, 10, 11, 12, 13, 14, 15, 16, 17, 18, 19, 20, 21, 22, 23, 24, 25, 26, 27, 28, 29, 30 or more than 30 base pairs. In some instances, the adapters comprise at least or about 10, 15, 20, 25, 30, 35, 40, 45, or more than 45 base pairs. In some instances, the adapters comprise at least or about 18 base pairs.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. Typically, techniques for determining sequence identity include comparing two nucleotide or amino acid sequences and the determining their percent identity. Sequence comparisons, such as for the purpose of assessing identities, may be performed by any suitable alignment algorithm, including but not limited to the Needleman-Wunsch algorithm (see, e.g., the EMBOSS Needle aligner available at www.ebi.ac.uk/Tools/psa/emboss_needle/, optionally with default settings), the BLAST algorithm (see, e.g., the BLAST alignment tool available at blast.ncbi.nlm.nih.gov/Blast.cgi, optionally with default settings), and the Smith-Waterman algorithm (see, e.g., the EMBOSS Water aligner available at www.ebi.ac.uk/Tools/psa/emboss_water/, optionally with default settings). Optimal alignment may be assessed using any suitable parameters of a chosen algorithm, including default parameters. The "percent identity", also referred to as "percent homology", between two sequences may be calculated as the number of exact matches between two optimally aligned sequences divided by the length of the reference sequence and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, Proc. Natl. Acad. Sci. USA 87:2264-2268 (1990) and as discussed in Altschul, et al., J. Mol. Biol. 215:403-410 (1990); Karlin and Altschul, Proc. Natl. Acad. Sci. USA 90:5873-5877 (1993); and Altschul et al., Nucleic Acids Res. 25:3389-3402 (1997). Briefly, the BLAST program defines identity as the number of identical aligned symbols (i.e., nucleotides or amino acids), divided by the total number of symbols in the shorter of the two sequences. The program may be used to determine percent identity over the entire length of the sequences being compared. Default parameters are provided to optimize searches with short query sequences, for example, with the blastp program. The program also allows use of an SEG filter to mask-off segments of the query sequences as determined by the SEG program of Wootton and Federhen, Computers and Chemistry 17: 149-163 (1993). High sequence identity generally includes ranges of sequence identity of approximately 80% to 100% and integer values there between.

The adapters described herein may comprise various restriction enzyme sites to be used with various restriction enzymes. In some instances, the restriction enzyme is an endonuclease. In some instances, the restriction enzyme recognizes palindromic sequences and cleaves both strands symmetrically within the recognition sequence. In some instances, the restriction enzyme recognizes asymmetric nucleic acid sequences and cleaves both nucleic acid strands outside the recognition sequence. In some instances, the restriction enzyme comprises 1, 2, 3, 4, 5, or more than 5 cytosines that can be methylated during PCR. In some instances, the restriction enzyme comprises 1 cytosine that can be methylated during PCR. In some instances, the endonuclease is a Type II endonuclease. Exemplary Type II endonucleases include, but are not limited to, HhaI, HindIII, NotI, BbvCI, EcoRI, and BglI. In some instances, the endonuclease is a Type IIS endonuclease. Exemplary Type IIS endonucleases include, but are not limited to, AcuI, AlwI, BaeI, BbsI, BbvI, BccI, BceAI, BegI, BeiVI, BeoDI, BfuAI, BmrI, BpmI, BpuEI, BsaI, BsaXI, BseRI, BsgI, BsmAI, BsmBI, BsmFI, BsmI, BspCNI, BspMI, BspQI, BsrDI, BsrI, BtgZI, BtsCI, BtsI, BtsIMutI, CspCI, EarI, EciI, Esp3I, FauI, FokI, HgaI, HphI, HpyAV, MboII, MlyI, MmeI, MnlI, NmeAIII, PleI, SapI, and SfaNI. In some instances, the restriction enzyme is BsmBI.

The restriction site as described herein may be directly adjacent to a nucleic acid. In some instances, the restriction site is at least 1, 2, 3, 4, 5, 6, 7, 8, or more than 8 base pairs upstream of the nucleic acid. In some instances, the restriction site is at least 1, 2, 3, 4, 5, 6, 7, 8, or more than 8 base pairs downstream of the nucleic acid. In some instances, the restriction site is 1 base pair upstream or downstream of the nucleic acid. In some instances, the restriction site is 1 base pair upstream and downstream of the nucleic acid. In some instances, following cleavage at the restriction site by the restriction enzyme, a 1, 2, 3, 4, 5, 6, 7, 8, or more than 8 base pair overhang is generated. In some instances, following cleavage at the restriction site by the restriction enzyme, a 4 base pair overhang is generated. In some instances, the overhang is generated at the 5', the 3', or both.

Provided herein are methods for nucleic acid assembly comprising removal of adapters, wherein the nucleic acids or the plurality of polynucleotides are amplified in an amplification reaction. In some instances, the amplification reaction is polymerase chain reaction (PCR). In some instances, the amplification reaction is dial-out PCR. the amplification reaction comprises hybridization of a universal primer binding sequence during amplification. In some instances, the universal primer binding sequence is capable of binding the same 5' or 3' primer. In some instances, the universal primer binding sequence is shared among a plurality of target nucleic acids in the amplification reaction. In some instances, the universal primer is biotinylated. In some instances, the universal primer comprises a restriction enzyme site. In some instances, the restriction enzyme site is a BsmBI.

The amplification reaction may comprise using reagents supplemented with methyl-dCTP. In some instances, the amplification reaction comprises using a PCR master mix comprising about 10% to about 50% methyl-dCTP or about 20% to about 40% methyl-dCTP. In some instances, the PCR master mix comprise at least or about 5%, 10%, 15%, 20%, 25%, 30%, 35%, 40%, 45%, 50%, 55%, 60%, or more than 60% methyl-dCTP.

In some instances, the nucleic acids or the plurality of polynucleotides is mixed with a polymerase. In some instances, the polymerase is a DNA polymerase. In some instances, the polymerase is a high fidelity polymerase. A high fidelity polymerase may include polymerases that result in accurate replication or amplification of a template nucleic acid. In some instances, the DNA polymerase is a thermostable DNA polymerase. The DNA polymerase may be from any family of DNA polymerases including, but not limited to, Family A polymerase, Family B polymerase, Family C polymerase, Family D polymerase, Family X polymerase, and Family Y polymerase. In some instances, the DNA polymerase is from a genus including, but not limited to, Thermus, Bacillus, Thermococcus, Pyrococcus, Aeropyrum, Aquifex, Sulfolobus, Pyrolobus, or Methanopyrus.

Polymerases described herein for use in an amplification reaction may comprise various enzymatic activities. Polymerases are used in the methods of the invention, for example, to extend primers to produce extension products. In some instances, the DNA polymerase comprises 5' to 3' polymerase activity. In some instances, the DNA polymerase comprises 3' to 5' exonuclease activity. In some instances, the DNA polymerase comprises proofreading activity. Exemplary polymerases include, but are not limited to, DNA polymerase (I, II, or III), T4 DNA polymerase, T7 DNA polymerase, Bst DNA polymerase, Bca polymerase, Vent DNA polymerase, Pfu DNA polymerase, and Taq DNA polymerase. Non-limiting examples of thermostable DNA polymerases include, but are not limited to, Taq, Phusion® DNA polymerase, Q5® High Fidelity DNA Polymerase, LongAmp® DNA polymerase, Expand High Fidelity polymerase, HotTub polymerase, Pwo polymerase, Tfl polymerase, Tli polymerase, UlTma polymerase, Pfu polymerase, KOD DNA polymerase, JDF-3 DNA polymerase, PGB-D DNA polymerase, Tgo DNA polymerase, Pyrolobus furmarius DNA polymerase, Vent polymerase, and Deep Vent polymerase.

Methods described herein for nucleic acid assembly may comprise a ligation reaction. One example of a ligation reaction is polymerase chain assembly (PCA). In some instances, at least of a portion of the polynucleotides are designed to include an appended region that is a substrate for universal primer binding. For PCA reactions, the presynthesized polynucleotides include overlaps with each other (e.g., 4, 20, 40 or more bases with overlapping sequence). During the polymerase cycles, the polynucleotides anneal to complementary fragments and then are filled in by polymerase. Each cycle thus increases the length of various fragments randomly depending on which polynucleotides find each other. Complementarity amongst the fragments allows for forming a complete large span of double-stranded DNA. In some instances, after the PCA reaction is complete, an error correction step is conducted using mismatch repair detecting enzymes to remove mismatches in the sequence. Methods in some instances comprise simultaneous cleavage/amplification and ligation of one or more polynucleotides into a vector (e.g., Golden Gate Assembly, NEB).

Methods described herein for nucleic acid assembly may comprise a second restriction enzyme digestion stem. In some instances, the restriction enzyme is an endonuclease. In some instances, the restriction enzyme recognizes palindromic sequences and cleaves both strands symmetrically within the recognition sequence. In some instances, the restriction enzyme recognizes asymmetric nucleic acid sequences and cleaves both nucleic acid strands outside the recognition sequence. In some instances, the restriction enzyme comprises 1, 2, 3, 4, 5, or more than 5 cytosines that can be methylated during PCR. In some instances, the restriction enzyme comprises 1 cytosine that can be methylated during PCR. In some instances, the endonuclease is a Type II endonuclease. Exemplary Type II endonucleases include, but are not limited to, HhaI, HindIII, NotI, BbvCI, EcoRI, and BgII. In some instances, the endonuclease is a Type IIS endonuclease. Exemplary Type IIS endonucleases include, but are not limited to, AcuI, AlwI, BaeI, BbsI, BbvI, BccI, BceAI, BcgI, BciVI, BcoDI, BfuAI, BmrI, BpmI, BpuEI, BsaI, BsaXI, BseRI, BsgI, BsmAI, BsmBI, BsmFI, BsmI, BspCNI, BspMI, BspQI, BsrDI, BsrI, BtgZI, BtsCI, BtsI, BtsIMutI, CspCI, EarI, EciI, Esp3I, FauI, FokI, HgaI, HphI, HpyAV, MboII, MlyI, MmeI, MnlI, NmeAIII, PleI, SapI, and SfaNI. In some instances, the restriction enzyme is BsmBI.

Methods described herein for nucleic acid assembly may comprise a purification step. In some instances, the purification step comprises binding of the polynucleotides to a matrix. In some instances, the matrix comprises silica, cellulose, or ions. In some instances, the purification step comprises use of streptavidin. In some instances, the purification step removes any uncleaved DNA.

Provided herein are methods for nucleic acid assembly that may comprise an error correction step. Error correction may be performed on synthesized polynucleotides and/or assembled products. An example strategy for error correction involves site-directed mutagenesis by overlap extension PCR to correct errors, which is optionally coupled with two or more rounds of cloning and sequencing. In certain instances, double-stranded nucleic acids with mismatches, bulges and small loops, chemically altered bases and/or other heteroduplexes are selectively removed from populations of correctly synthesized nucleic acids. In some instances, error correction is performed using proteins/enzymes that recognize and bind to or next to mismatched or unpaired bases within double-stranded nucleic acids to create a single or double-strand break or to initiate a strand transfer transposition event. Non-limiting examples of proteins/enzymes for error correction include endonucleases (T7 Endonuclease I, *E. coli* Endonuclease V, T4 Endonuclease VII, mung bean nuclease, Cell, *E. coli* Endonuclease IV, UVDE), restriction enzymes, glycosylases, ribonucleases, mismatch repair enzymes, resolvases, helicases, ligases, antibodies specific for mismatches, and their variants. Examples of specific error correction enzymes include T4 endonuclease 7, T7 endonuclease 1, S1, mung bean endonuclease, MutY, MutS, MutH, MutL, cleavase, CELI, and HINF1. In some instances, DNA mismatch-binding protein MutS (*Thermus aquaticus*) is used to remove failure products from a population of synthesized products. In some instances, error correction is performed using the enzyme Correctase. In some instances, error correction is performed using SURVEYOR endonuclease (Transgenomic), a mismatch-specific DNA endonuclease that scans for known and unknown mutations and polymorphisms for heteroduplex DNA.

The resulting nucleic acids can be verified. In some cases, the nucleic acids are verified by sequencing. In some instances, the nucleic acids are verified by high-throughput sequencing such as by next generation sequencing. Sequencing of the sequencing library can be performed with any appropriate sequencing technology, including but not limited to single-molecule real-time (SMRT) sequencing, Polony sequencing, sequencing by ligation, reversible terminator sequencing, proton detection sequencing, ion semiconductor sequencing, nanopore sequencing, electronic sequencing, pyrosequencing, Maxam-Gilbert sequencing, chain termination (e.g., Sanger) sequencing, +S sequencing, or sequencing by synthesis.

Methods as described herein, in some embodiments, result in generation of libraries comprising at least or about $10^1$, $10^2$, $10^1$, $10^4$, $10^5$, $10^6$, $10^7$, $10^8$, $10^9$, $10^{10}$, or more than $10^{10}$ variants. In some instances, sequences for each variant of the libraries comprising at least or about $10^1$, $10^2$, $10^1$, $10^4$, $10^5$, $10^6$, $10^7$, $10^8$, $10^9$, or $10^{10}$ variants are known. In some instances, the libraries comprise a predicted diversity of variants. In some instances, the diversity represented in the libraries is at least or about 60%, 65%, 70%, 75%, 80%, 85%, 90%, 95%, or more than 95% of the predicted diversity. In some instances, the diversity represented in the libraries is at least or about 70% of the predicted diversity. In some instances, the diversity represented in the libraries is at least or about 80% of the predicted diversity. In some instances, the diversity represented in the libraries is at least or about 90% of the predicted diversity. In some instances, the diversity represented in the libraries is at least or about 99% of the predicted diversity. As described herein the term "predicted diversity" refers to a total theoretical diversity in a population comprising all possible variants.

Nucleic acid assembly using methods as described herein may efficiently assemble fragments despite high GC content, direct repeats, or secondary structures. In some instances, the fragments for assembly comprise GC content of at least or about 5%, 10%, 15%, 20%2, 25%, 30%, 35%, 40%, 45%, 50%, 60%, 65%, 70%, 75%, 80%, 85%, 90%, 95%, or more than 95%. In some instances, the fragments for assembly comprise at least or about 10, 15, 20, 25, 30, 35, 40, 45, 50, 55, 60, 65, 70, 75, or 80 base pairs (bp) adjacent direct repeats. In some instances, the fragments for assembly comprise secondary structures such as hairpin structures with dG values of at least or about −5, −6, −7, −8, −9, −10, −11, −12, −13, −14, −15, −16, −17, −18, −19, −20, −21, −22, −23, −24, −25, or −26 dG. In some instances, the fragments for assembly comprise secondary structures such as hairpin structures with dG values in a range of about −11 to about −18 dG.

Provided herein are methods for assembly of highly uniform libraries of nucleic acids. In some cases, more than about 80% of synthesized of nucleic acids (RNA or DNA) are represented within 5× of the mean for nucleic acid representation for a nucleic acid library. In some cases, more than about 90% of synthesized of nucleic acids (RNA or DNA) are represented within 5× of the mean for nucleic acid representation for a nucleic acid library. In some cases, more than about 90% of nucleic acids are represented within 2× of the mean for nucleic acid representation for the library. In some cases, more than about 90% of nucleic acids are represented within 1.5× of the mean for nucleic acid representation for the library. In some cases, more than about 80% of nucleic acids are represented within 1.5× of the mean for nucleic acid representation for the library.

Nucleic acid libraries assembled by methods described herein comprise a high percentage of correct sequences compared to predetermined sequences. In some instances, nucleic acids libraries disclosed herein have greater than 70% correct sequence compared to predetermined sequences for nucleic acids. In some instances, nucleic acids libraries disclosed herein have greater than 75% correct sequence compared to predetermined sequences for the nucleic acids. In some instances, nucleic acids libraries disclosed herein have greater than 80% correct sequence compared to predetermined sequences for the nucleic acids. In some instances, nucleic acids libraries disclosed herein have greater than 85% correct sequence compared to predetermined sequences for the nucleic acids. In some instances, nucleic acids libraries disclosed herein have greater than 90% correct sequence compared to predetermined sequences for the nucleic acids. In some instances, nucleic acids libraries disclosed herein have greater than 95% correct sequence compared to predetermined sequences for the nucleic acids. In some instances, nucleic acids libraries disclosed herein have greater than 100% correct sequence compared to predetermined sequences for the nucleic acids.

In some instances, nucleic acids libraries disclosed herein have greater than 70% correct sequence compared to predetermined sequences for the nucleic acids following an amplification reaction. In some instances, nucleic acids libraries disclosed herein have greater than 75% correct sequence compared to predetermined sequences for the nucleic acids following an amplification reaction. In some instances, nucleic acids libraries disclosed herein have greater than 80% correct sequence compared to predetermined sequences for the nucleic acids following an amplification reaction. In some instances, nucleic acids libraries disclosed herein have greater than 85% correct sequence compared to predetermined sequences for the nucleic acids following an amplification reaction. In some instances, nucleic acids libraries disclosed herein have greater than 90% correct sequence compared to predetermined sequences for the nucleic acids following an amplification reaction. In some instances, nucleic acids libraries disclosed herein have greater than 95% correct sequence compared to predetermined sequences for the nucleic acids following an amplification reaction. In some instances, nucleic acids libraries disclosed herein have 100% correct sequence compared to predetermined sequences for the nucleic acids following an amplification reaction.

Provided herein are nucleic acid libraries having high uniformity following amplification. In some instances, more than 80% of nucleic acids are represented within at least about 1.5× the mean representation for the entire library following amplification. In some instances, more than 90% of nucleic acids described herein are represented within at least about 1.5× the mean representation for the entire library following amplification. In some instances, more than 80% of nucleic acids are represented within at least about 2× the mean representation for the entire library following amplification. In some instances, more than 80% of nucleic acids are represented within at least about 2× the mean representation for the entire library following amplification.

Nucleic acid assembly using methods as described herein may result in libraries of nucleic acids comprising low error rate, low dropout rate, low runaway, low percentage of chimeric genes, or a combination thereof. In some instances, libraries of nucleic acids assembled using methods described herein comprise base insertion, deletion, substitution, or total error rates that are under 1/300, 1/400, 1/500, 1/600, 1/700, 1/800, 1/900, 1/1000, 1/1250, 1/1500, 1/2000, 1/2500, 1/3000, 1/4000, 1/5000, 1/6000, 1/7000, 1/8000, 1/9000, 1/10000, 1/12000, 1/15000, 1/20000, 1/25000, 1/30000, 1/40000, 1/50000, 1/60000, 1/70000, 1/80000, 1/90000, 1/100000, 1/125000, 1/150000, 1/200000, 1/300000, 1/400000, 1/500000, 1/600000, 1/700000, 1/800000, 1/900000, 1/1000000, or less, across the library, or across more than 80%, 85%, 90%, 93%, 95%, 96%, 97%, 98%, 99%, 99.5%, 99.8%, 99.9%, 99.95%, 99.98%, 99.99%, or more of the library. In some instances, libraries of nucleic acids assembled using methods described herein result in less than 1.0%, 1.5%, 2.0%, 2.5%, 3.0%, 3.5%, 4.0%, 4.5%, 5.0%, 6.0%, 6.5%, 7.0%, 7.5%, 8.0%, 8.5%, 9.0%, 9.5%, or 10% AT dropout. In some instances, libraries of nucleic acids assembled using methods described herein result in less than 1.0%, 1.5%, 2.0%, 2.5%, 3.0%, 3.5%, 4.0%, 4.5%, or 5.0% AT dropout. In some instances, libraries of nucleic acids assembled using methods described herein result in less than 1.0%, 1.5%, 2.0%, 2.5%, 3.0%, 3.5%, 4.0%, 4.5%, 5.0%, 6.0%, 6.5%, 7.0%, 7.5%, 8.0%, 8.5%, 9.0%, 9.5%, or 10% GC dropout. In some instances, libraries of nucleic acids assembled using methods described herein result in less than 1.0%, 1.5%, 2.0%, 2.5%, 3.0%, 3.5%, 4.0%, 4.5%, or 5.0% GC dropout. In some instances, libraries of nucleic acids assembled using methods described herein comprise at most 1.0%, 1.5%, 2.0%, 2.5%, 3.0%, 3.5%, 4.0%, 4.5%, 5.0%, 6.0%, 6.5%, 7.0%, 7.5%, 8.0%, 8.5%, 9.0%, 9.5%, or 10% of chimeric genes.

Methods of Use

Described herein are methods and compositions for nucleic acid assembly, wherein the methods are used for assembly of nucleic acids to generate libraries collectively encoding for one or more genes or gene fragments. In some instances, the libraries are combinatorial libraries, saturation libraries, or combinations thereof. In some instances, the one or more genes or gene fragments are associated with a disease or disorder.

Provided herein are methods and compositions for assembly of synthetic (i.e. de novo synthesized) genes comprising a 5' and 3' adapters associated with a disease or disorder. In some instances, the genes comprise variant modifications associated with a disease or disorder. Exemplary diseases include, but are not limited to, cancer, inflammatory diseases or disorders, a metabolic disease or disorder, a cardiovascular disease or disorder, a respiratory disease or disorder, pain, a digestive disease or disorder, a reproductive disease or disorder, an endocrine disease or disorder, or a neurological disease or disorder. In some instances, the disease or disorder is cancer. In some instances, the cancer is a solid cancer or a hematologic cancer. In some instances, the methods and compositions for assembly of genes are used to mimic cell free DNA (cfDNA) obtained from a biopsy of a cancer tumor.

Methods and compositions described herein for nucleic acid assembly may improve representation and distribution. Exemplary negative effects on representation due to repeated synthesis of large polynucleotide populations include, without limitation, amplification bias resulting from high/low GC content, repeating sequences, trailing adenines, secondary structure, affinity for target sequence binding, or modified nucleotides in the polynucleotide sequence. In some instances, methods and compositions described herein result in less dropouts, or sequences which are not detected after sequencing of amplification product. Dropouts can be of AT and/or GC. In some instances, a number of dropouts is at most about 1%, 2%, 3%, 4%, or 5% of a polynucleotide population. In some cases, the number of dropouts is zero.

In some instances, methods and compositions described herein result in a tighter distribution around the mean frequency. For example, if 100,000 reads are randomly sampled, an average of 8 reads per sequence would yield a library with a distribution of about 1.5× from the mean frequency. In some instances, methods and compositions described herein results in at most about 1.5×, 1.6×, 1.7×, 1.8×, 1.9×, or 2.0× from the mean frequency. In some instances, methods and compositions described herein results in at least about 10×, 1.2×, 1.3×, 1.5× 1.6×, 1.7×, 1.8×, 1.9×, 2.0×, 2.5×, 3.0×, 3.5×, or 4.0× from the mean frequency.

In some instances, the polynucleotide library is synthesized with a specified distribution of desired polynucleotide sequences. In some instances, adjusting polynucleotide libraries for enrichment of specific desired sequences results in improved downstream application outcomes.

Selected sequences in a polynucleotide library can be at least 10%, 20%, 30%, 40%, 50%, 60%, 70%, 80%, 90%, 95%, or more than 95% of the sequences. In some instances, selected sequences in a polynucleotide library are at most 10%, 20%, 30%, 40%, 50%, 60%, 70%, 80%, 90%, 95%, or at most 100% of the sequences. In some cases, selected sequences are in a range of about 5-95%, 10-90%, 30-80%, 40-75%, or 50-70% of the sequences.

Polynucleotide libraries described herein can be adjusted for the frequency of each selected sequence. In some instances, polynucleotide libraries favor a higher number of selected sequences. For example, a library is designed where increased polynucleotide frequency of selected sequences is in a range of about 40% to about 90%. In some instances, polynucleotide libraries contain a low number of selected sequences. For example, a library is designed where increased polynucleotide frequency of the selected sequences is in a range of about 10% to about 60%. A library can be designed to favor a higher and lower frequency of selected sequences. In some instances, a library favors uniform sequence representation. For example, polynucleotide frequency is uniform with regard to selected sequence frequency, in a range of about 10% to about 90%. In some instances, a library comprises polynucleotides with a selected sequence frequency of about 10% to about 95% of the sequences.

Systems for Nucleic Acid Sequence Assembly

Polynucleotide Synthesis

Provided herein are methods for nucleic acid sequence assembly of nucleic acids following generation of polynucleotides by de novo synthesis by methods described herein. An exemplary workflow can comprise a computer readable input file comprising a nucleic acid sequence is received. A computer processes the nucleic acid sequence to generate instructions for synthesis of the polynucleotide sequence or a plurality of polynucleotide sequences collectively encoding the nucleic acid sequence. Instructions are transmitted to a material deposition device for synthesis of the plurality of polynucleotides based on the plurality of nucleic acid sequences. The material deposition device, such as a polynucleotide acid synthesizer, is designed to release reagents in a step wise fashion such that multiple polynucleotides extend, in parallel, one residue at a time to generate oligomers with a predetermined nucleic acid sequence. The material deposition device generates oligomers on an array that includes multiple clusters of loci for polynucleotide acid synthesis and extension. However, the array need not have loci organized in clusters. For example, the loci can be uniformly spread across the array. De novo polynucleotides are synthesized and removed from the plate and an assembly reaction commenced in a collection chamber followed by formation population of longer polynucleotides. The collection chamber may comprise a sandwich of multiple surfaces (e.g., a top and bottom surface) or well or channel in containing transferred material from the synthesis surface. De novo polynucleotides can also be synthesized and removed from the plate to form a population of longer polynucleotides. The population of longer polynucleotides can then be partitioned into droplets or subject to PCR. The population of longer polynucleotides is then subject to nucleic acid assembly. In some instances, nucleic acid assembly comprises de novo synthesizing a plurality of polynucleotides comprising adapters at the 5', 3', or both. In some instances, the adapters comprise a restriction site. In some instances, the restriction site is a BsmBI restriction site. In some instances, nucleic acid assembly comprises amplifying the plurality of polynucleotide with about 5% to about 60% methyl-dCTP. Following amplification, the plurality of polynucleotides may be used for subsequent use.

Provided herein are systems for sequence assembly of nucleic acids following generation of polynucleotides by de novo synthesis by methods described herein. In some instances, the system comprises a computer, a material deposition device, a surface, and a nucleic acid assembly surface. In some instances, the computer comprises a readable input file with a nucleic acid sequence. In some instances, the computer processes the nucleic acid sequence to generate instructions for synthesis of the polynucleotide sequence or a plurality of polynucleotide sequences collectively encoding for the nucleic acid sequence. In some instances, the computer provides instructions to the material deposition device for the synthesis of the plurality of polynucleotide acid sequences. In some instances, the material deposition device deposits nucleosides on the surface for an extension reaction. In some instances, the surface comprises a locus for the extension reaction. In some instances, the locus is a spot, well, microwell, channel, or post. In some instances, the plurality of polynucleotide acid sequences is synthesized following the extension reaction. In some instances, the plurality of polynucleotide acid sequences is removed from the surface and prepared for nucleic acid assembly. In some instances, the nucleic acid assembly comprises barcode immunoglobulin sequence assembly.

A workflow for the synthesis of nucleic acids (e.g., genes) from shorter nucleic acids can be divided generally into phases: (1) de novo synthesis of a single stranded nucleic acid library, (2) joining nucleic acids to form larger fragments, (3) error correction, (4) quality control, and (5) shipment. Prior to de novo synthesis, an intended nucleic acid sequence or group of nucleic acid sequences is preselected. For example, a group of genes is preselected for generation.

Once large nucleic acids for generation are selected, a predetermined library of nucleic acids is designed for de novo synthesis. Various suitable methods are known for generating high density polynucleotide arrays. In the workflow example, a device surface layer is provided. In the example, chemistry of the surface is altered in order to improve the polynucleotide synthesis process. Areas of low surface energy are generated to repel liquid while areas of high surface energy are generated to attract liquids. The surface itself may be in the form of a planar surface or contain variations in shape, such as protrusions or microwells which increase surface area. In the workflow example, high surface energy molecules selected serve a dual function of supporting DNA chemistry, as disclosed in International Patent Application Publication WO/2015/021080, which is herein incorporated by reference in its entirety.

In situ preparation of polynucleotide arrays is generated on a solid support and utilizes single nucleotide extension process to extend multiple oligomers in parallel. A deposition device, such as a material deposition device, is designed to release reagents in a step wise fashion such that multiple polynucleotides extend, in parallel, one residue at a time to generate oligomers with a predetermined nucleic acid sequence. In some instances, polynucleotides are cleaved from the surface at this stage. Cleavage includes gas cleavage, e.g., with ammonia or methylamine.

The generated polynucleotide libraries are placed in a reaction chamber. In this exemplary workflow, the reaction chamber (also referred to as "nanoreactor") is a silicon coated well, containing PCR reagents and lowered onto the polynucleotide library. Prior to or after the sealing of the polynucleotides, a reagent is added to release the polynucleotides from the substrate. In the exemplary workflow, the polynucleotides are released subsequent to sealing of the nanoreactor. Once released, fragments of single stranded polynucleotides hybridize in order to span an entire long range sequence of DNA. Partial hybridization is possible because each synthesized polynucleotide is designed to have a small portion overlapping with at least one other polynucleotide in the pool.

After hybridization, a PCA reaction is commenced. During the polymerase cycles, the polynucleotides anneal to complementary fragments and gaps are filled in by a polymerase. Each cycle increases the length of various fragments randomly depending on which polynucleotides find each other. Complementarity amongst the fragments allows for forming a complete large span of double stranded DNA.

After PCA is complete, the nanoreactor is separated from the device and positioned for interaction with a device having primers for PCR. After sealing, the nanoreactor is subject to PCR and the larger nucleic acids are amplified. After PCR, the nanochamber is opened, error correction reagents are added, the chamber is sealed and an error correction reaction occurs to remove mismatched base pairs and/or strands with poor complementarity from the double stranded PCR amplification products. The nanoreactor is opened and separated. Error corrected product is next subject to additional processing steps, such as PCR and molecular bar coding, and then packaged for shipment.

In some instances, quality control measures are taken. After error correction, quality control steps include for example interaction with a wafer having sequencing primers for amplification of the error corrected product, sealing the wafer to a chamber containing error corrected amplification product, and performing an additional round of amplification. The nanoreactor is opened and the products are pooled and sequenced. After an acceptable quality control determination is made, the packaged product is approved for shipment.

In some instances, a nucleic acid generated by a workflow can be subject to mutagenesis using overlapping primers disclosed herein. In some instances, a library of primers are generated by in situ preparation on a solid support and utilize single nucleotide extension process to extend multiple oligomers in parallel. A deposition device, such as a material deposition device, is designed to release reagents in a step wise fashion such that multiple polynucleotides extend, in parallel, one residue at a time to generate oligomers with a predetermined nucleic acid sequence.

Numbered Embodiments

Provided herein are numbered embodiments 1-44. Embodiment 1. A method for nucleic acid assembly, comprising: (a) providing a plurality of polynucleotides, wherein each of the polynucleotides comprises a 5' adapter sequence comprising a Type IIS endonuclease site and a 3' adapter sequence comprising a Type IIS endonuclease site; (b) amplifying the plurality of polynucleotides using a reaction mixture comprising about 5% to about 60% methyl-dCTP; and (c) mixing the plurality of polynucleotides with a Type IIS restriction enzyme to generate a plurality of nucleic acids. Embodiment 2. The method of embodiment 1, wherein the 5' adapter comprises a length of at most 20 base pairs. Embodiment 3. The method of embodiment 1, wherein the 5' adapter comprises a length of at most 60 base pairs. Embodiment 4. The method of any one of embodiments 1-2, wherein the 3' adapter comprises a length of at most 20 base pairs. Embodiment 5. The method of any one of embodiments 1-4, wherein the 5' adapter comprises a sequence having at least about 90% sequence identity to SEQ ID NO: 1. Embodiment 6. The method of any one of embodiments 1-4, wherein the 5' adapter comprises a sequence according to SEQ ID NO: 1. Embodiment 7. The method of any one of embodiments 1-6, wherein the 3' adapter comprises a sequence having at least about 90% sequence identity to SEQ ID NO: 2. Embodiment 8. The method of any one of embodiments 1-6, wherein the 3' adapter comprises a sequence according to SEQ ID NO: 2. Embodiment 9. The method of any one of embodiments 1-8, wherein the reaction mixture comprising about 10% to about 50% methyl-dCTP. Embodiment 10. The method of any one of embodiments 1-8, wherein the reaction mixture comprising about 20% to about 40% methyl-dCTP. Embodiment 11. The method of any one of embodiments 1-10, wherein the Type IIS restriction enzyme is selected from the group consisting of AcuI, AlwI, BaeI, BbsI, BbvI, BccI, BceAI, BcgI, BciVI, BcoDI, BfuAI, BmrI, BpmI, BpuEI, BsaI, BsaXI, BseRI, BsgI, BsmAI, BsmBI, BsmFI, BsmI, BspCNI, BspMI, BspQI, BsrDI, BsrI, BtgZI, BtsCI, BtsI, BtsIMutI, CspCI, EarI, EciI, Esp3I, FauI, FokI, HgaI, HphI, HpyAV, MboII, MlyI, MmeI, MnlI, NmeAIII, PleI, SapI, and SfaNI. Embodiment 12. The method of any one of embodiments 1-10, wherein the Type IIS restriction enzyme is BsmBI. Embodiment 13. The method of any one of embodiments 1-12, wherein the plurality of polynucleotides comprises up to 100 different sequences. Embodiment 14. The method of any one of embodiments 1-12, wherein the plurality of polynucleotides comprises up to 1000 different sequences. Embodiment 15. The method of any one of embodiments 1-12, wherein the plurality of polynucleotides comprises up to 10,000 different sequences. Embodiment 16. The method of any one of embodiments 1-12, wherein the plurality of polynucleotides comprises up to 100,000 different sequences. Embodiment 17. The method of any one of embodiments 1-16, wherein the plurality of nucleic acids comprises at least 10,000 nucleic acids. Embodiment 18. The method of any one of embodiments 1-16, wherein the plurality of nucleic acids comprises at least 100,000 nucleic acids. Embodiment 19. The method of any one of embodiments 1-18, wherein at least 80% of the plurality of nucleic acids are represented within 2× of a mean frequency. Embodiment 20. The method of any one of embodiments 1-18, wherein at least 90% of the plurality of nucleic acids are represented within 2× of a mean frequency. Embodiment 21. The method of any one of embodiments 1-18, wherein at least 80% of the plurality of nucleic acids are represented within 1.5× of a mean frequency. Embodiment 22. The method of any one of embodiments 1-18, wherein at least 90% of the plurality of nucleic acids are represented within 1.5× of a mean frequency. Embodiment 23. A method for adapter removal, comprising: (a) providing a plurality of polynucleotides encoding a gene comprising one or more modifications associated with a disease or disorder, wherein each of the polynucleotides comprises a 5' adapter sequence comprising a Type IIS endonuclease site and a 3' adapter sequence comprising a Type IIS endonuclease site; (b) amplifying the plurality of polynucleotides using a reaction mixture comprising about 5% to about 60% methyl-dCTP; and (c) mixing the plurality of polynucleotides with a Type IIS restriction enzyme to generate a plurality of nucleic acids. Embodiment 24. The method of embodiment 23, wherein the disease or disorder is cancer. Embodiment 25. The method of any one of embodiments 23-24, wherein the 5' adapter comprises a length of at most 20 base pairs. Embodiment 26. The method of any one of embodiments 23-25, wherein the 3' adapter comprises a length of at most 20 base pairs. Embodiment 27. The method of any one of embodiments 23-26, wherein the 5' adapter comprises a sequence having at least about 90% sequence identity to SEQ ID NO: 1. Embodiment 28. The method of any one of embodiments 23-26, wherein the 5' adapter comprises a sequence according to SEQ ID NO: 1. Embodiment 29. The method of any one of embodiments 23-28, wherein the 3' adapter comprises a sequence having at least about 90% sequence identity to SEQ ID NO: 2. Embodiment 30. The method of any one of embodiments 23-28, wherein the 3' adapter comprises a sequence according to SEQ ID NO: 2. Embodiment 31. The method of any one of embodiments 23-30, wherein the reaction mixture comprising about 10% to about 50% methyl-dCTP. Embodiment 32. The method of any one of embodiments 23-31, wherein the reaction mixture comprising about 20% to about 40% methyl-dCTP. Embodiment 33. The method of any one of embodiments 23-32, wherein the Type IIS restriction enzyme is selected from the group consisting of AcuI, AlwI, BaeI, BbsI, BbvI, BccI, BceAI, Bcgl, BciVI, BcoDI, BfuAI, BmrI, BpmI, BpuEI, BsaI, BsaXI, BseRI, Bsgl, BsmAI, BsmBI, BsmFI, BsmI, BspCNI, BspMI, BspQI, BsrDI, BsrI, BtgZI, BtsCI, BtsI, BtsIMutI, CspCI, EarI, EciI, Esp3I, FauI, FokI, HgaI, HphI, HpyAV, MboII, MlyI, MmeI, MnlI, NmeAIII, PleI, SapI, and SfaNI. Embodiment 34. The method of any one of embodiments 23-32, wherein the Type IIS restriction enzyme is BsmBI. Embodiment 35. The method of any one of embodiments 23-34, wherein the plurality of polynucleotides comprises up to 100 different sequences. Embodiment 36. The method of any one of embodiments 23-34, wherein the plurality of polynucleotides comprises up to 1000 different sequences. Embodiment 37. The method of any one of embodiments 23-34, wherein the plurality of polynucleotides comprises up to 10,000 different sequences. Embodiment 38. The method of any one of embodiments 23-34, wherein the plurality of polynucleotides comprises up to 100,000 different sequences. Embodiment 39. The method of any one of embodiments 23-38, wherein the plurality of nucleic acids comprises at least 10,000 nucleic acids. Embodiment 40. The method of any one of embodiments 23-38, wherein the plurality of nucleic acids comprises at least 100,000 nucleic acids. Embodiment 41. The method of any one of embodiments 23-40, wherein at least 80% of the plurality of nucleic acids are represented within 2× of a mean frequency. Embodiment 42. The method of any one of embodiments 23-40, wherein at least 90% of the plurality of nucleic acids are represented within 2× of a mean frequency. Embodiment 43. The method of any one of embodiments 23-40, wherein at least 80% of the plurality of nucleic acids are represented within 1.5× of a mean frequency. Embodiment 44. The method of any one of embodiments 23-40, wherein at least 90% of the plurality of nucleic acids are represented within 1.5× of a mean frequency.

The following examples are set forth to illustrate more clearly the principle and practice of embodiments disclosed herein to those skilled in the art and are not to be construed as limiting the scope of any claimed embodiments. Unless otherwise stated, all parts and percentages are on a weight basis.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1. Restriction Digestion Assay Outline

An assay identifying the quantification of digestion by BsmBI was designed on the Bioanalyzer 1000 DNA Assay (Agilent), outlined in (FIG. 1). 65 nt oligos with a central BsmBI cut site were ordered (Integrated DNA technologies) with different internal methyl-C modifications. Complementary oligos were annealed before being utilized for in vitro digestion with BsmBI in vitro for one hour. Post-digestion double-stranded substrates were subjected to bioanalyzer analysis to look for size shift as a proxy for digestion and area under the curve was measured to quantify digestion.

Based on the electropherograms, percent digestion was determined by identifying peak sizes and area under the curve. Optimization was done with mass titration BsmBI enzyme purchased from NEB (New England Biolabs) as well as a reaction time titration. Complete digestion was observed after a three hour incubation at 55° C. An partial and complete digestion electropherogram was provided for comparison (FIGS. 1A-1C).

Example 2. Positional Inhibition of Methyl dCTP on BsmBI

Individual oligos with internal cytosine methylation modifications and a nested BsmBI restriction recognition sequence were ordered (Integrated DNA technologies) to be annealed as duplex in vitro for the production of sample substrates for test digestion with BsmBI or Esp3I. BsmBI reactions were carried out with 10 U of BsmBI in a 50 µL reaction with 1×NEBBuffer3.1. Reactions were carried out for 55° C. for three hours and 80° C. for 20 minutes for heat denaturation of enzymes. Esp3I reactions were carried out with 10 U of Esp3I in a 50 µL reaction with 1× CutSmart buffer. Reactions were carried out for 37° C. for three hours and 65° C. for 20 minutes for heat denaturation of enzymes. 1 µL of reaction was immediately loaded onto the BioAnalyzer 1000 DNA Assay and the electropherogram was used to calculate percent digestion of each substrate. Total digestion percentage of each substrate was visualized in FIG. 2 to determine an optimal amount of Me-dCTP to be added for PCR.

The assay from FIG. 6 was used to assess the cutting efficiency of BsmBI and its isoschizomer, Esp3I, on substrates with various amount of methyl-C in the recognition sequence. Substrates were treated with BsmBI for three hours at 55° C. or Esp3I for three hours at 37° C. Material was run on a bioanalyzer post-digestion and the area under the curve for the digested peak was measured as a proxy for digestion percentage.

Example 3. DNA Assembly and Cloning Assay

Figure 3:
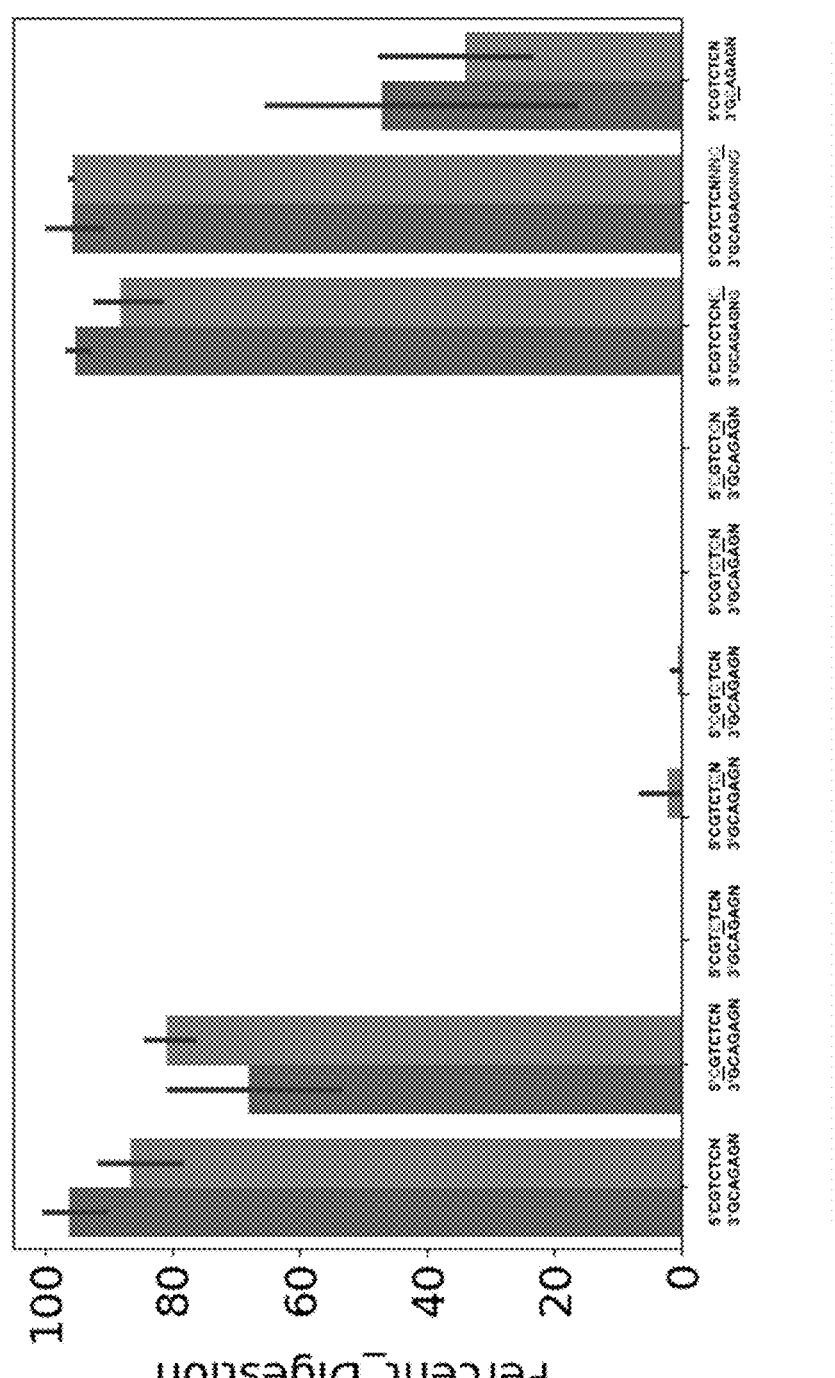
FIG. 3 summarizes percent digestion with oligo duplexes that contain different amounts and positions of methylated cytosines in the recognition sequence. Methylated cytosines are underlined. The y-axis is labeled percent digestion from 0 to 100 at 20 unit intervals. Sequences along the x-axis (left to right, 5'/3' strands, methyl C's underlined) are.

Cloning of diverse oligo pools or libraries can be done with homology based cloning but may be limited by the requirement of long and well-designed overlaps that are free of repetitive sequences or structures for overlaps and PCR primers. Restriction enzyme based cloning with Type IIs enzymes can address that requirement but are generally limited to cloning pools that do not contain the recognition sites within the library—members of the library that contain the restriction site will be cleaved risk being unable to be ligated into the vector. The methods described herein are used to block the internal recognition sites to prevent them from dropping out when cloning is done at the library level. In order to demonstrate this, an oligo pool was designed to contain members with internal BsmBI cut sites for cloning (FIG. 3).

To demonstrate application of methyl C's protection in cloning with BsmBI, an 100 k member oligo pool was designed for cloning into a vector after PCR amplification with 0% or 20% methyl-dCTP. The oligo pool was amplified and digested with BsmBI for three hours and bead purified for ligation into a gel-purified vector. The final library was transformed into *E. coli* and harvested after overnight growth, lysed for amplicon sequencing on the Miseq.

The oligo pool was designed to contain PCR primer binding sites with BsmBI recognition sites on the 5' and 3' of the oligo. Amplification with the unmethylated PCR primers allowed for BsmBI digestion on the edges of the oligo to expose sticky ends for ligation into a vector with kanamycin resistance. The oligo pool was amplified with Kapa HiFi Polymerase(Roche) for 15 cycles. dNTP mix was made by blending individual dNTP and 5-MethyldCTP (Jena Bioscience) to yield 0% or 20% 5-Methyl dCTP. The amplified oligo pool was bead purified and quality controlled with Qubit Broad Range DNA Assay (ThermoFisher) and Bioanalyzer 1000 DNA assay (FIG. 4). Amplified oligo pools were digested with BsmBI restriction enzyme for three hours at 55° C. and run on the bioanalyzer 1000 DNA assay again to assay for percent digestion (FIG. 10).

5 pmols of the library was used for digestion with BsmBI following the general protocol listed in Example 2. Library oligos were ligated into a vector and transformed into *E. coli* for overnight growth and plated with >100× library coverage (FIG. 5). Cloning efficiency of each methyl dCTP oligo pool was checked to determine potential differences in cloning efficacy. CFUs were determined post-cloning and plating on LB+kanamycin plates and back-calculated from serial dilution plating. The methyl-dCTP incorporated pool did not impact cloning efficacy.

Amplicon libraries were made from the extracted plasmid DNA from *E. coli* and sequenced on a Miseq with >100× sequencing coverage over library diversity. Amplicon reads were mapped to reference input oligos and read count data was collected. 38% of oligos containing internal BsmBI cut sites were complete dropouts from the pool that did not utilize the 5-Methyl-dCTP incorporation into amplicon. The 62% oligos may have been recovered due to potential re-ligation at low efficacy of the original digested sites. In contrast, 99.9% of the oligos containing internal BsmBI sites in the 20% 5-Methyl-dCTP was recovered and identified in the amplicon sequencing data (FIG. 6). Representation of oligos containing internal BsmBI recognition sites were calculated and analyzed. Incorporating 20% methyl dCTP was able to fully recover otherwise dropouts from not incorporating any methyl dCTP.

Example 4. Adapter-Off by PCR with Methyl-dCTP and Type IIs Restriction Enzymes A first experiment was performed using the adapter-off DNA for cfDNA.

The adapters comprised a Bsmb1 restriction site according to the following: 5'-CGTCTC(N1)-3' and 3'-GCAGAG (N4)-5'. The top strand is unmethylated by PCR with primers. An extraction plate was prepared in 20 µL water that was sealed, spun down, and sat at room temperature for 10 minutes. The dNTP master mix was prepared according to Table 1A and the thermocycle reaction was performed according to Table 1B.

TABLE 1A

| percent methyl-dCTP | 0% | 10% | 25% | 50% | 75% | 90% | 100% |
|---|---|---|---|---|---|---|---|
| dATP 10 mM | 4 | 4 | 4 | 4 | 4 | 4 | 4 |
| dGTP 10 mM | 4 | 4 | 4 | 4 | 4 | 4 | 4 |
| dTTP 10 mM | 4 | 4 | 4 | 4 | 4 | 4 | 4 |
| dCTP 10 mM | 4 | 3.6 | 3 | 2 | 1 | 0.4 | 0 |
| methyl-dCTP 10 mM | 0 | 0.4 | 1 | 2 | 3 | 3.6 | 4 |

TABLE 1B

| STEP | Temp | Time |
|---|---|---|
| Initial Denaturation | 95° C. | 3 minutes |
| 25 Cycles | 98° C. | 10 seconds |

TABLE 1B-continued

| STEP | Temp | Time |
|---|---|---|
| | 69° C. | 15 seconds |
| | 72° C. | 15 seconds |
| Final Extension | 72° C. | 2 minutes |
| Hold | 4° C. | |

From above, an 8 ng/µL yield was obtained. The yield was increased to 20 ng/µL by additional cycles at 66° C. annealing. The samples were then subject to SPRI at 2×, eluted in 22 µL, and 20 µL used for further processing. The sample were digested with BsmBI and 10 µL of dNTP master mix was added to each sample. Data is seen in FIGS. 1A-1C.

A first experiment was modified and performed similarly as above and according to Table 2A and Table 2B. Data is seen in FIG. 2. The sample were digested with BsmBI and 10 µL of dNTP master mix was added to each sample. Data is seen in FIG. 3.

TABLE 2A

| Frag 1 | 1× for 20 µL Rxn | 8× | Final Concentration |
|---|---|---|---|
| H₂O | 12.4 | 99.2 | |
| 5× Q5 buffer | 4 | 32 | 1× |
| dNTP mix 10 mM | 0.4 | 3.2 | 200 µM |
| cfDNA_bsmb1_F 10 µM | 1 | 8 | |
| cfDNA_bsmb1_R 10 µM | 1 | 8 | |
| Q5 polymerase (2 U/µl) | .2 | 1.6 | 0.02 U/µl |
| Oligos from well | 1 | 8 | |
| Total | | | |

TABLE 2B

| STEP | Temp | Time |
|---|---|---|
| Initial Denaturation | 95° C. | 3 minutes |
| 17-23 Cycles | 98° C. | 10 seconds |
| | 66° C. | 15 seconds |
| | 72° C. | 15 seconds |
| Final Extension | 72° C. | 2 minutes |
| Hold | 4° C. | |

The samples were then analyzed by mapping the cfDNA to a human reference and the polynucleotide population. The distribution of coverage across each variant was analyzed. Briefly, each variant was tiled by 20 different polynucleotides (FIG. 4A). The data and data from sequencing (data not shown) demonstrates even coverage across most variants. Similar profiles were observed between the sequencing data and the theoretical data at most sites.

The samples were also analyzed for distribution for variants with endogenous BsmBI sites. FIG. 4B shows BsmBI containing standards were substantially under-represented in the library without 5mC, but including 20% 5mCTP in the PCR reaction almost entirely removed difference.

The samples were analyzed for distribution (FIG. 4C). The distribution over each individual standard was relatively broad, with a median of 258 reads/standard, but a fairly long upper tail. While no variants were completely absent from the library, a small number (73/6360) had fewer than 10 supporting reads. The mean read counts/standard across all variants forms were relatively narrow distribution, with nearly all variants being represented by a mean number between 200 and 400 reads/standard. Thus, there appeared to be minimal systematic bias. With respect to GC content bins, most (41/73) standards were represented with fewer than 10 reads in the library belong to high GC-content bins (>=60%), so there may be some bias affecting these specific fragments (FIG. 4D).

Chimeric frequency and barcode integrity were also analyzed. In some cases, "chimeric" standards were observed that appeared to match the start and end-coordinates of two different standards, and that have the correct barcodes for two different standards to match (data not shown). Looking globally at the data, this appears to occur around 5% of the time in all three of the 5mC concentration conditions. Truncated reads (around another 7-8% of the time), which are reads that match either the start or the end of a particular standard (but not both the start and the end of any specific standard) were also observed (data not shown).

A second experiment was performed using the adapter-off DNA for cfDNA with some modifications. Experiments were performed similarly to the first experiment and accordingly to Table 3A and Table 3B.

TABLE 3A

| Master Mix | | | |
|---|---|---|---|
| Reagent | 1× | 8× | 200× |
| Kapa HiFi | 0.1 | 0.8 | 20 |
| 5× Kapa buffer | 2 | 16 | 400 |
| dNTPs | 0.2 | 1.6 | 40 |
| cfDNA_BSMB1_F (5' biotinylated) 10 uM | 1 | 8 | 200 |
| cfDNA_BSMB1_R 10 uM | 1 | 8 | 200 |
| Oligos | 1 | each | each |
| H₂O | 4.7 | 37.6 | 940 |
| Total Vol | 10 | | |

TABLE 3B

| PCR Reaction Steps | | |
|---|---|---|
| STEP | Temp | Time |
| Initial Denaturation | 95° C. | 3 minutes |
| 2 Cycles | 98° C. | 10 seconds |
| | 66° C. | 15 seconds |
| | 72° C. | 15 seconds |
| Hold | 4° C. | |

From Table 3A, 9 µL of master mix was added to each well of 384-well plate. 1 µL of sample was then added. 10 µL of the samples were added to 96-well plates with 10 µL of beads in the well. Samples were incubated for 20 minutes at RT. The supernatant was removed and the beads were washed 2× in binding buffer. The supernatant was removed. 14 µL of water was added to the beads and mixmate at 2000 rpm for 20 seconds to suspend the beads. The dNTP mix was prepared according to Table 3C and the PCR master mix was prepared according to Table 3D.

TABLE 3C

| dNTP Mix | | |
|---|---|---|
| percent methyl-dCTP | 0% | 30% |
| dATP 10 mM | 25 | 25 |
| dGTP 10 mM | 25 | 25 |
| dTTP 10 mM | 25 | 25 |
| dCTP 10 mM | 25 | 17.5 |
| methyl-dCTP 10 mM | 0 | 7.5 |

TABLE 3D

| PCR Master Mix | | | |
|---|---|---|---|
| Reagent | 1× for 20 µL Rxn | 8× | 200× |
| H₂O | 9.4 | 99.2 | 1880 |
| 5× Kapa buffer | 4 | 32 | 800 |
| dNTP mix 10 mM | 0.4 | 3.2 | 80 |
| cfDNA_bsmb1_F 10 uM | 1 | 8 | 200 |
| cfDNA_bsmb1_R 10 uM | 1 | 8 | 200 |
| Kapa HiFi | .2 | 1.6 | 40 |
| full length dsOligos on beads | 2 | each | each |
| Total | | | |

TABLE 3E

| Thermocycle Conditions | | |
|---|---|---|
| STEP | Temp | Time |
| Initial Denaturation | 98° C. | 5 minutes |
| 17-23 cycles* | 98° C. | 10 seconds |
| | 66° C. | 15 seconds |
| | 72° C. | 15 seconds |
| Final Extension | 72° C. | 2 minutes |
| Hold | 4° C. | |

18 µL of PCR Master Mix was added to each well of a 384-well plate. 2 µL of DNA on beads was added to each well. Thermocycling was performed according to Table 3E. Data is seen in FIGS. 5A-5B.

In a modified experiment of the second experiment, the columns were pooled, and SPRI was performed at 1.3× and eluted in 100 uL. The samples were digested with BsmBI. Data is seen in FIG. 5C.

Samples were analyzed for chimera and truncation rates, distribution for variants with endogenous BsmBI sites, and effects of position on representation. Data for chimera and truncation rates is seen in Table 3F. As seen in Table 3F, chimera rates were significantly reduced from Build 1 to Build 2 (from 5% of all reads to 0.6%), raising the percent of reads deriving from exact boundaries from 86% to 93%. Data for distribution for variants with endogenous BsmBI sites is seen in FIG. 5D and effects of position on representation is seen in FIG. 5E.

TABLE 3F

| Chimera and Truncation Rates | | |
|---|---|---|
| | Build 1 | Build 2 |
| Chimeras | 5.6% | 0.6% |
| Full length | 85.7% | 93.2% |
| Partial truncation | 6.0% | 5.1% |
| Full truncation | 2.6% | 1.1% |

Samples were also analyzed for uniformity and distribution. Looking at each variant, all 20 molecular barcodes were detected with at least one full-length read for about 90% of variants. A longer tail was observed for Build 2, with a handful of variants only being detected with <10 distinct barcodes (FIG. 5F). As seen in FIG. 5G that shows the mean read coverage among all supporting fragments for each variant, it was observed that the variant-to-variant coverage was much tighter in Build 2 compared to Build 1. The read counts from each fragment is seen in FIG. 5H. The samples were also repooled (FIG. 5I). The variability was improved by including a scaling factor in every well at equal representation. After this simulated re-pooling, the distribution of mean reads across each standard became tighter, and the coefficient of variability reduced for the fragments associated with each standard (FIGS. 5J-5L).

A third experiment was performed using the adapter-off DNA for cfDNA with some modifications. Experiments were performed similarly to the first and second experiment and accordingly to Tables 4A-4D.

TABLE 4A

| percent methyl-dCTP | 30% |
|---|---|
| dATP 10 mM | 250 |
| dGTP 10 mM | 250 |
| dTTP 10 mM | 250 |
| dCTP 10 mM | 175 |
| methyl-dCTP 10 mM | 75 |
| Total volume | 1 ml |

TABLE 4B

| PCR Reaction Mix | |
|---|---|
| Reagent | 1× for 25.2 µL Rxn |
| H₂O | 15.85 |
| 5× Kapa buffer | 5 |
| dNTP mix 30% mdCTP 10 mM | 0.5 |
| cfDNA_bsmb1_F 10 µM | 1.2 |
| cfDNA_bsmb1_R 10 µM | 1.2 |
| Kapa HiFi | 0.25 |
| Oligos from resuspended matrixed oligo plate | 1.2 |
| Total | 25.2 |

TABLE 4C

| PCR Reaction Mix | |
|---|---|
| Reagent | 1× for 10 µL Rxn |
| H₂O | 4.7 |
| 5× Kapa buffer | 2 |
| dNTP mix 30% mdCTP | 0.2 |
| cfDNA_bsmb1_F 10 µM | 0.5 |
| cfDNA_bsmb1_R 10 µM | 0.5 |
| Kapa HiFi | 0.1 |
| full length dsOligos on beads | 2 |

TABLE 4D

| PCR Reaction Cycles | | |
|---|---|---|
| STEP | Temp | Time |
| Initial Denaturation | 98° C. | 5 minutes |
| 35 cycles | 98° C. | 10 seconds |
| | 66° C. | 15 seconds |
| | 72° C. | 15 seconds |
| Final Extension | 72° C. | 2 minutes |
| Hold | 4° C. | |

The experiments described herein demonstrate use of adapters and methyl-dCTP for nucleic acid assembly for improving representation and distribution of the sequences generated.

Example 5. Golden Gate Cloning

A baseline was obtained for NEB BsmBI Golden Gate Assembly kit was obtained in phase I using a small oligo pool (around 5000 oligos) from Q-203241. The objective of phase II is to test the upper limit of the NEB BsmBI Golden Gate Assembly kit using a new and larger oligo pool (250,000 oligos). The oligo pool also has. uniform GC content between 30 to 80% which would allow us to better determine the degree of GC bias in Golden Gate Assembly. Undigested vector will be used in this phase since there in phase I testing no difference in background between digested and undigested vector was found. Number of cycles will continue to be experimented with to determine how many cycles is required to clone a much larger oligo pool.

Variables. Three different reaction conditions (cycle number and temperatures) were examined: 1 hr at 42 C 5 min at 60 C; (3 min at 42 C 3 min at 16 C)×20 cycles 5 min at 60 C; and (3 min at 42 C 3 min at 16 C)×40 cycles 5 min at 60 C. Quality control was measured using Gel electrophoresis: Determine the proportion of final product to unincorporated material; Transformation efficiency (CFU/ug); and NGS: Observed library diversity.

Procedure. The oligo pool was amplified using dNTP mixture with 20% methyldCTP and 80% dCTP (with both biotinylated and non-biotinylated primers) The biotinylated pool was scaled up and reconditioned to 5 ug (this was used for traditional digestion and ligation set up). The non-biotinylated pool was scaled up and reconditioned such that there is enough fmol to run the required amount of reactions (300 fmol required per reaction). 40 μL of 1.25 ng/μL non-biotinylated sample was examined by NGS. Five Esp3I digestion reaction were conducted at 37 C overnight with the biotinylated oligo pool (Table 5).

TABLE 5

| Component | Amount |
|---|---|
| 10X NEB Cutsmart buffer | 5 μL |
| Esp3I | 3 μL |
| Oligo Pool | 1000 ng |
| Water | up to 50 μL |
| Total | 50 μL |

After confirming full digestion on a bioAnalyzer the digestion was cleaned up with streptavidin beads and the supernatant run through a zymo clean up & concentrator kit.

Golden Gate Assembly reactions were set up (3 insert: 1 Vector) with non-biotinylated and undigested oligo pool using Table 6.

TABLE 6

| Treatment | Linearized Vector or Uncut Vector | Undigested Insert | T4 DNA Ligase Buffer (10×) | NEB Golden Gate Enzyme Mix | ddH20 | Total |
|---|---|---|---|---|---|---|
| Vector + Insert | 100 fmol | 300 fmol | 2 μl | 2 μl | up to 20 μl | 20 |
| Vector + Enzyme Mix Only | 100 fmol | 0 | 2 μl | 2 μl | up to 20 μl | 20 |
| Vector Only | 100 fmol | 0 | 2 μl | 0 | up to 20 μl | 20 |

After subjecting the reactions to the three treatment conditions, 5 μL of products were run on a gel followed by DNA purification (Zymo Oligo Clean and Concentrator Column).

Next, a traditional overnight ligase reaction with digested vector and oligo pool was set up according to Table 7. Each reaction was incubated overnight at 4 C, 5 μL of products were run on a gel followed by DNA purification (Zymo Oligo Clean and Concentrator Column).

TABLE 7

| Treatment | Digested Vector | Digested Insert | T4 DNA Ligase Buffer (10×) | T4 DNA Ligase | ddH20 | Total |
|---|---|---|---|---|---|---|
| Vector + Insert | 100 fmol | 300 fmol | 2 μl | 1 μl | up to 20 μl | 20 |
| Vector + Ligase Only | 100 fmol | 0 | 2 μl | 1 μl | up to 20 μl | 20 |
| Vector Only | 100 fmol | 0 | 2 μl | 0 | up to 20 μl | 20 |

Purified DNA was then transformed into *E. coli*. Cells were thawed on ice <5 mins before transformation 2 μL of ligation mixture was dispensed into 25 μL of Competent Cells.

22 μL of Competent Cells were transferred to the Electroporation Plate for Transformation. Cells were electroporated using an x_bacteria_5 program and monitored to ensure no arcing occurred. Cells were recovered in 1 ml of pre-warmed Lucigen Recovery Media for 37° C. with shaking for 1 hour. Cell dilutions were performed in a 96 well plate with 1:5 dilutions. Lennox Media Plates were pre-warmed 30 mins prior to plating, and the remainder of the cells were added to 100 ml of media and grow over night at 37° C. shaking. Cell dilutions were plated with 10 μL spots and grow overnight for 15 hours at 37° C. (or 30 C if using TG1 cells) and CFU/μg were calculated.

2 mL of the 100 ml cultures was miniprepped using the Qiagen Spin Miniprep Kit. Post cloning, 500 ng of miniprep samples was amplified for 8 cycles and 40 Cu of 1.25 ng L cleaned up PCR samples was submitted for NGS analysis.

Results. Transformation efficiency of golden gate samples and traditional digestion ligation samples reported as CFU g (Table 8). Each mean is average of four replicates (2 cloning replicates and 2 dilution replicates for each) except for traditional overnight ligations that are average of 6 replicates (3 cloning replicates and 2 dilution replicates for each). The QC results are shown in FIGS. 14A-17B and Table 9.

TABLE 8

| Description | Cloning replicate | Dilution Replicate | Mean CFU/ug | Standard Deviation |
|---|---|---|---|---|
| 1 Cycle Golden Gate with undigested vector and Insert | 2 | 1 | 2.35E+07 | 1.47E+07 |
| 1 Cycle Golden Gate with undigested vector and enzyme mix only | 2 | 2 | 1.03E+04 | 1.04E+04 |
| 20 Cycles Golden Gate with undigested vector and insert | 2 | 2 | 3.55E+07 | 2.32E+07 |
| 20 Cycle Golden Gate with undigested vector and enzyme mix only | 2 | 2 | 8.11E+03 | 5.05E+03 |
| 40 Cycles Golden Gate with undigested vector and insert | 2 | 2 | 2.57E+07 | 1.51E+07 |
| 40 Cycle Golden Gate with undigested vector and enzyme mix only | 2 | 2 | 1.17E+04 | 2.40E+03 |
| Traditional overnight Ligation with linearized vector and insert | 3 | 2 | 5.68E+06 | 3.10E+06 |
| Traditional overnight Ligation with linearized vector and ligase only | 3 | 2 | 7.09E+03 | 6.20E+03 |

TABLE 9

| Description | Mean CFU/ ug | Mean % Chimera | Mean % Full Length | Mean 95th/ 5th | Mean % dropout | Mean read count |
|---|---|---|---|---|---|---|
| 1 Cycle Golden Gate with undigested vector and Insert (FIGS. 14A-14B) | 2.35E+07 | 2.70% | 99.52% | 5.95 | 0.08% | 20.78 |
| 20 Cycles Golden Gate with undigested vector and insert (FIGS. 15A-15B) | 3.55E+07 | 2.73% | 99.49% | 5.34 | 0.07% | 19.75 |
| 40 Cycles Golden Gate with undigested vector and insert (FIGS. 16A-16B) | 2.57E+07 | 2.78% | 99.47% | 6.34 | 0.13% | 20.33 |
| Traditional overnight Ligation with linearized vector and insert (FIGS. 17A-17B) | 5.68E+06 | 2.49% | | 18 | 1.87% | 8.39 |

Cloning replicates refers to number of separate cloning reactions Dilution replicate refers to number of times each cloning replicated was diluted and spotted. The golden gate samples were transformed on separate day form traditional overnight ligation samples. The recovery media was pre-warmed to 37 degrees C. for golden gate sample transformations but not for the traditional overnight ligation samples. Golden Gate samples and traditional overnight ligation samples were sequenced on different days. 3.5% coverage was given to the Traditional overnight ligation sample while 7% coverage was given to golden gate samples. Without being bound by theory, the average read count was lower for traditional overnight ligation samples which could contribute to a higher number of observed dropouts. In addition both cloning replicates for golden gate reactions were sequenced but only one of the replicates for traditional overnight ligation was sequenced due to large number samples being sequenced on that day.

Discussion. The golden gate method was validated for use with a larger oligo pool ($10^5$). 1, 20, and 40 cycles of golden gate all produced very similar results in terms of transfor-mation efficiency, uniformity and number of dropouts; 1 cycle which took little more than hour was sufficient under the conditions tested. There appeared to be very little to no GC bias, and the oligo pool was designed with a relatively uniform GC content from 30 to 80%. This uniformity was maintained as seen in the GC plot for all samples. The golden gate method outperformed the traditional method in terms of 95th/5th, % drop out, uniformity and transformation efficiency, however, without being bound by theory the observed difference might be due to unintended variables between the two sets of experiment.

Traditional overnight ligations and the golden gate experiments were transformed and sequenced on different days. The recovery media for traditional samples was not pre-warmed to 37 C which may contribute to reduced efficiency. In addition, 3.5% coverage was given to traditional samples as opposed to the 7% given to golden gate samples, resulting in higher number of average read count for golden gate samples. Without being bound by theory, this may help explain the increased number of dropouts and higher 95th/5th for traditional samples.

The golden gate method produced as good of a result if not better than the traditional method for cloning of high diversity COP ($10^5$). Given the much simpler cloning protocol and reduced turnaround time for golden gate compared to traditional method, golden gate has advantages over traditional cloning methods. Golden gate also reduced turn out time by (a) decreasing the time required for vector onboarding by about two weeks since it can use circular material (b) combining digestion and ligation into one 1 hr step and eliminating the need for digestion clean up and vector rSAPing and (c) removing the need to for a large scale up the oligo since one 20 μl reaction with 300 fmol of oligo is enough to give sufficient transformation efficiency While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

We claim:

1. A method for nucleic acid assembly, comprising:
providing a plurality of polynucleotides, wherein each of the polynucleotides comprises:
  (i) a 5' adapter sequence comprising at least one Type IIS endonuclease site; or
  (ii) a 3' adapter sequence comprising at least one Type IIS endonuclease site;
amplifying the plurality of polynucleotides using a reaction mixture comprising about 5% to about 100% modified bases; and
mixing the plurality of polynucleotides with a Type IIS restriction enzyme to generate a plurality of nucleic acids.

2. The method of claim 1, wherein the modified bases comprises methyl-dCTP.

3. The method of claim 2, wherein the reaction mixture comprising about 10% to about 50% methyl-dCTP.

4. The method of claim 2, wherein the reaction mixture comprising about 20% to about 40% methyl-dCTP.

5. The method of claim 1, wherein the Type IIS restriction enzyme is selected from the group consisting of AcuI, AlwI, BaeI, BbsI, BbvI, BccI, BceAI, BcgI, BciVI, BcoDI, BfuAI, BmrI, BpmI, BpuEI, BsaI, BsaXI, BseRI, BsgI, BsmAI, BsmBI, BsmFI, BsmI, BspCNI, BspMI, BspQI, BsrDI, BsrI, BtgZI, BtsCI, BtsI, BtsIMutI, CspCI, EarI, EciI, Esp3I, FauI, FokI, HgaI, HphI, HpyAV, MboII, MlyI, MmeI, MnlI, NmeAIII, PleI, SapI, and SfaNI.

6. The method of claim 1, wherein the plurality of polynucleotides comprises up to 100 different sequences.

7. The method of claim 1, wherein at least 80% of the plurality of nucleic acids are represented within 2x of a mean frequency.

8. The method of claim 1, further comprising assembling one or more nucleic acids.

9. The method of claim 8, further comprising ligating the nucleic acids.

10. A method for adapter removal, comprising:
providing a plurality of polynucleotides encoding a gene comprising one or more modifications associated with a disease or disorder, wherein each of the polynucleotides comprises:
  (i) a 5' adapter sequence comprising at least one Type IIS endonuclease site; or
  (ii) a 3' adapter sequence comprising at least one Type IIS endonuclease site;
amplifying the plurality of polynucleotides using a reaction mixture comprising about 5% to about 100% modified bases; and
mixing the plurality of polynucleotides with a Type IIS restriction enzyme to generate a plurality of nucleic acids.

11. A method for adapter removal, comprising:
providing a plurality of polynucleotides encoding a gene comprising one or more modifications associated with a disease or disorder, wherein each of the polynucleotides comprises:
  (i) a 5' adapter sequence comprising at least one Type IIS endonuclease site; and
  (ii) a 3' adapter sequence comprising at least one Type IIS endonuclease site;
amplifying the plurality of polynucleotides using a reaction mixture comprising about 5% to about 100% modified bases; and
mixing the plurality of polynucleotides with a Type IIS restriction enzyme to generate a plurality of nucleic acids.

12. The method of claim 10, wherein the disease or disorder is cancer.

13. The method of claim 10, wherein the modified bases comprises methyl-dCTP.

14. The method of claim 13, wherein the reaction mixture comprising about 10% to about 50% methyl-dCTP.

15. The method of claim 10, wherein the Type IIS restriction enzyme is selected from the group consisting of AcuI, AlwI, BaeI, BbsI, BbvI, BccI, BceAI, BcgI, BciVI, BcoDI, BfuAI, BmrI, BpmI, BpuEI, BsaI, BsaXI, BseRI, BsgI, BsmAI, BsmBI, BsmFI, BsmI, BspCNI, BspMI, BspQI, BsrDI, BsrI, BtgZI, BtsCI, BtsI, BtsIMutI, CspCI, EarI, EciI, Esp3I, FauI, FokI, HgaI, HphI, HpyAV, MboII, MlyI, MmeI, MnlI, NmeAIII, PleI, SapI, and SfaNI.

16. The method of claim 15, wherein the Type IIS restriction enzyme is BsmBI.

17. The method of claim 10, wherein the plurality of polynucleotides comprises up to 100 different sequences.

18. The method of claim 10, wherein at least 80% of the plurality of nucleic acids are represented within 2× of a mean frequency.

19. The method of claim 10, further comprising assembling one or more nucleic acids.

20. The method of claim 19, further comprising assembling one or more nucleic acids using a plurality of overlaps.

\* \* \* \* \*

SEQUENCE LISTING

```
Sequence total quantity: 3
SEQ ID NO: 1              moltype = DNA   length = 18
FEATURE                   Location/Qualifiers
source                    1..18
                          mol_type = other DNA
                          organism = synthetic construct
SEQUENCE: 1
ccatgtgctc acgtctca                                             18

SEQ ID NO: 2              moltype = DNA   length = 18
FEATURE                   Location/Qualifiers
source                    1..18
                          mol_type = other DNA
                          organism = synthetic construct
SEQUENCE: 2
agtcaggatg tcgtctcg                                             18

SEQ ID NO: 3              moltype = DNA   length = 65
FEATURE                   Location/Qualifiers
source                    1..65
                          mol_type = other DNA
                          organism = synthetic construct
SEQUENCE: 3
aattggtgga atctggcggc ggtctggttc agccaggacg tctctacgag tcgcgataat  60
tccaa                                                            65
```